(12) United States Patent
Cui et al.

(10) Patent No.: US 11,482,679 B2
(45) Date of Patent: Oct. 25, 2022

(54) COMPOUND, LIGHT-EMITTING LIFETIME LENGTHENING AGENT, USE OF N-TYPE COMPOUND, FILM AND LIGHT-EMITTING DEVICE

(71) Applicant: KYUSHU UNIVERSITY, NATIONAL UNIVERSITY CORPORATION, Fukuoka (JP)

(72) Inventors: Linsong Cui, Fukuoka (JP); Hajime Nakanotani, Fukuoka (JP); Chihaya Adachi, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 375 days.

(21) Appl. No.: 16/615,984

(22) PCT Filed: May 23, 2018

(86) PCT No.: PCT/JP2018/020627
§ 371 (c)(1),
(2) Date: Nov. 22, 2019

(87) PCT Pub. No.: WO2018/216820
PCT Pub. Date: Nov. 29, 2018

(65) Prior Publication Data
US 2020/0136056 A1 Apr. 30, 2020

(30) Foreign Application Priority Data
May 23, 2017 (JP) .............................. JP2017-101401

(51) Int. Cl.
| | | |
|---|---|---|
| H01L 51/00 | (2006.01) | |
| C07D 251/24 | (2006.01) | |
| C09K 11/02 | (2006.01) | |
| C09K 11/06 | (2006.01) | |
| H01L 51/50 | (2006.01) | |

(52) U.S. Cl.
CPC ........ H01L 51/0067 (2013.01); C07D 251/24 (2013.01); C09K 11/025 (2013.01); C09K 11/06 (2013.01); H01L 51/5016 (2013.01); H01L 51/5028 (2013.01)

(58) Field of Classification Search
CPC ............. H01L 51/0067; H01L 51/5016; H01L 51/5028; H01L 51/5012; H01L 51/0013; H01L 51/0052; H01L 51/0058; H01L 51/0072; H01L 51/5004; H01L 51/5096; H01L 2251/552; H01L 51/0059; H01L 27/3244; H01L 51/0054; H01L 51/0055; H01L 51/0056; H01L 51/5024; H01L 51/5044; H01L 51/0071; H01L 51/504; C07D 251/24; C09K 11/025; C09K 11/06; C09K 2211/1018

USPC ......................................................... 428/690
See application file for complete search history.

(56) References Cited

U.S. PATENT DOCUMENTS

| | | | |
|---|---|---|---|
| 8,859,111 B2 * | 10/2014 | Parham ................ | C07D 333/08 585/27 |
| 9,153,788 B2 | 10/2015 | Adachi et al. | |
| 9,634,262 B2 | 4/2017 | Adachi et al. | |
| 9,660,198 B2 | 5/2017 | Nakagawa et al. | |
| 9,793,492 B2 | 10/2017 | Sagara et al. | |
| 9,818,955 B2 | 11/2017 | Kaji et al. | |
| 9,985,215 B2 | 5/2018 | Adachi et al. | |
| 10,032,995 B2 | 7/2018 | Adachi et al. | |
| 10,276,803 B2 | 4/2019 | Adachi et al. | |
| 10,454,038 B2 * | 10/2019 | Nakagawa ........... | C07D 519/00 |
| 10,490,747 B2 | 11/2019 | Eberle et al. | |
| 10,978,642 B2 * | 4/2021 | Pan ........................ | H01L 51/00 |
| 11,121,184 B2 * | 9/2021 | Song ..................... | H01L 51/504 |
| 2012/0126179 A1 * | 5/2012 | Parham ............... | H01L 51/0067 585/27 |
| 2014/0138669 A1 * | 5/2014 | Nakagawa .......... | C07D 519/00 548/440 |
| 2015/0141642 A1 | 5/2015 | Adachi et al. | |
| 2015/0239880 A1 | 8/2015 | Adachi et al. | |
| 2015/0243897 A1 * | 8/2015 | Montenegro ........ | C07D 213/22 544/215 |
| 2015/0357582 A1 | 12/2015 | Hirata et al. | |
| 2019/0292309 A1 * | 9/2019 | Pan ..................... | H01L 51/0054 |
| 2020/0098992 A1 * | 3/2020 | Pan ........................ | H01L 51/00 |
| 2020/0098996 A1 * | 3/2020 | Koenen ............... | H01L 51/0074 |
| 2021/0151683 A1 * | 5/2021 | Sakaino .............. | C07D 487/04 |
| 2021/0202864 A1 * | 7/2021 | Nakanotani .......... | C07D 209/88 |

FOREIGN PATENT DOCUMENTS

| | | |
|---|---|---|
| JP | 2012-532902 A | 12/2012 |
| JP | 2013-116975 A | 6/2013 |
| JP | 2013-527989 A | 7/2013 |

(Continued)

OTHER PUBLICATIONS

International Preliminary Report on Patentability of Chapter 1, dated Nov. 26, 2019.

(Continued)

*Primary Examiner* — Douglas J McGinty

(74) *Attorney, Agent, or Firm* — Browdy and Neimark, PLLC

(57) ABSTRACT

A light-emitting device having a light-emitting layer containing a delayed fluorescence emitter and an n-type compound has an extended lifetime and high performance. A compound having a triazine ring substituted by a spiro aromatic group can be used as the n-type compound.

13 Claims, 23 Drawing Sheets

(56) References Cited

FOREIGN PATENT DOCUMENTS

| | | |
|---|---|---|
| JP | 2013-253121 A | 12/2013 |
| JP | 2013-256490 A1 | 12/2013 |
| JP | 2014-009224 A | 1/2014 |
| JP | 2014-009352 A | 1/2014 |
| JP | 2015-129240 A | 7/2015 |
| JP | 2015-531755 A | 11/2015 |
| WO | 2013/011954 A1 | 1/2013 |
| WO | 2013/011955 A1 | 1/2013 |
| WO | 2013/081088 A1 | 6/2013 |
| WO | 2013/133359 A1 | 9/2013 |
| WO | 2013/154064 A1 | 10/2013 |
| WO | 2013/161437 A1 | 10/2013 |
| WO | 2014/034535 A1 | 3/2014 |
| WO | 2014/115743 A1 | 7/2014 |
| WO | 2014/122895 A1 | 8/2014 |
| WO | 2014/126200 A1 | 8/2014 |
| WO | 2014/133121 A1 | 9/2014 |
| WO | 2014/136758 A1 | 9/2014 |
| WO | 2014/136860 A1 | 9/2014 |
| WO | 2014/168101 A1 | 10/2014 |
| WO | 2014/189122 A1 | 11/2014 |
| WO | 2014/196585 A1 | 12/2014 |
| WO | 2014/203840 A1 | 12/2014 |
| WO | 2015/002213 A1 | 1/2015 |
| WO | 2015/008580 A1 | 1/2015 |
| WO | 2015/016200 A1 | 2/2015 |
| WO | 2015/019725 A1 | 2/2015 |
| WO | 2015/072470 A1 | 5/2015 |
| WO | 2015/072537 A1 | 5/2015 |
| WO | 2015/080182 A1 | 6/2015 |
| WO | 2015/080183 A1 | 6/2015 |
| WO | 2015/108049 A1 | 7/2015 |
| WO | 2015/129714 A1 | 9/2015 |
| WO | 2015/129715 A1 | 9/2015 |
| WO | 2015/133501 A1 | 9/2015 |
| WO | 2015/136880 A1 | 9/2015 |
| WO | 2015/137136 A1 | 9/2015 |
| WO | 2015/137202 A1 | 9/2015 |
| WO | 2015/137244 A1 | 9/2015 |
| WO | 2015/146541 A1 | 10/2015 |
| WO | 2015-159541 A1 | 10/2015 |
| WO | 2016/062371 A1 | 4/2016 |

OTHER PUBLICATIONS

International Search Report and Search Opinion, dated Aug. 21, 2018.
Joyama et al., H., "Highly efficient organic light-emitting diodes from delayed fluorescence", Nature 492, 234-238 (2012).
Reineke, S., "Organic light-emitting diodes: Phosphorescence meets its match", Nat. Photonics, 8, 269-270 (2014).
Etherington et al., M. K., "Revealing the spin-vibronic coupling mechanism of thermally activated delayed fluorescence", Nat. Commun. 7, 13680 (2016).
Di et al., D., "High-performance light-emitting diodes based on carbene-metal-amides", Science DOI: DOI: 10.1126/science.aah4345 (2017).
Lin et al., T. A., "Sky-Blue Organic Light Emitting Diode with 37% External Quantum Efficiency Using Thermally Activated Delayed Fluorescence from Spiroacridine-Triazine Hybrid", Adv. Mater. 28, 6976-6983 (2016).
Tsujimoto et al., H., "Thermally Activated Delayed Fluorescence and Aggregation Induced Emission with Through-Space Charge Transfer", J. Am. Chem. Soc. 139, 4894-4900 (2017).
Wong et al., M. Y., "Organic Thermally Activated Delayed Fluorescence Materials for Organic Light-Emitting Diodes", Adv. Mater. DOI: 10.1002/adma.201605444 (2017).
Cui et al., L. S., "Controlling Singlet-Triplet Energy Splitting for Deep-Blue Thermally Activated Delayed Fluorescence Emitters", Angew. Chem. Int. Ed. 129, 1593-1597 (2017).
Gómez-Bombarelli et al., R., "Design of efficient molecular organic light-emitting diodes by a high-throughput virtual screening and experimental approach", Nat. Mater. 15, 1120-1127 (2016).
Zhang et al., Q., "Efficient blue organic light-emitting diodes employing thermally activated delayed fluorescence", Nat. Photonics, 8, 326-332 (2014).
Tang et al., C. W. "Organic electroluminescent diodes", Appl. Phys. Lett. 51, 913-915 (1987).
Jankus et al., V., "Highly efficient TADF OLEDs: How the emitter-host interaction controls both the excited state species and electrical properties of the devices to achieve near 100% triplet harvesting and high efficiency", Adv. Funct. Mater. 24, 6178-6186, (2014).
Holmes et al., R. J., "Blue organic electrophosphorescence using exothermic host-guest energy transfer", Appl. Phys. Lett. 82, 2422-2424 (2003).
Duan et al., L., "Strategies to Design Bipolar Small Molecules for OLEDs: Donor-Acceptor Structure and Non-Donor-Acceptor Structure", Adv. Mater. 23, 1137-1144 (2011).
Chaskar et al., A., "Bipolar host materials: a chemical approach for highly efficient electrophosphorescent devices", Adv. Mater 23, 3876-3895 (2011).
Han et al., T. H., "Ultrahigh-efficiency solution-processed simplified small-molecule organic light-emitting diodes using universal host materials", Sci. Adv. 2, e1601428 (2016).
Cui et al., L.-S., "Benzimidazobenzothiazole-Based Bipolar Hosts to Harvest Nearly All of the Excitons from Blue Delayed Fluorescence and Phosphorescent Organic Light-Emitting Diodes", Angew. Chem. Int. Ed. 55, 6864-6868 (2016).
May et al., F., "Design rules for charge-transport efficient host materials for phosphorescent organic light-emitting diodes", J. Am. Chem. Soc. 134, 13818-13822 (2012).
Kim et al., D., "Design of efficient ambipolar host materials for organic blue electrophosphorescence: theoretical characterization of hosts based on carbazole derivatives", J. Am. Chem. Soc. 133, 17895-17900 (2011).
Holmes et al., R. J., "Efficient, deep-blue organic electrophosphorescence by guest charge trapping", Appl. Phys. Lett. 83, 3818-3820 (2003).
Wu et al., C., "Study of Energy Transfer and Triplet Exciton Diffusion in Hole-Transporting Host Materials", Adv. Funct. Mater. 19, 3157-3164 (2009).
Zhang et al., Y., "Tenfold increase in the lifetime of blue phosphorescent organic light-emitting diodes", Nat. Commun. 5, 5008 (2014).
Malliaras et al., "The roles of injection and mobility in organic light emitting diodes", J. Appl. Phys. 83, 5399-5403 (1998).
Cui et al., L. S., "Controlling Synergistic Oxidation Processes for Efficient and Stable Blue Thermally Activated Delayed Fluorescence Devices", Adv. Mater. 28, 7620-7625 (2016).
Giebink et al., N., "Direct evidence for degradation of polaron excited states in organic light emitting diodes", J. Appl. Phys. 105, 124514 (2009).
Kulkarni et al., "Electron transport materials for organic light-emitting diodes", Chem. Mater. 16, 4556-4573 (2004).
Abbaszadeh et al., D. "Elimination of charge carrier trapping in diluted semiconductors", Nat. Mater. 15, 628-633 (2016).
Zhang et al., D., "High-Efficiency Fluorescent Organic Light-Emitting Devices Using Sensitizing Hosts with a Small Singlet-Triplet Exchange Energy", Adv. Mater. 26, 5050-5055 (2014).
Nakanotani et al., H., "Promising operational stability of high-efficiency organic light-emitting diodes based on thermally activated delayed fluorescence", Sci. Rep. 3, 2127(2013).
Poriel et al., C., "Structure-Properties Relationship of 4-Substituted-Spirobifluorenes as Hosts for Phosphorescent Organic Light Emitting Diodes: An overview", J. Mater. Chem. C, 5, 3869-3897 (2017).
Zhang,et al., D., "Sterically shielded blue thermally activated delayed fluorescence emitters with improved efficiency and stability", Mater. Horiz. 3, 145-151 (2016).
Hirata et al., S., "Highly efficient blue electroluminescence based on thermally activated delayed fluorescence", Nat. Mater. 14, 330-336 (2015).

(56) References Cited

OTHER PUBLICATIONS

Cui et al., L.-S., "Pure Hydrocarbon Hosts for≈ 100% Exciton Harvesting in Both Phosphorescent and Fluorescent Light-Emitting Devices", Adv. Mater. 27, 4213-4217 (2015).
Chen et al., "1,3,5-Triazine derivatives as new electron transport-type host materials for highly efficient green phosphorescent OLEDs", Journal of Materials Chemistry, 2009, 19(43), pp. 8112-8118.

* cited by examiner

[Fig. 1A]
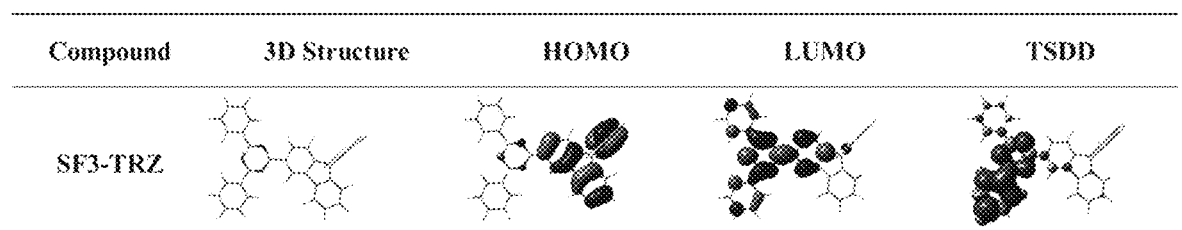
[Fig. 1B]
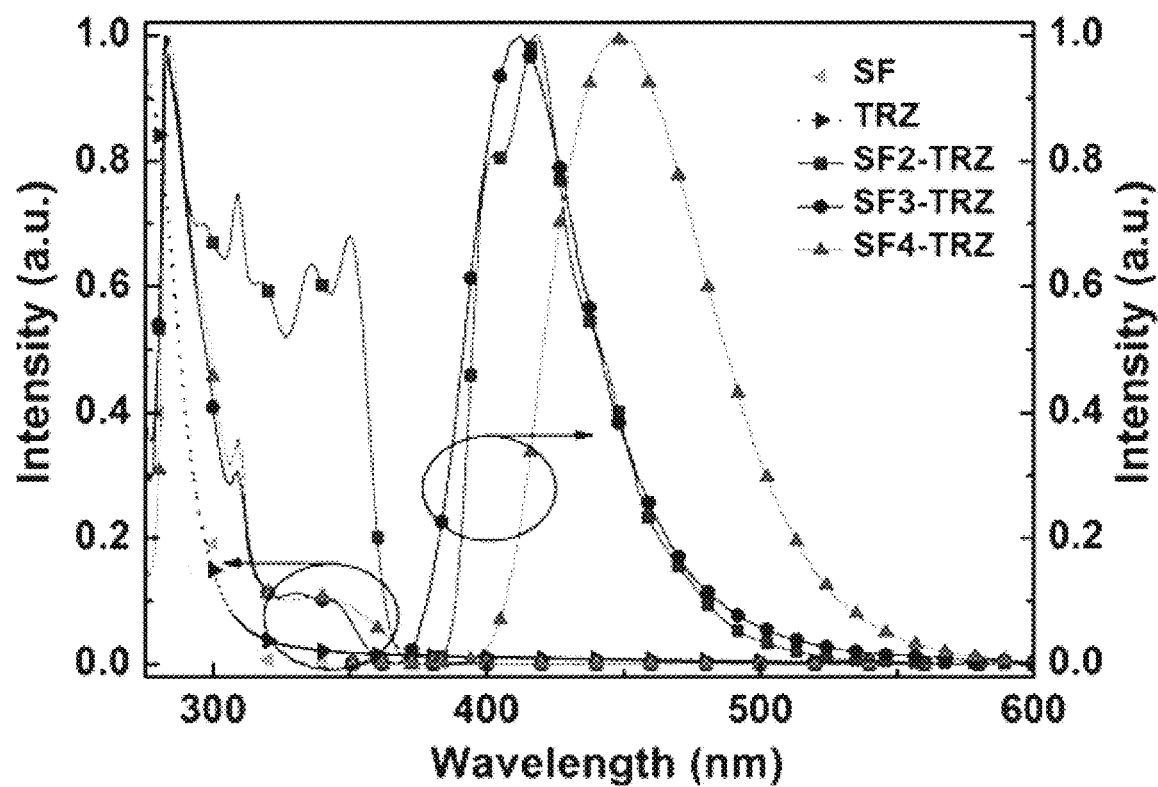

[Fig. 1C]
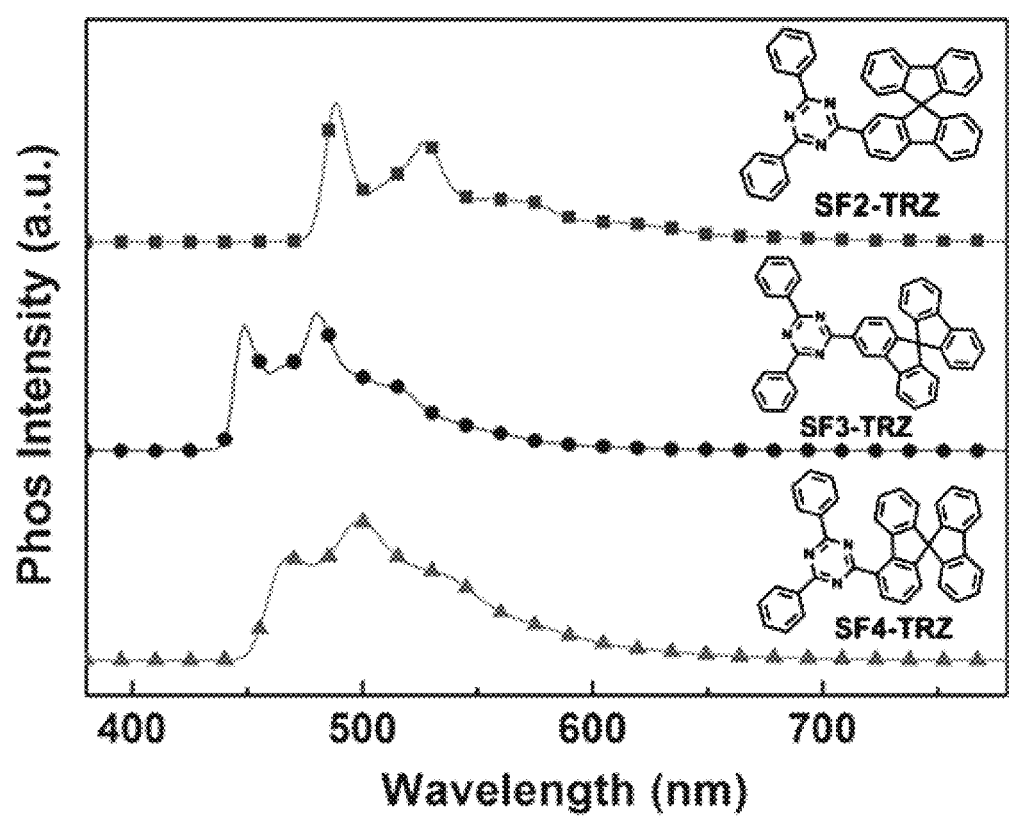

[Fig. 1D]
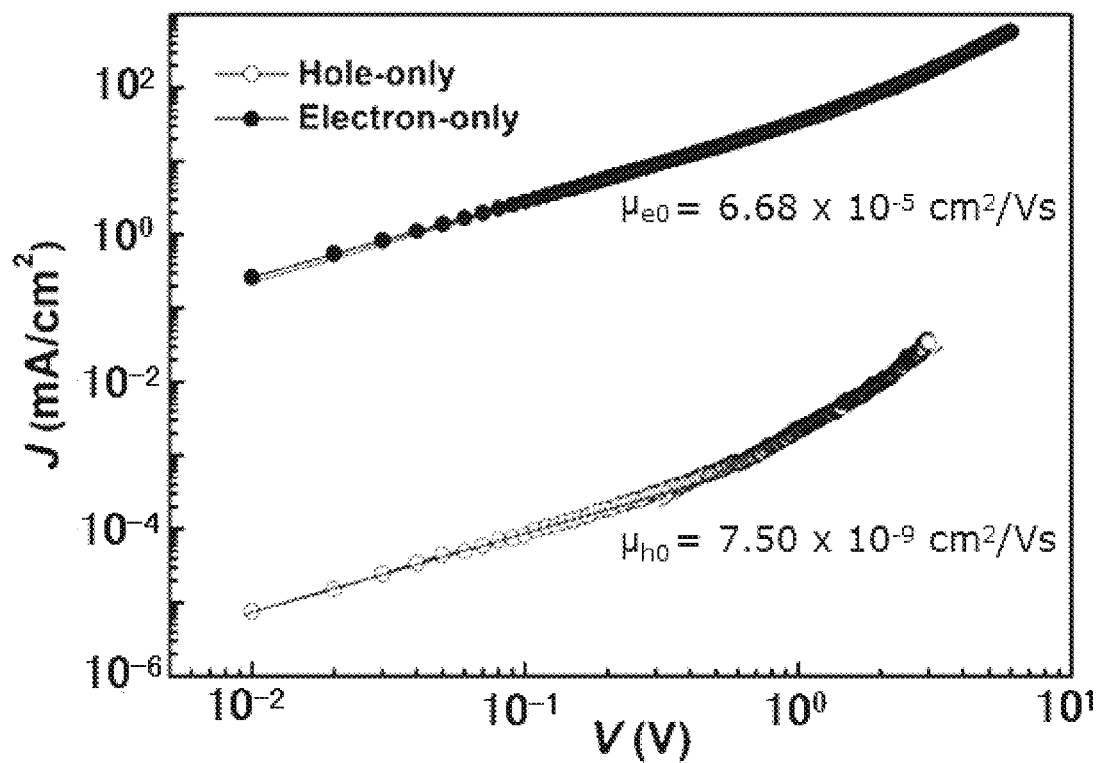
[Fig. 1E]
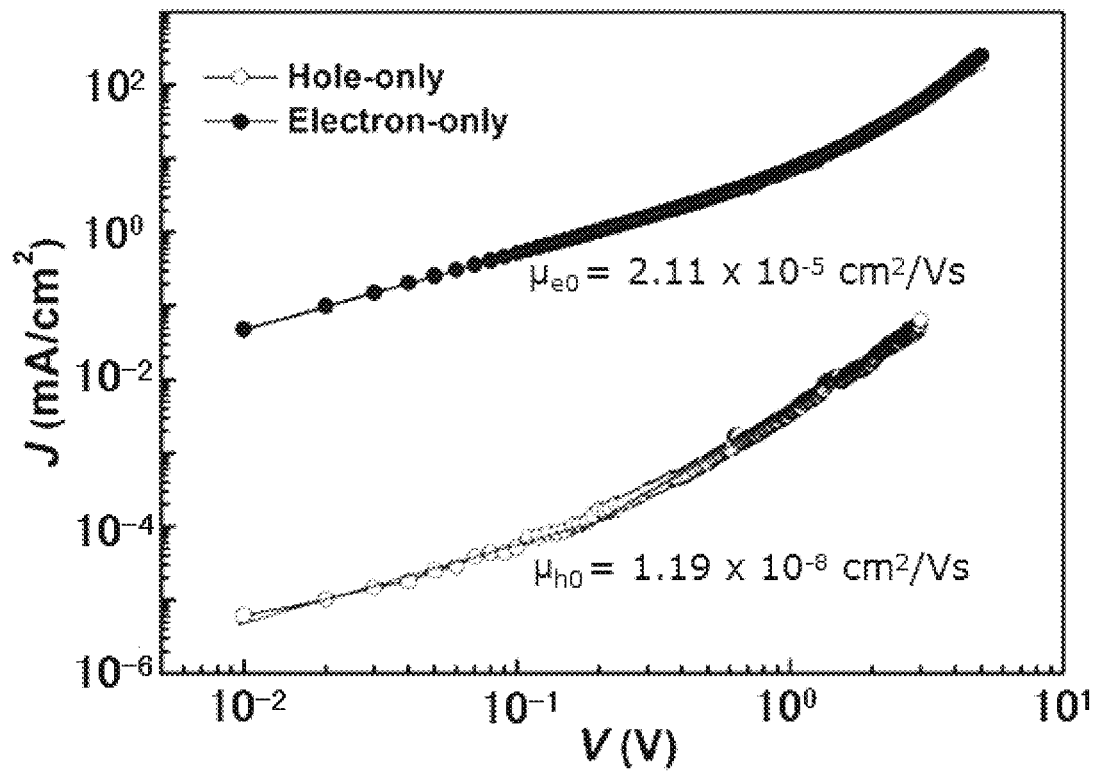

[Fig. 2A]
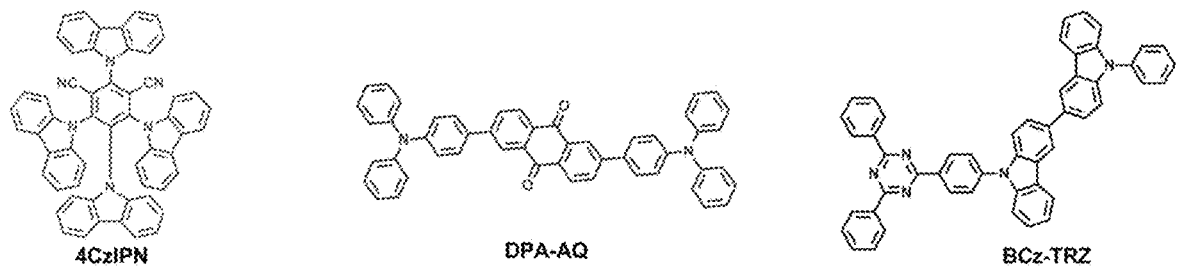
[Fig. 2B]
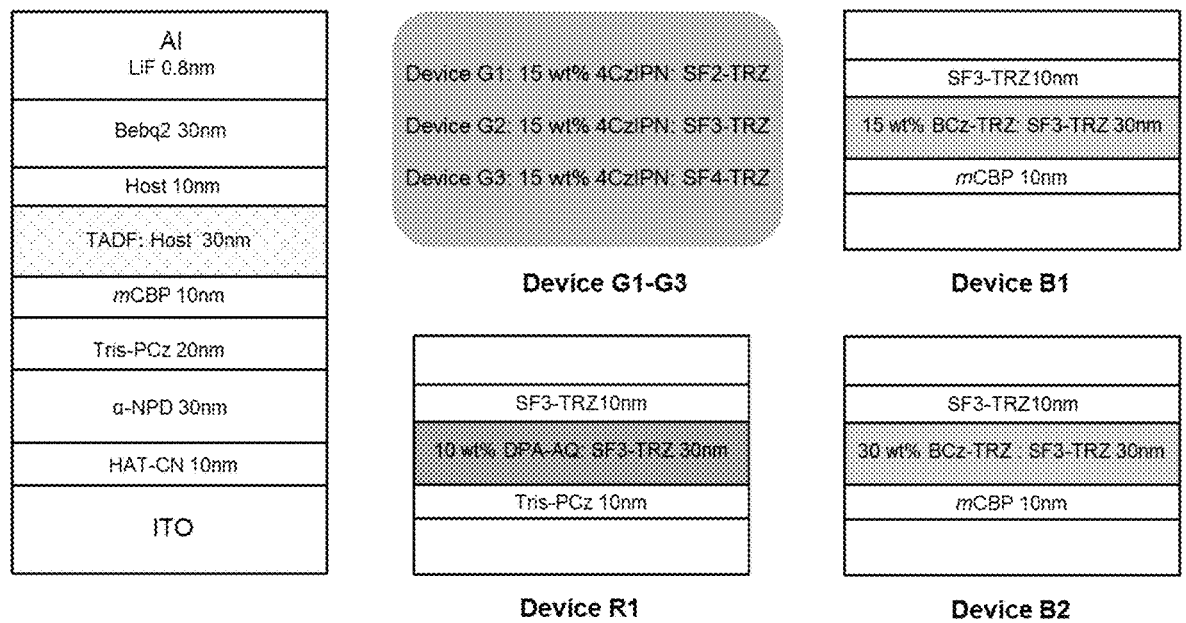

[Fig. 3A]
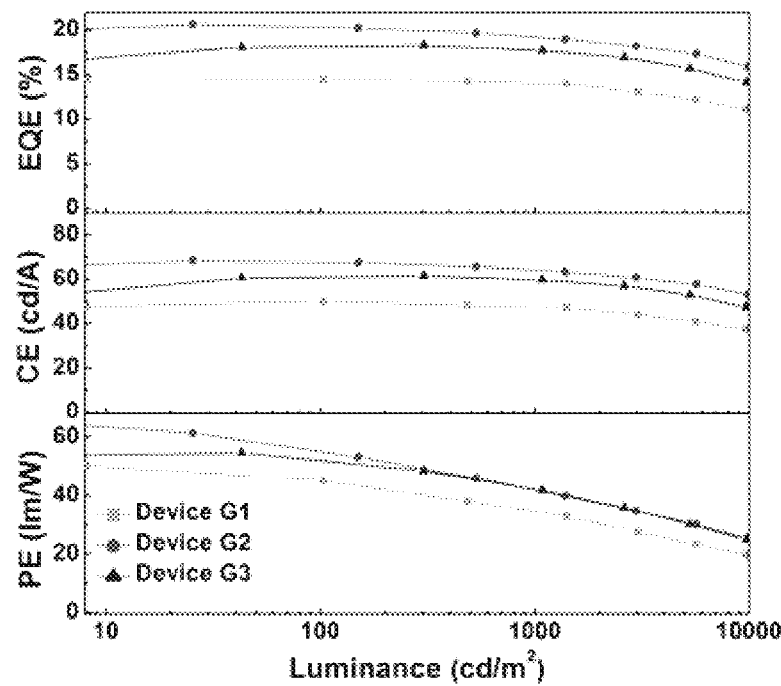
[Fig. 3B]
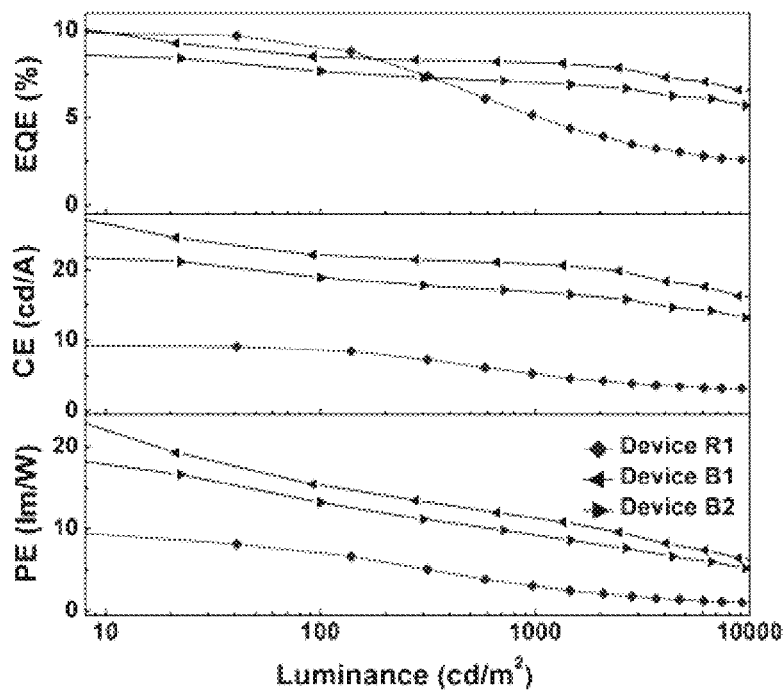

[Fig. 3C]
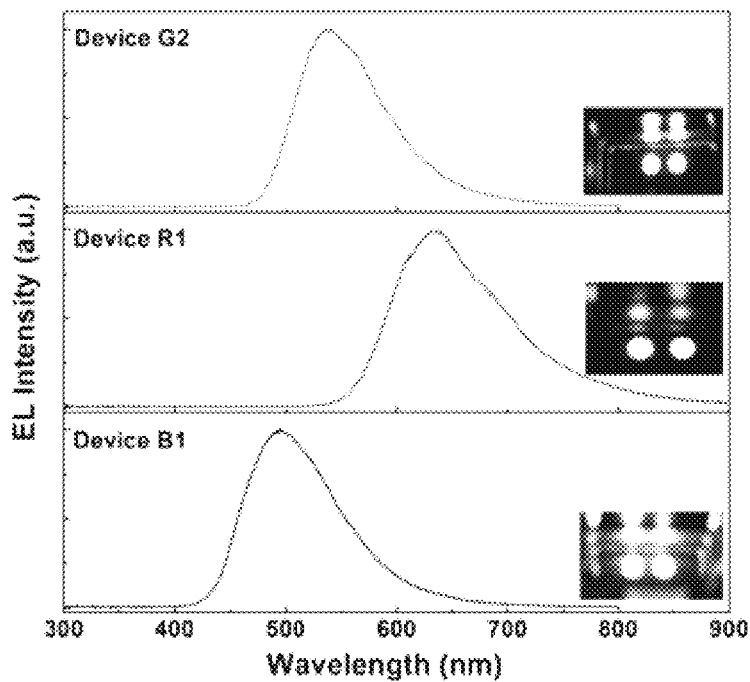
[Fig. 3D]
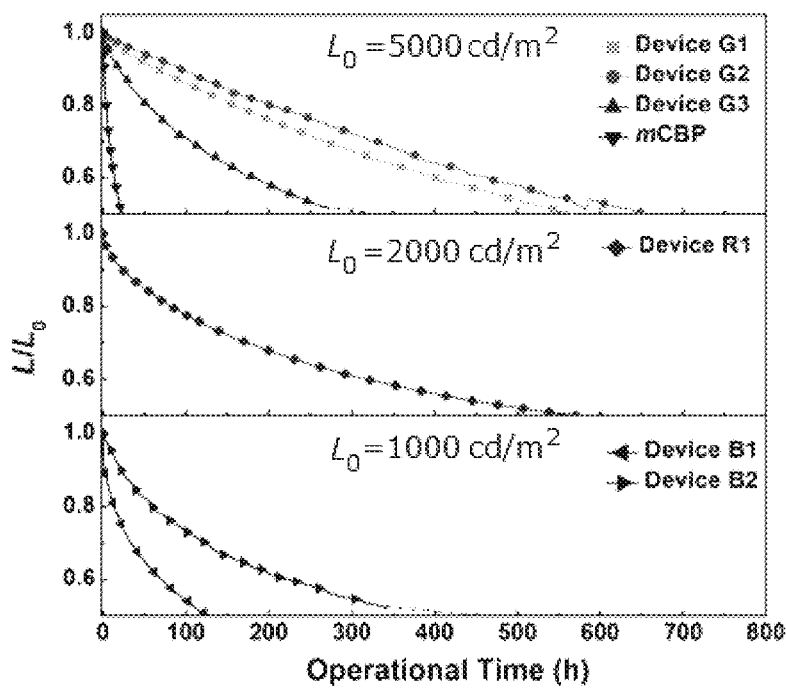

[Fig. 4A]
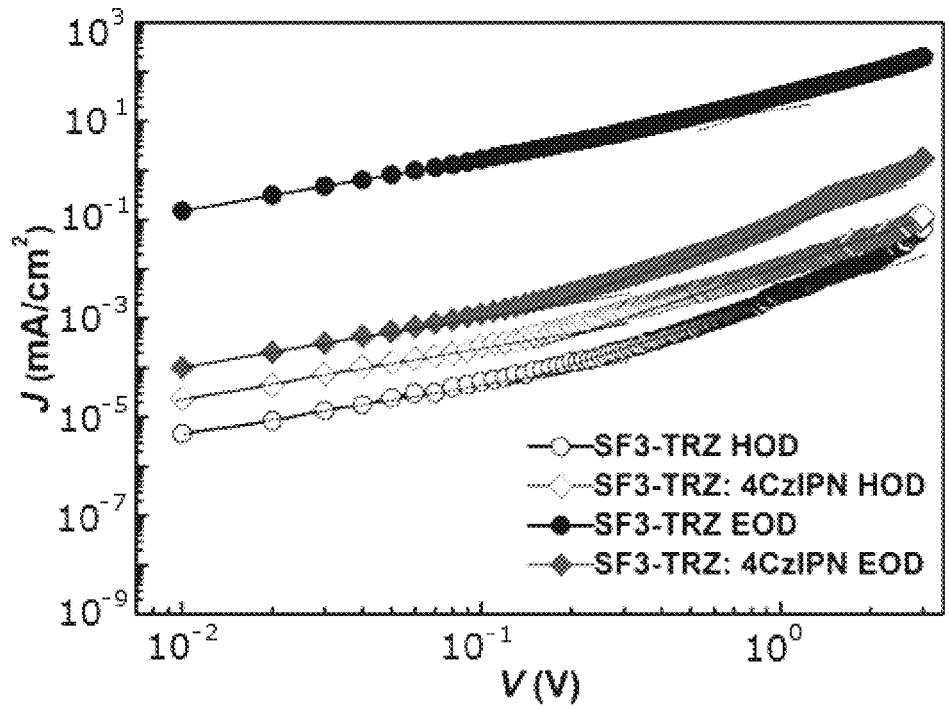
[Fig. 4B]
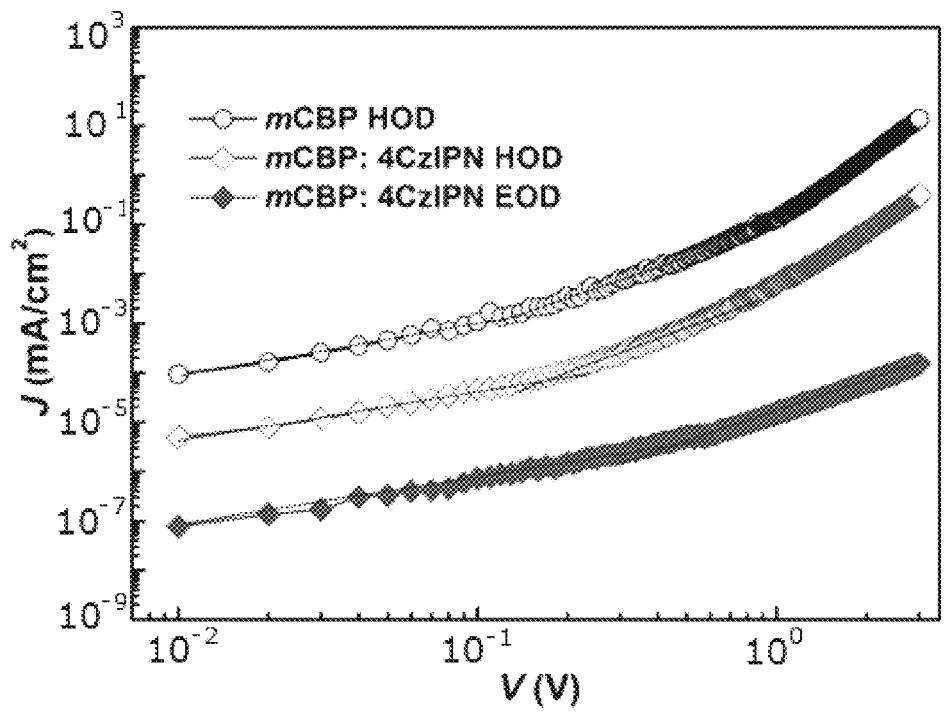

[Fig. 5]
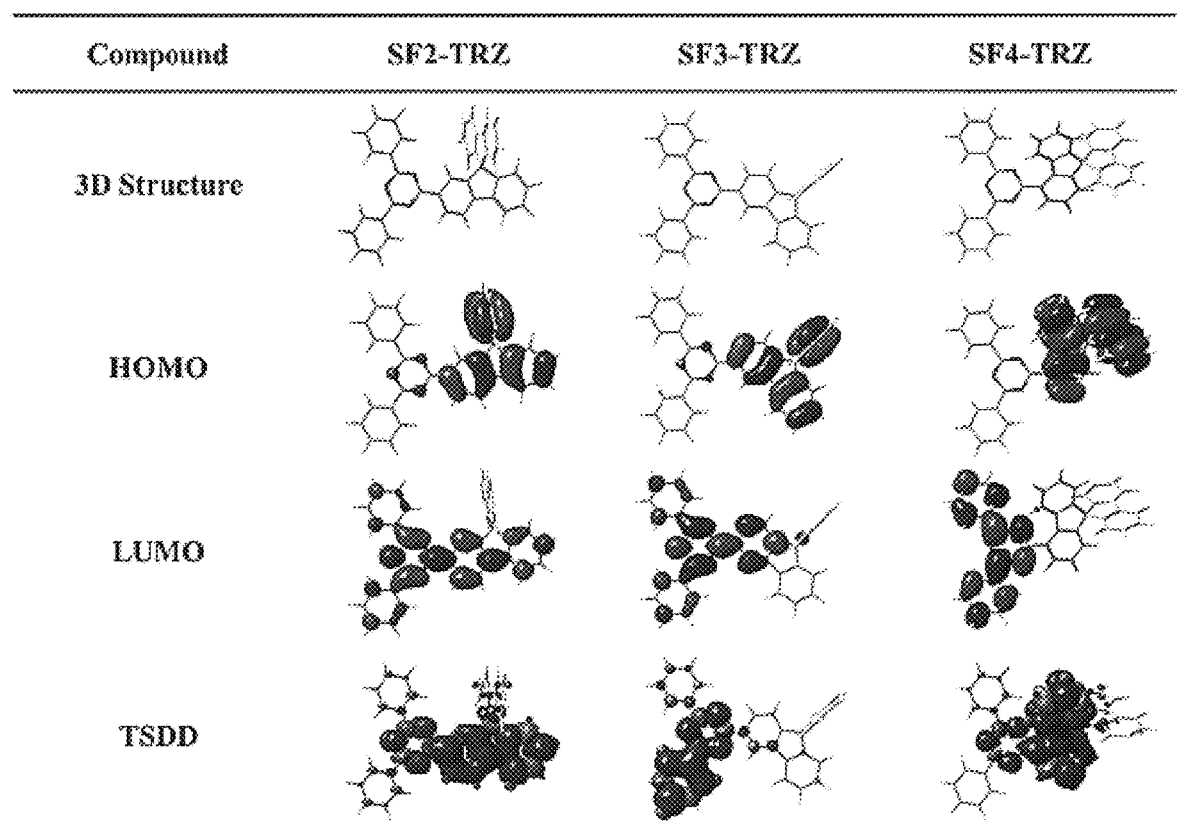

[Fig. 6]
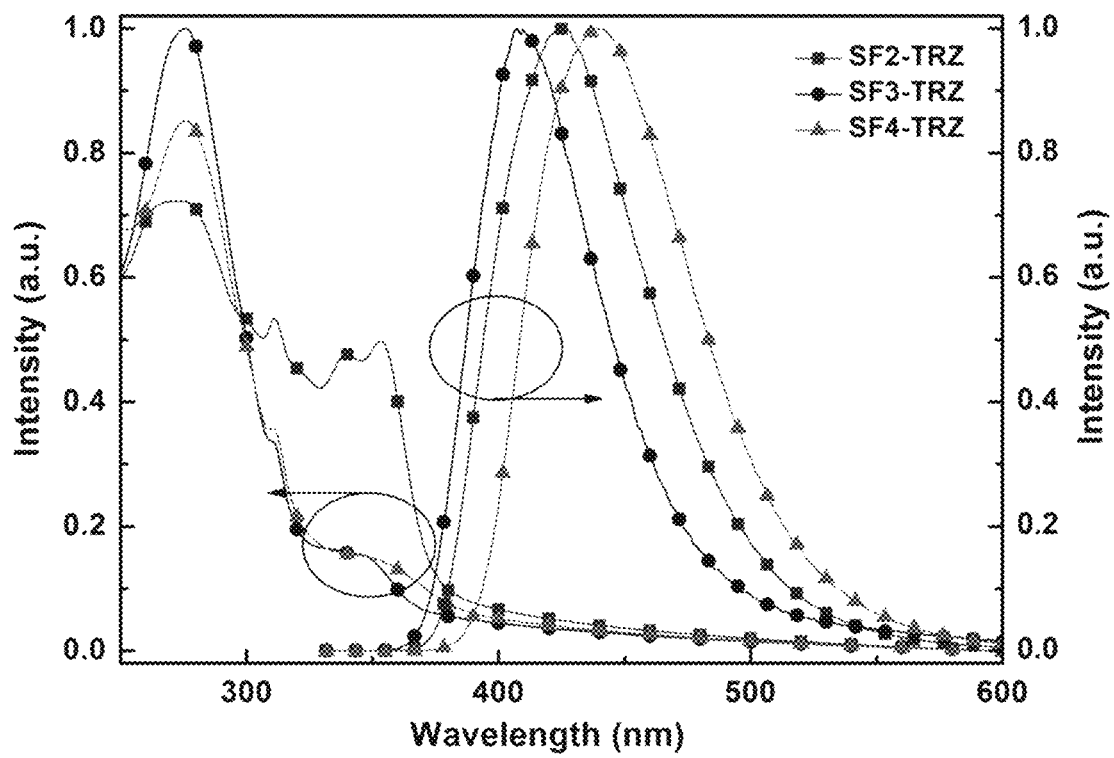
[Fig. 7]
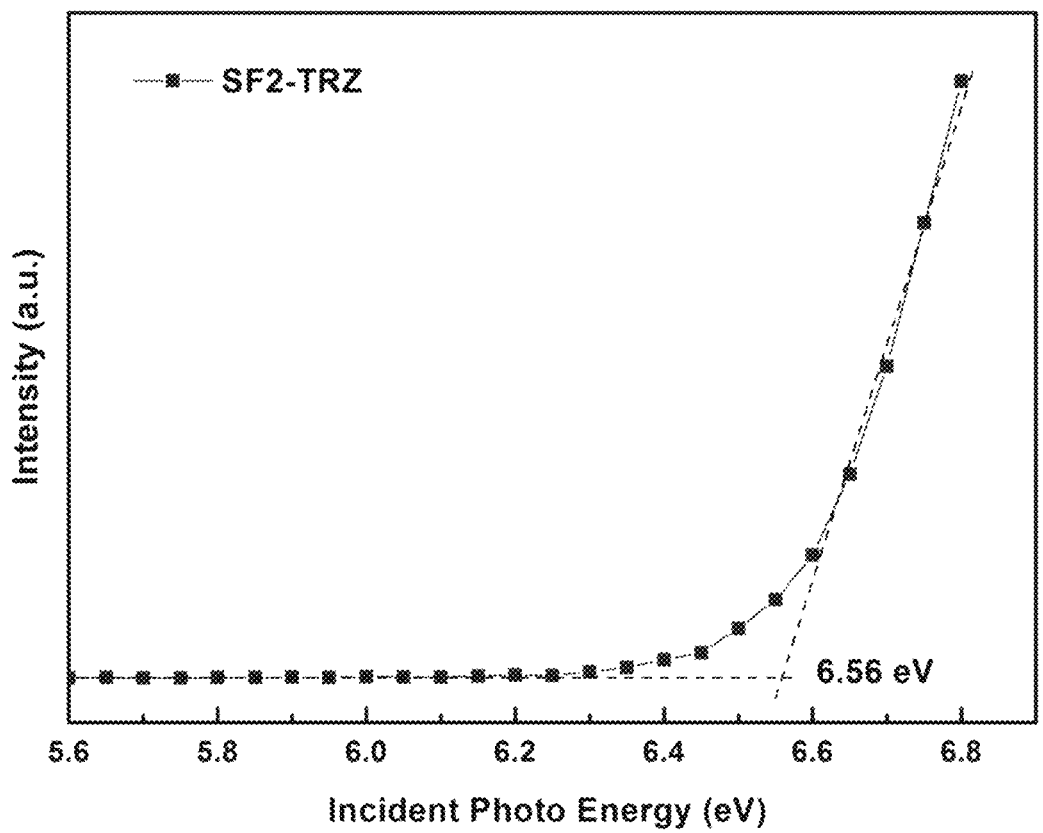

[Fig. 8]
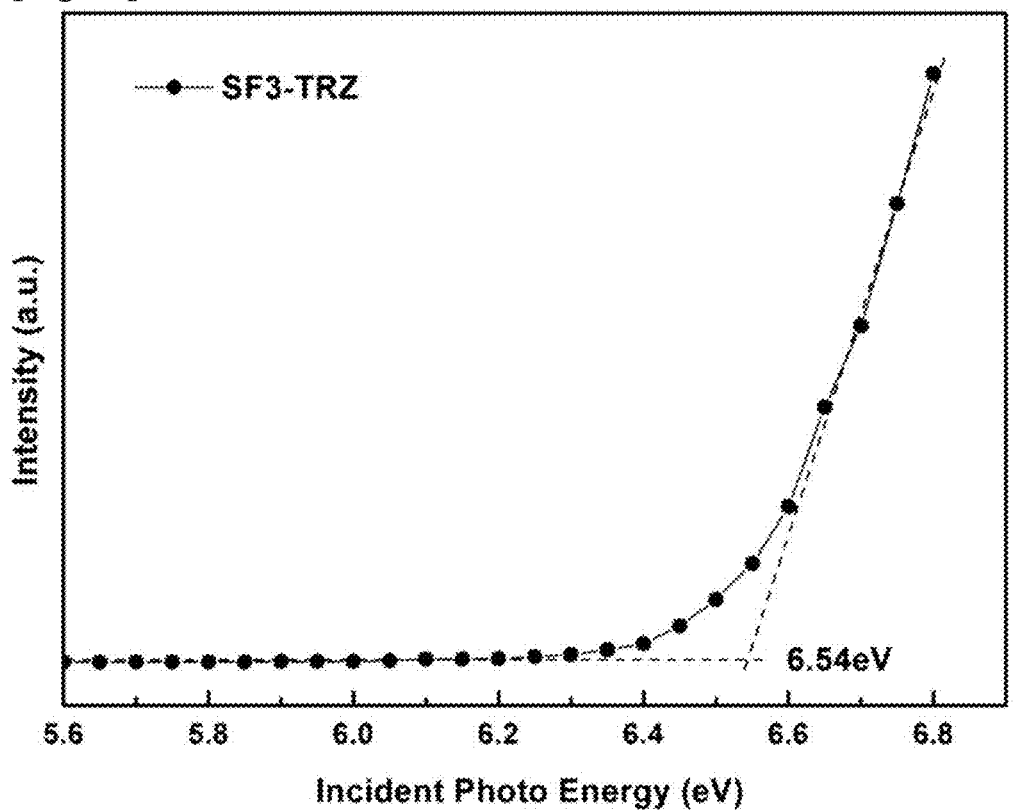
[Fig. 9]
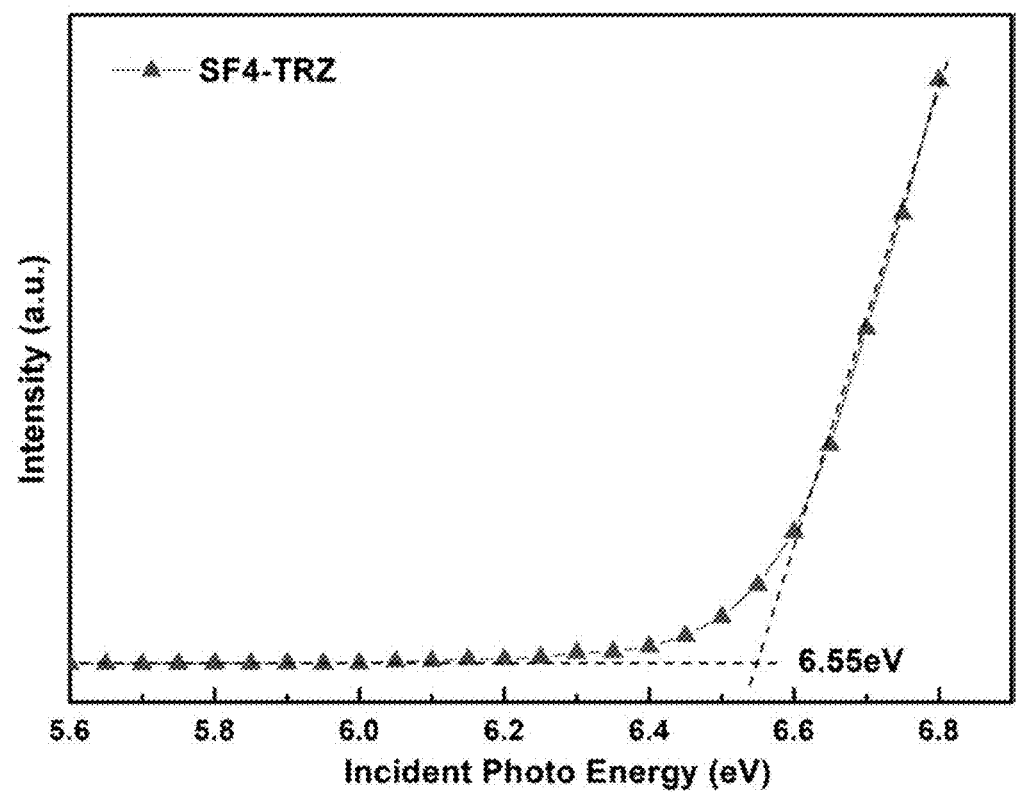

[Fig. 10A]
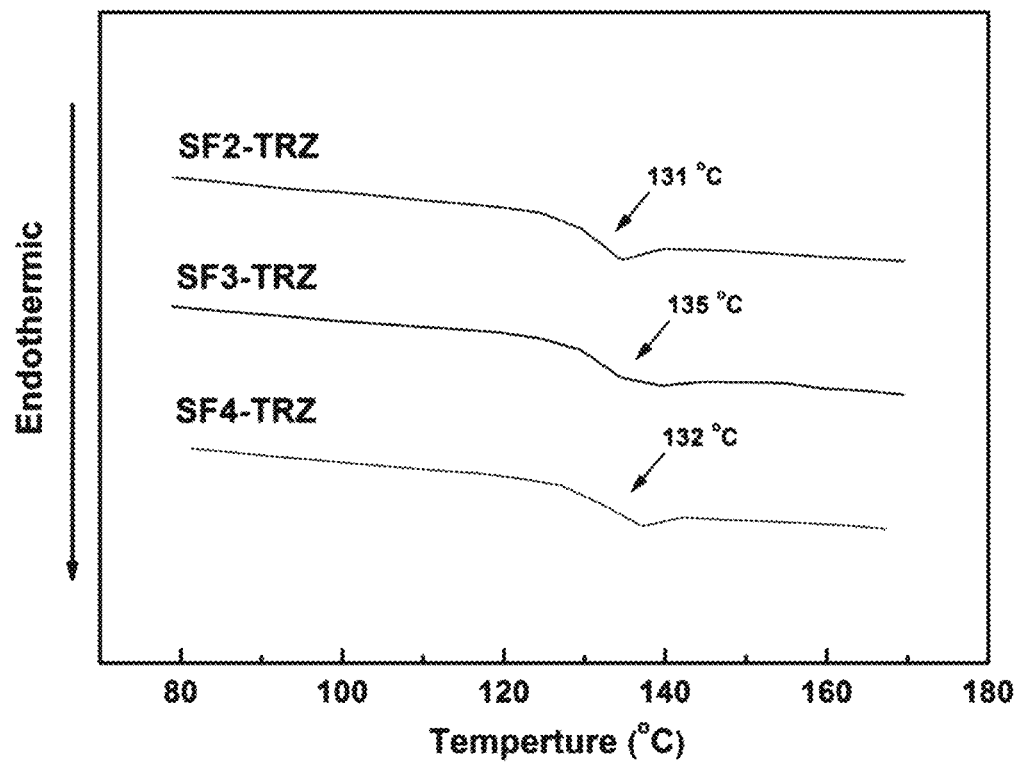
[Fig. 10B]
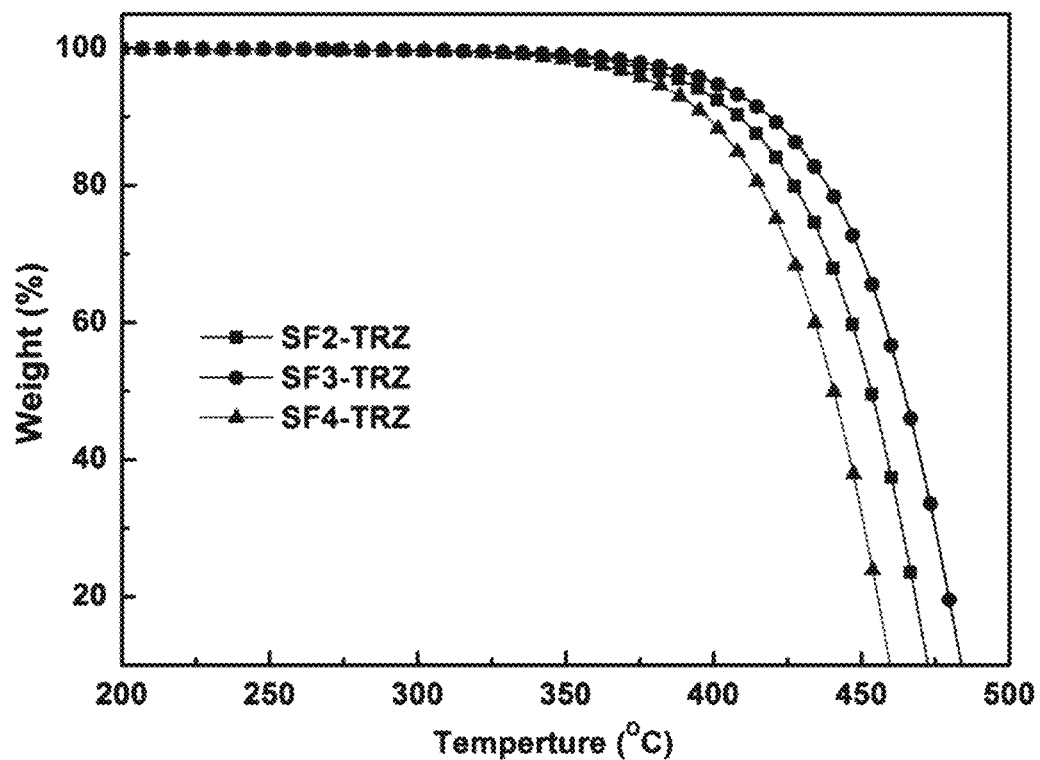

[Fig. 11]
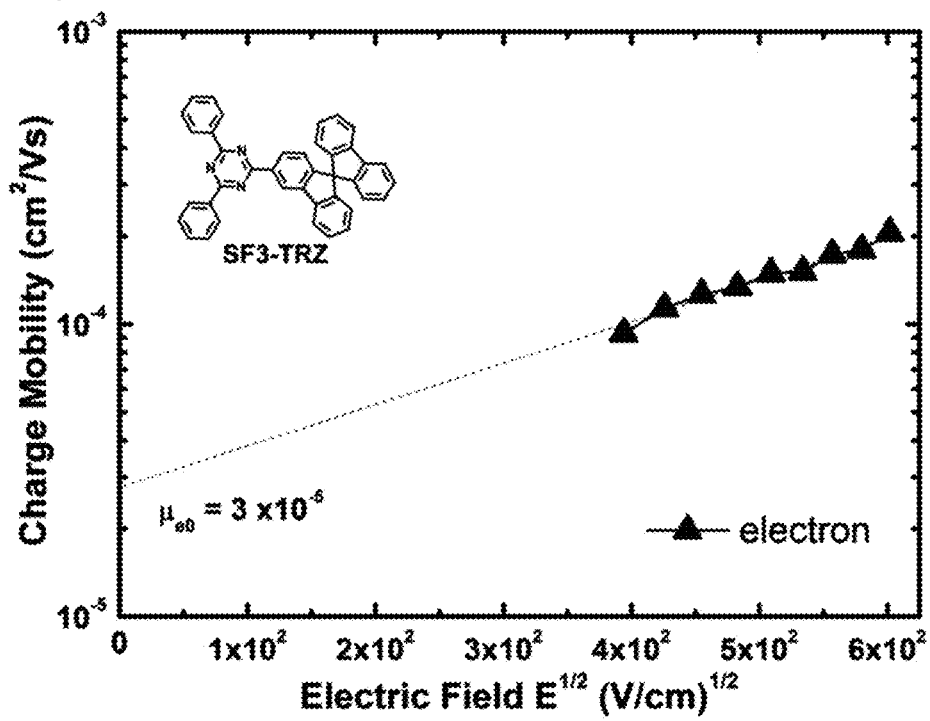
[Fig. 12]
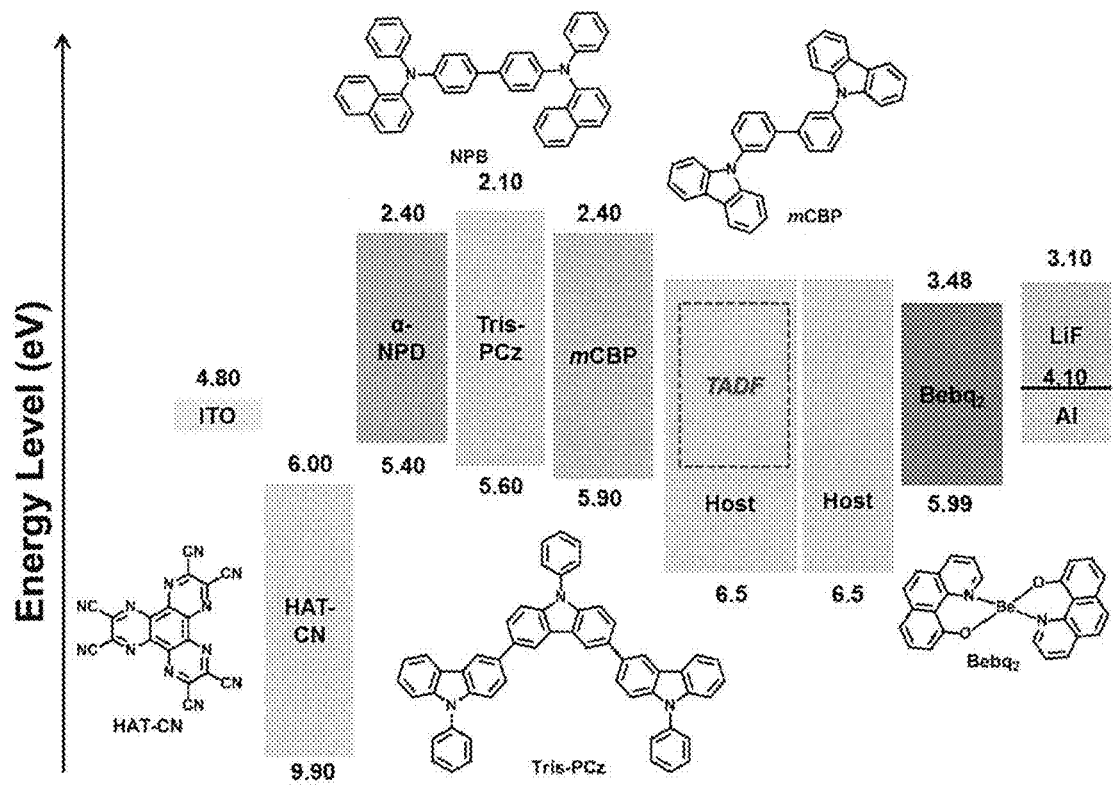

[Fig. 13]
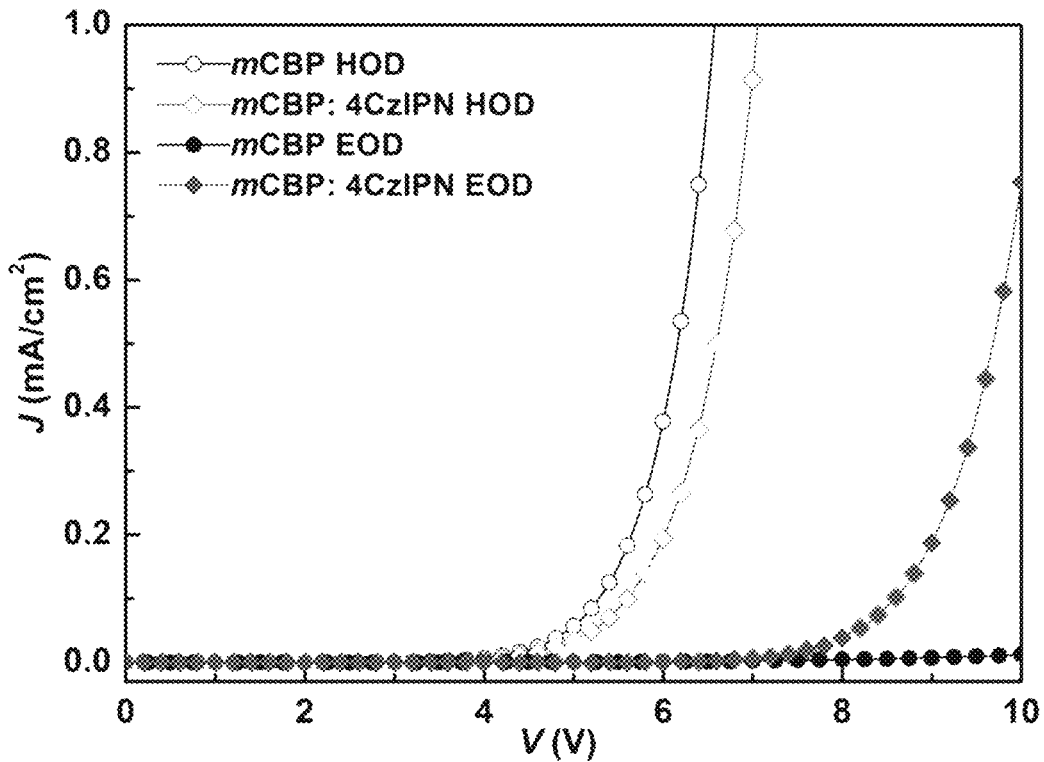
[Fig. 14]
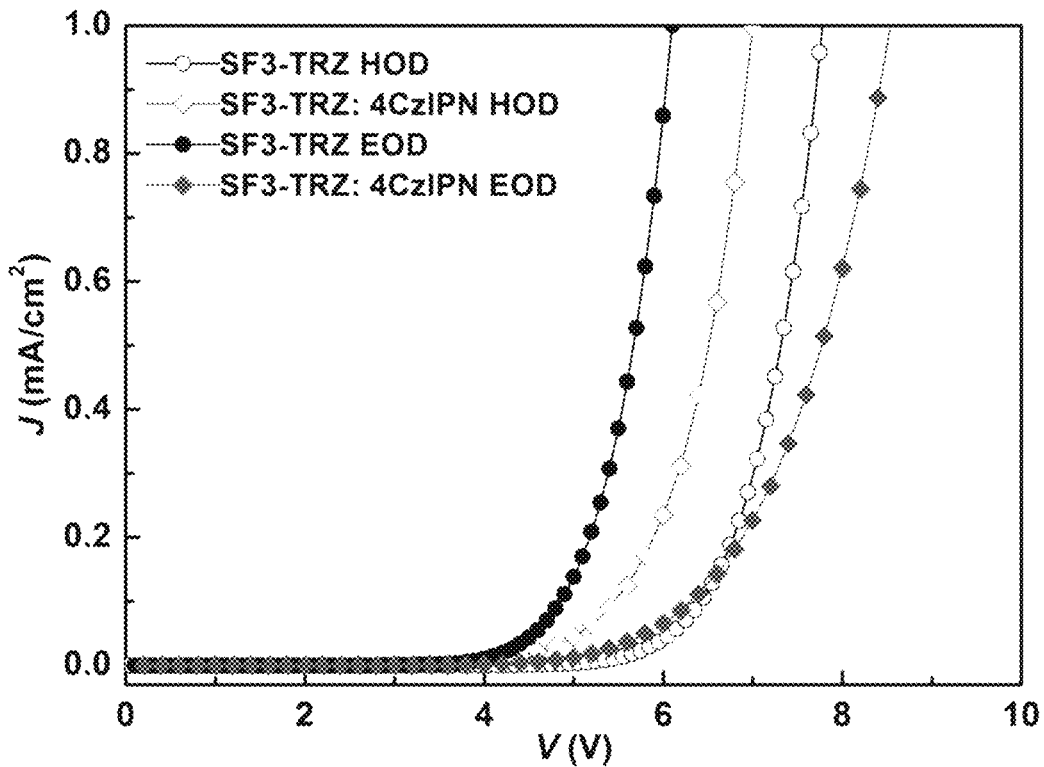

[Fig. 15]
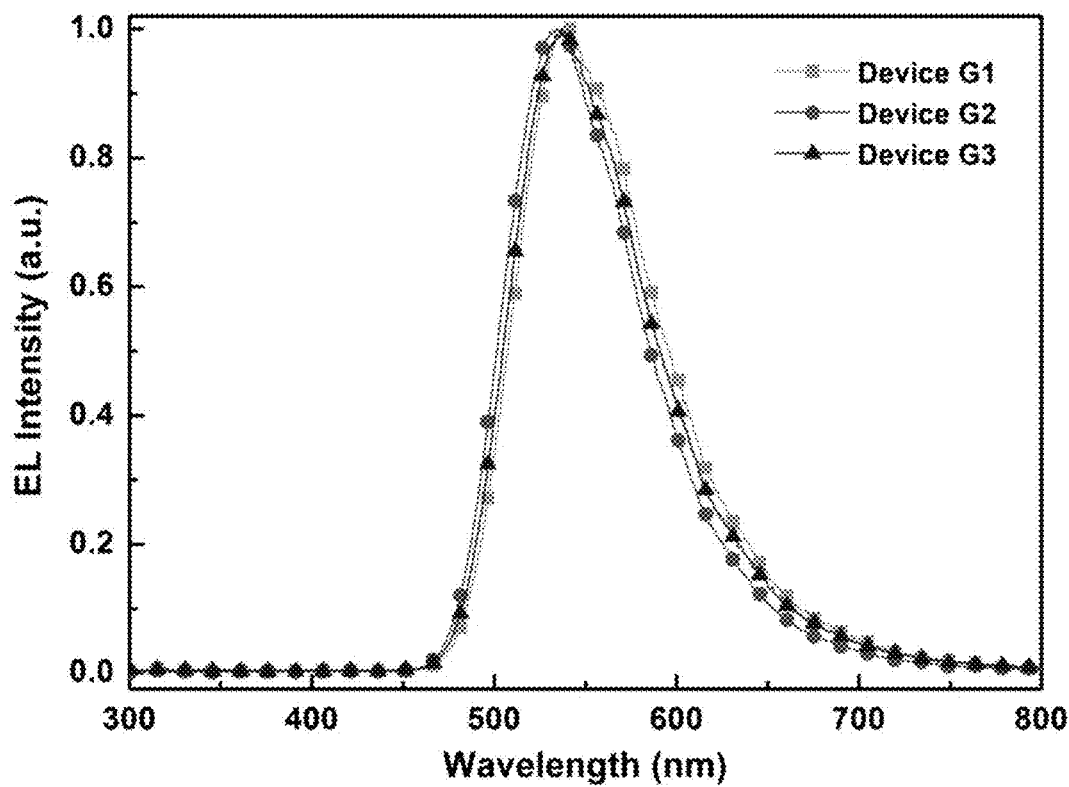
[Fig. 16]
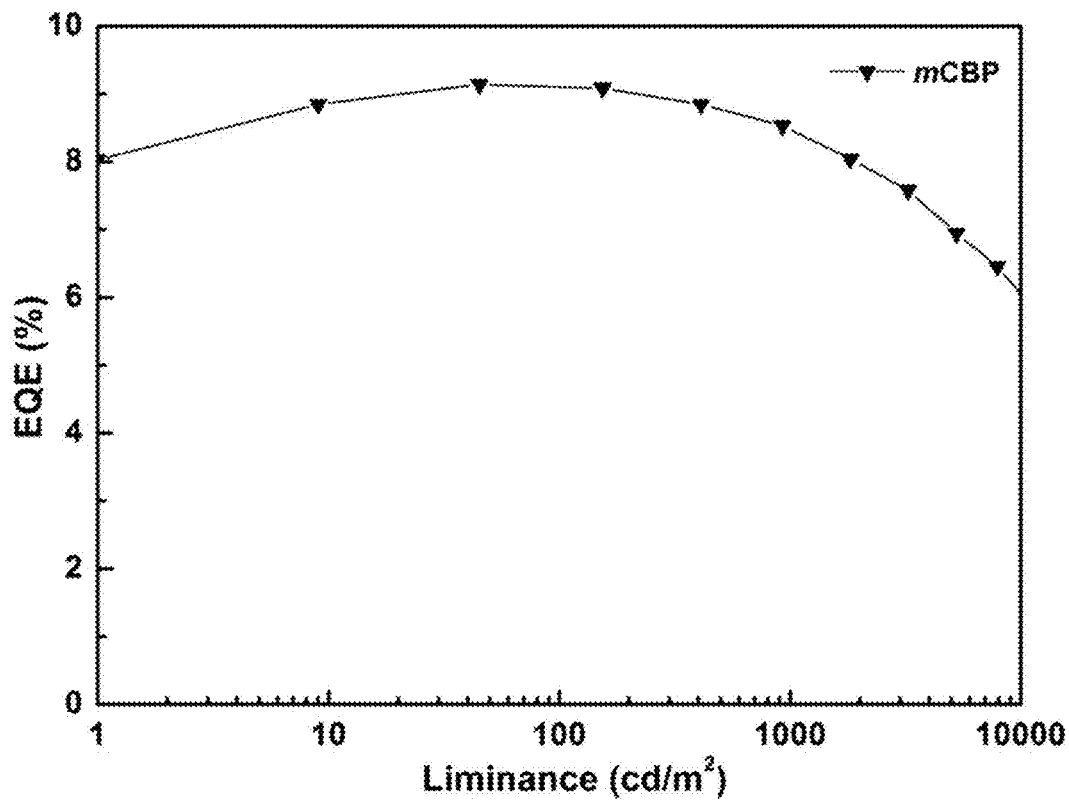

[Fig. 17]
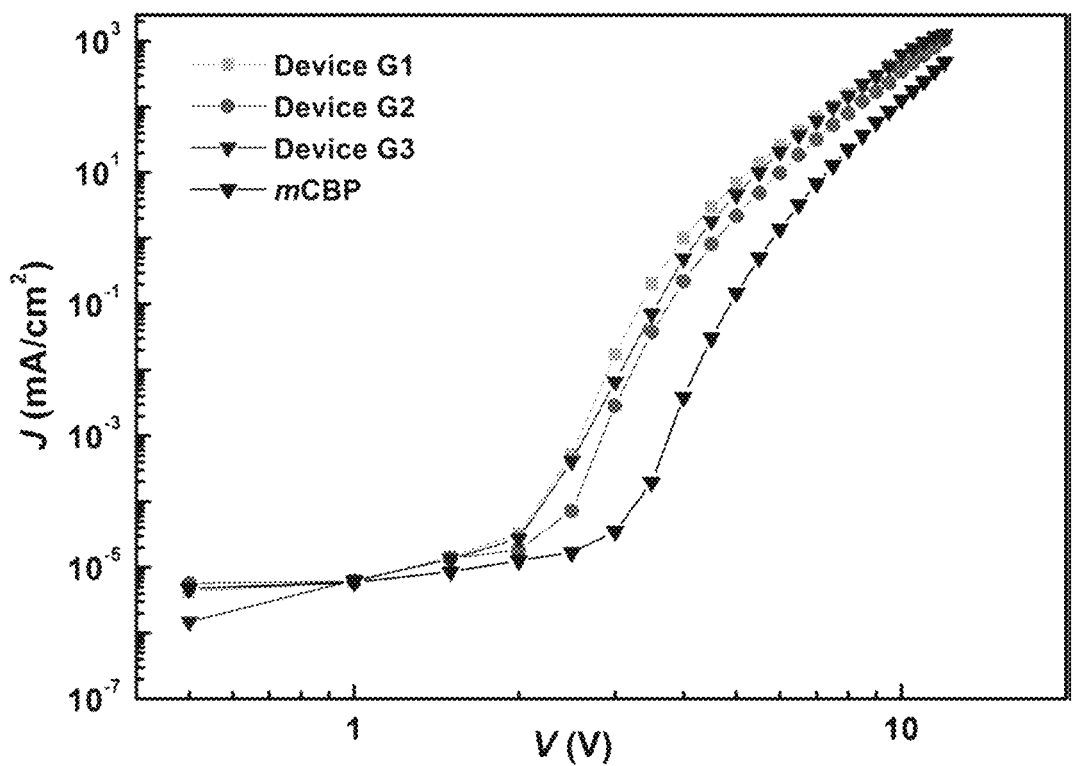
[Fig. 18]
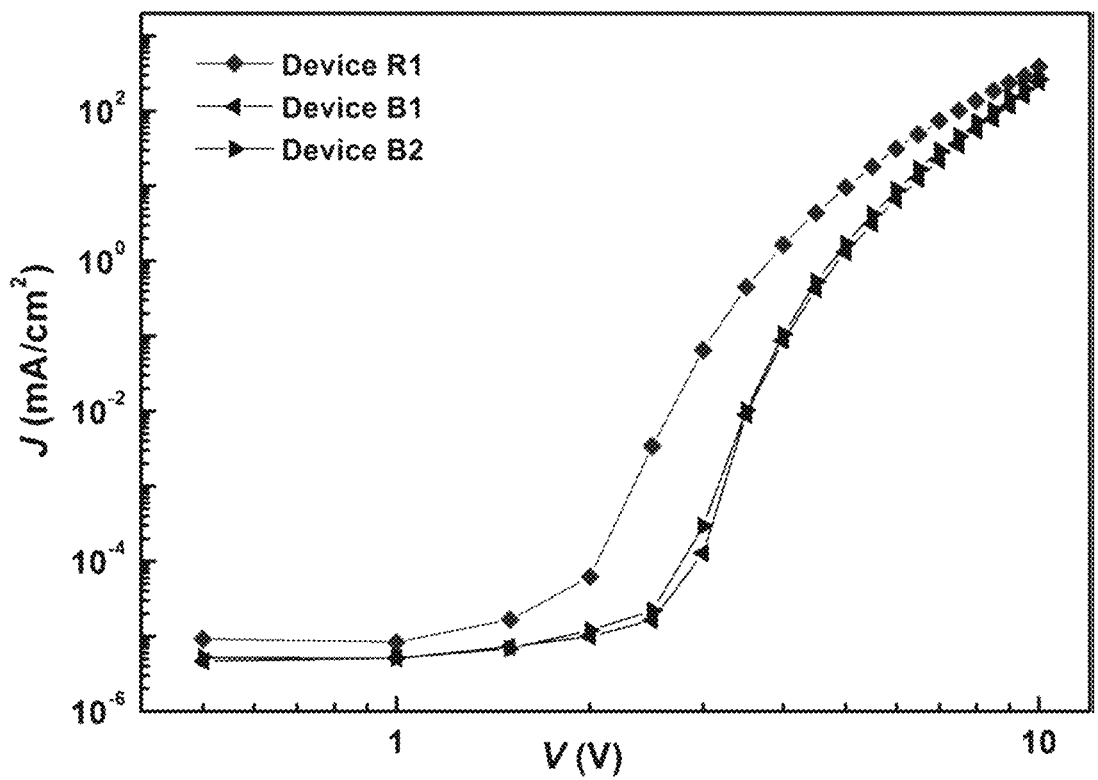

[Fig. 19]
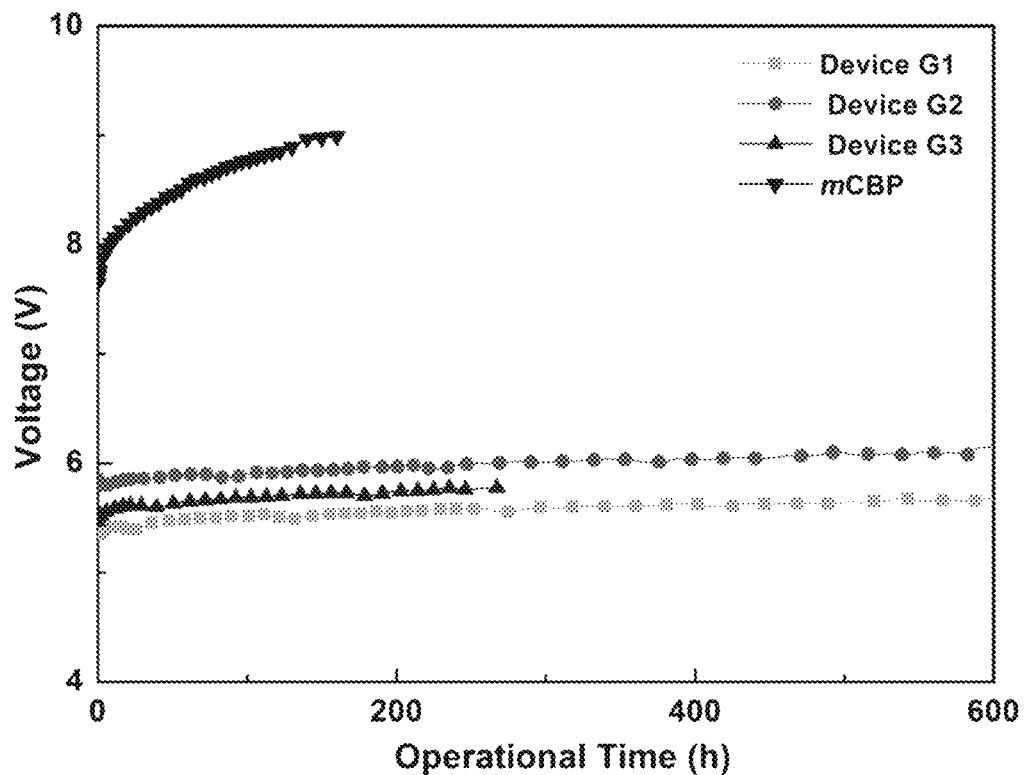
[Fig. 20]
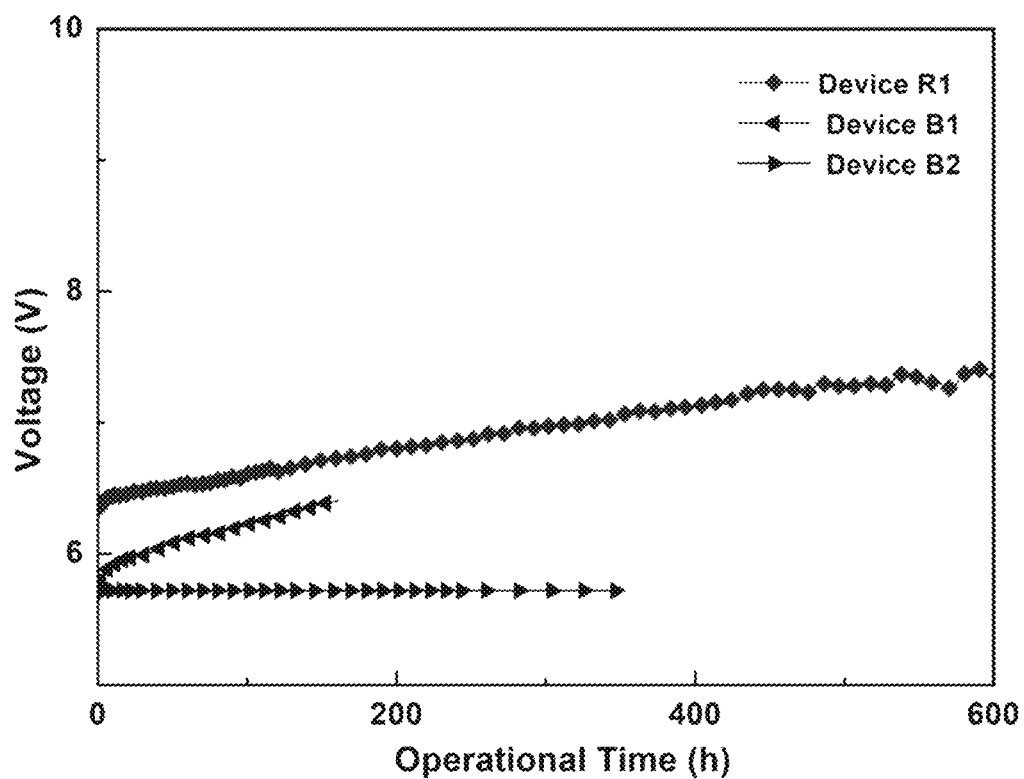

[Fig. 21]
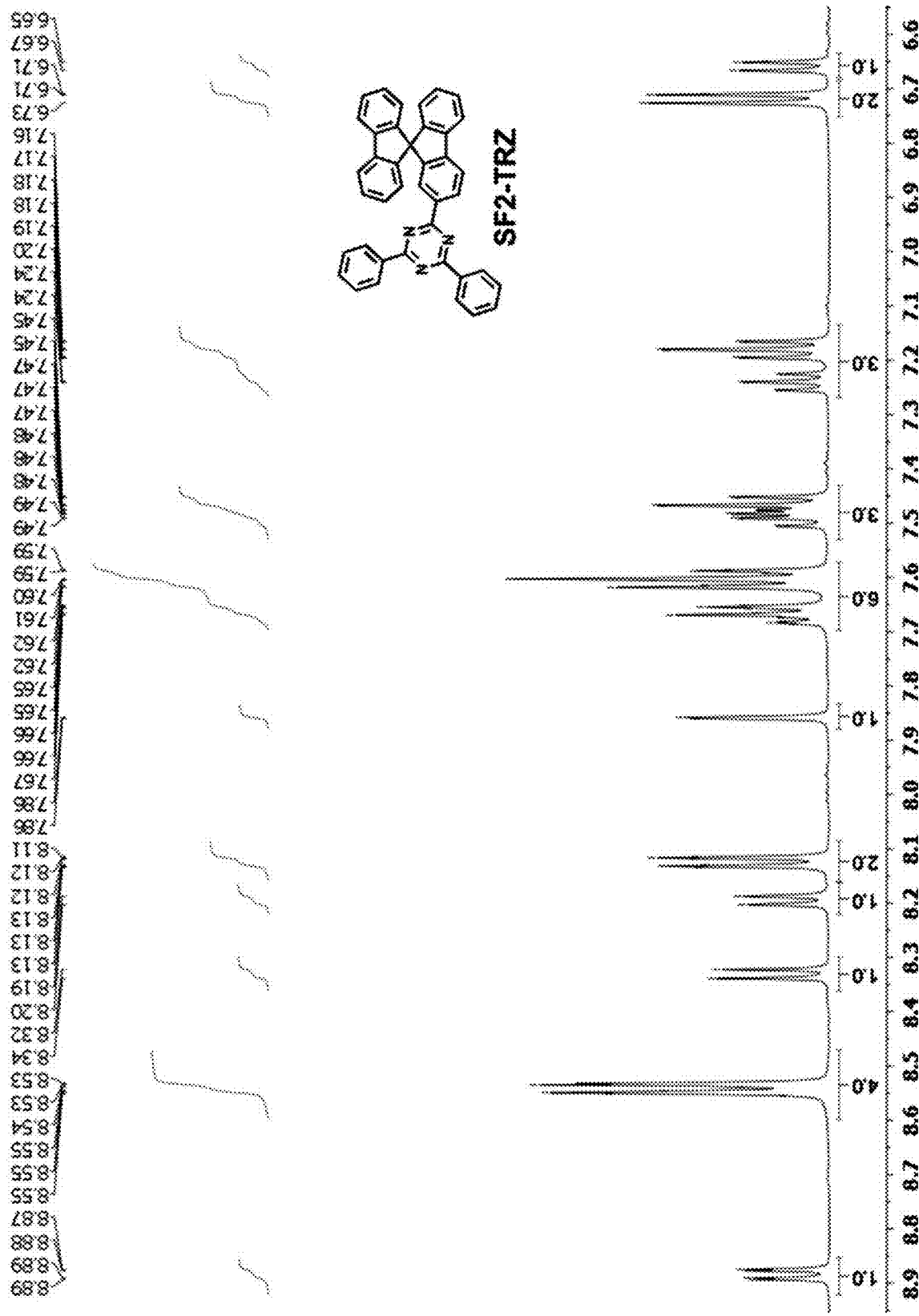

[Fig. 22]
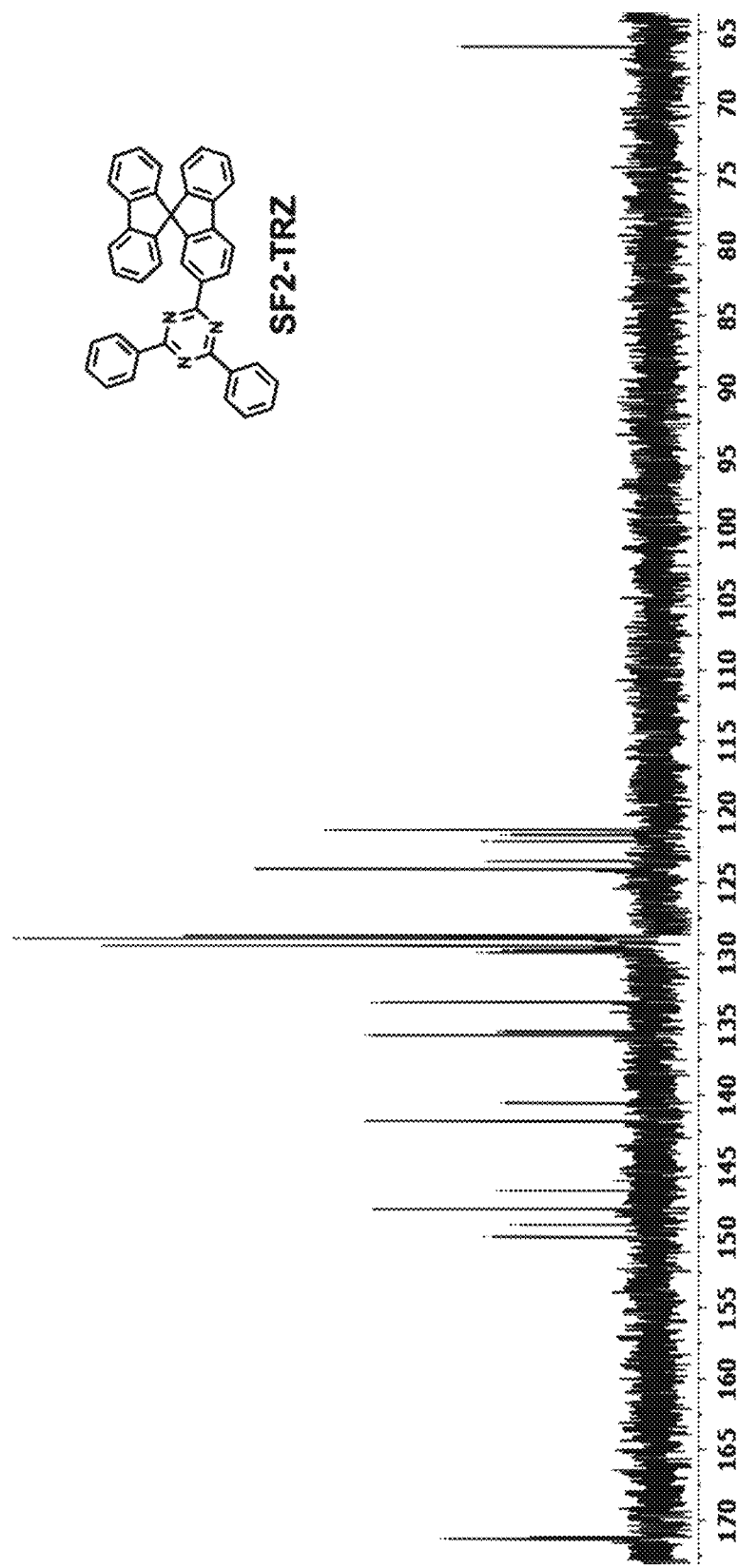

[Fig. 23]
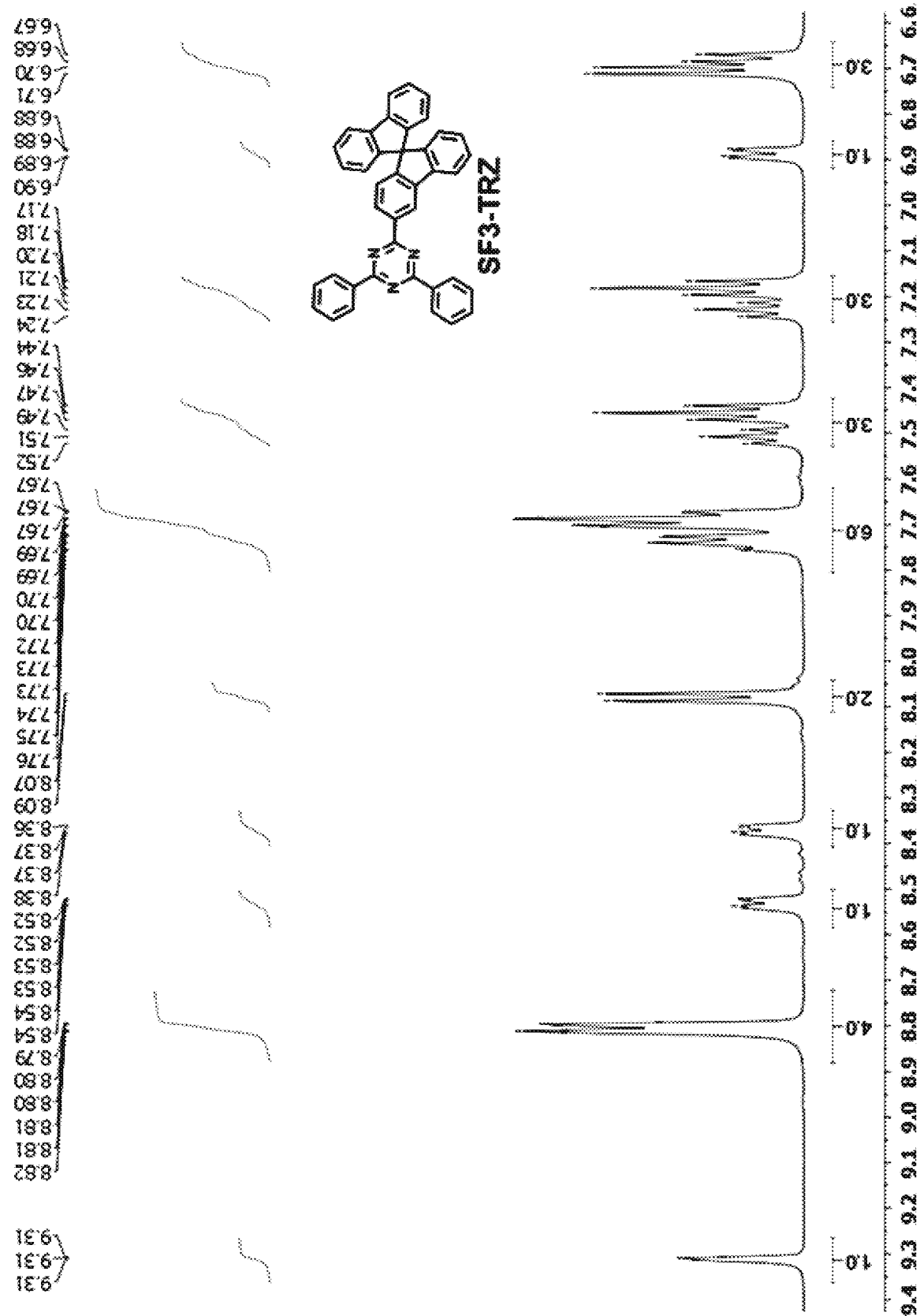

[Fig. 24]
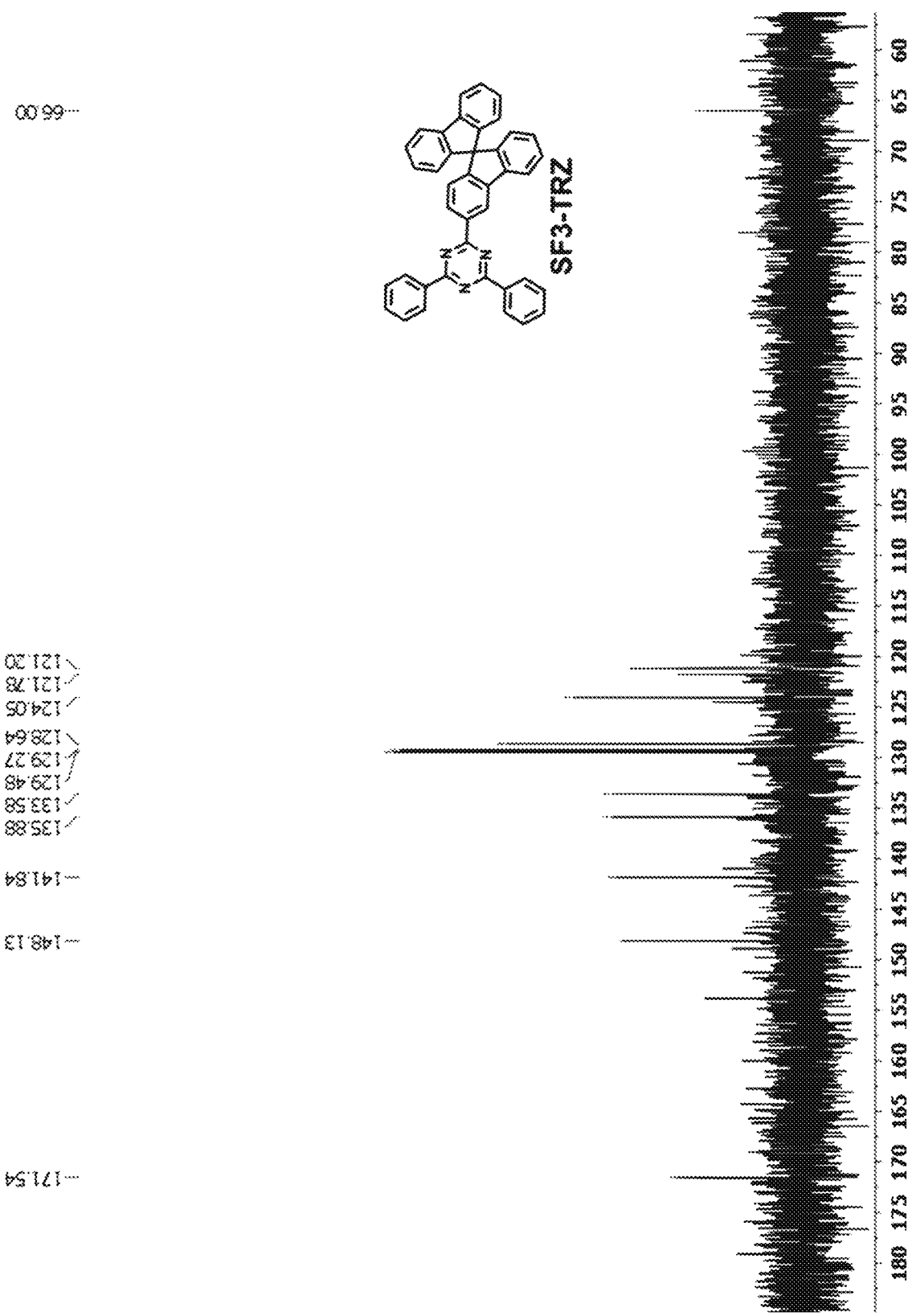

[Fig. 25]
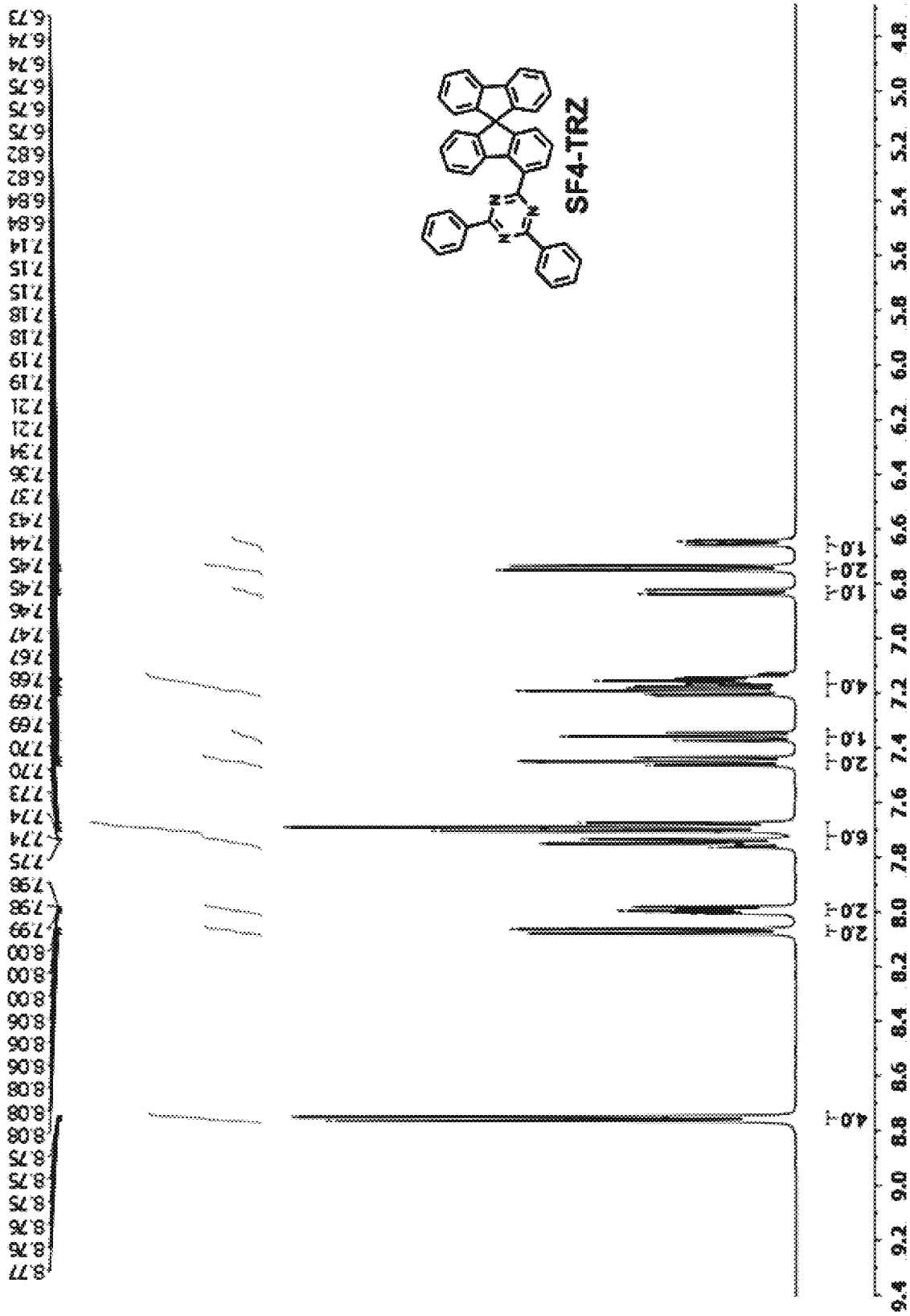

[Fig. 26]
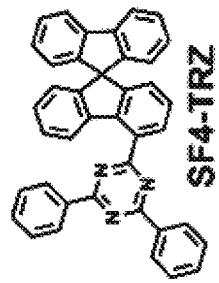
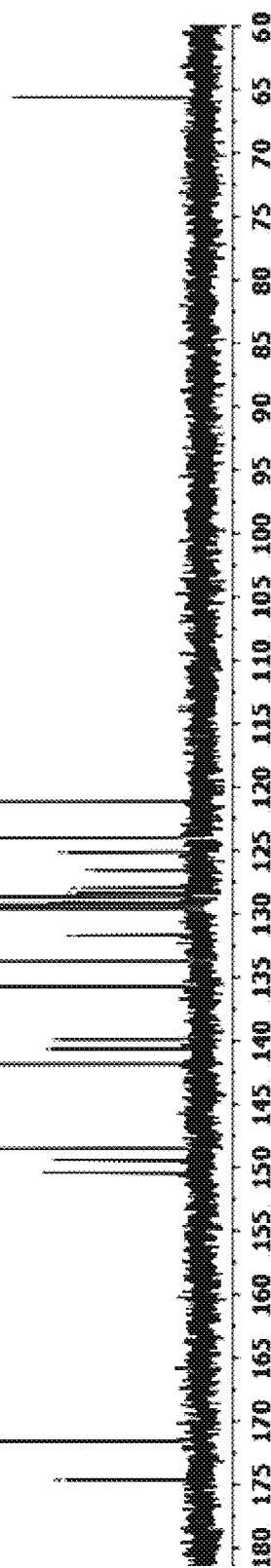

[Fig. 27]
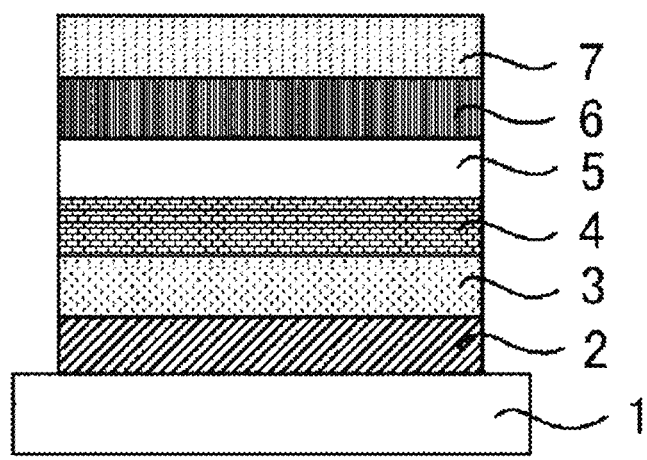

COMPOUND, LIGHT-EMITTING LIFETIME LENGTHENING AGENT, USE OF N-TYPE COMPOUND, FILM AND LIGHT-EMITTING DEVICE

TECHNICAL FIELD

The present invention relates to compounds, light-emitting lifetime lengthening agents, use of n-type compounds, films and light-emitting devices.

BACKGROUND ART

Thermally activated delayed fluorescence (TADF) emitters are promising as third-generation luminescent materials in organic light-emitting diodes (OLEDs).[1,2] Non-emissive triplet excitons ($T_1$) are readily up-converted into emissive singlet excitons ($S_1$) in TADF molecules because of their nearly degenerate $S_1$ and $T_1$ states, leading to 100% internal quantum efficiency.[3] As a result, TADF emitters have received considerable attention, and many efficient TADF molecules have been developed.[4-10] However, TADF technology still has some outstanding issues, such as the unsatisfactory stability of devices containing TADF emitters.

In a prototypical TADF OLED, holes and electrons are injected from opposing electrodes into transport and blocking layers and eventually recombine to form excitons within the emission layer (EML).[11] The EML typically consists of a host material with a wide energy gap doped with a TADF guest. This combination allows for efficient Forster and Dexter energy transfer from host to guest and confinement of both singlet and triplet excitons in the guest.[12,13] Host materials can usually be classified into three main categories in terms of their carrier behaviour: (1) hole transporting (p-type), (2) ambipolar, and (3) electron transporting (n-type).[14-16] However, regardless of which type of host is used, the triplet energy of the host should be higher than that of the TADF emitter to confine the singlet and triplet excitons.[17]

In addition to a wide energy gap, hosts also need appropriate highest occupied molecular orbital (HOMO) and lowest unoccupied molecular orbital (LUMO) levels not only to balance the electron and hole fluxes but also to control the exciton formation mechanism.[18-19] There are two possible exciton formation mechanisms in an EML. In one, excitons form on the host molecules and then transfer their energy to the TADF emitters via the Förster or Dexter mechanism. In the second, electrons and holes directly combine on the TADF emitters to directly form excitons.[20] However, the latter mechanism seems to be more beneficial than the former to improve the efficiency and stability of TADF OLEDs.[21] Direct exciton formation on the TADF molecules can eliminate energy dissipation channels and avoid the formation of high-energy exciton on host molecules.[22] This is important because high-energy excitons can break the chemical bonds of TADF molecules to induce device degradation.

One challenge is that organic semiconductors typically show highly asymmetric hole and electron mobilities, with the hole mobility exceeding the electron mobility by orders of magnitude in most cases.[23] Thus, holes usually greatly outnumber electrons in the EMLs. These excess holes cannot recombine with electrons to form excitons and have a negative effect on the operational reliability of OLEDs because of interactions between hole-polarons and high-energy excitons.[24,25] Good charge balance in organic semiconductors can be achieved by either increasing the electron mobility or decreasing the hole mobility. Over the last three decades, many researchers have attempted to improve electron drift mobility, but it still lags far behind hole mobility.[26,27]

Non-Patent Literatures

Non-Patent Literature 1: Uoyama, H. et al. Highly efficient organic light-emitting diodes from delayed fluorescence. *Nature* 492, 234-238 (2012).
Non-Patent Literature 2: Reineke, S. Organic light-emitting diodes: Phosphorescence meets its match. *Nat. Photonics*, 8, 269-270 (2014).
Non-Patent Literature 3: Etherington, M. K. et al. Revealing the spin-vibronic coupling mechanism of thermally activated delayed fluorescence. *Nat. Commun.* 7, 13680 (2016).
Non-Patent Literature 4: Di, D. et al. High-performance light-emitting diodes based on carbene-metal-amides. *Science* DOI: DOI: 10.1126/science.aah4345 (2017).
Non-Patent Literature 5: Lin, T.-A. et al. Sky—Blue Organic Light Emitting Diode with 37% External Quantum Efficiency Using Thermally Activated Delayed Fluorescence from Spiroacridine-Triazine Hybrid. *Adv. Mater* 28, 6976-6983 (2016).
Non-Patent Literature 6: Tsujimoto, H. et al. Thermally Activated Delayed Fluorescence and Aggregation Induced Emission with Through-Space Charge Transfer. *J. Am. Chem. Soc.* 139, 4894-4900 (2017).
Non-Patent Literature 7: Wong, M. Y. & Zysman—Colman, E. Purely Organic Thermally Activated Delayed Fluorescence Materials for Organic Light-Emitting Diodes. *Adv. Mater DOI:* 10.1002/adma.201605444 (2017).
Non-Patent Literature 8: Cui, L.-S. et al. Controlling Singlet-Triplet Energy Splitting for Deep-Blue Thermally Activated Delayed Fluorescence Emitters. *Angew. Chem. Int. Ed.* 129, 1593-1597 (2017).
Non-Patent Literature 9: Gómez-Bombarelli, R. et al. Design of efficient molecular organic light-emitting diodes by a high-throughput virtual screening and experimental approach. *Nat. Mater* 15, 1120-1127 (2016)
Non-Patent Literature 10: Zhang, Q. et al. Efficient blue organic light-emitting diodes employing thermally activated delayed fluorescence. *Nat. Photonics*, 8, 326-332 (2014).
Non-Patent Literature 11: Tang, C. W. & VanSlyke, S. A. Organic electroluminescent diodes. *Appl. Phys. Lett.* 51, 913-915 (1987).
Non-Patent Literature 12: Jankus, V, et al. Highly efficient TADF OLEDs: How the emitter-host interaction controls both the excited state species and electrical properties of the devices to achieve near 100% triplet harvesting and high efficiency. *Adv. Funct. Mater:* 24, 6178-6186, (2014).
Non-Patent Literature 13: Holmes, R. J. et al. Blue organic electrophosphorescence using exothermic host-guest energy transfer. *Appl. Phys. Lett.* 82, 2422-2424 (2003).
Non-Patent Literature 14: Duan, L., Qiao, J., Sun, Y. & Qiu, Y. Strategies to Design Bipolar Small Molecules for OLEDs: Donor-Acceptor Structure and Non-Donor-Acceptor Structure. *Adv. Mater:* 23, 1137-1144 (2011).
Non-Patent Literature 15: Chaskar, A., Chen, H. F. & Wong, K. T. Bipolar host materials: a chemical approach for highly efficient electrophosphorescent devices. *Adv. Mater:* 23, 3876-3895 (2011).
Non-Patent Literature 16: Han, T. H. et al. Ultrahigh-efficiency solution-processed simplified small-molecule organic light-emitting diodes using universal host materials. *Sci. Adv.* 2, e1601428 (2016).

Non-Patent Literature 17: Cui, L.-S., Kim, J. U., Nomura, H., Nakanotani, H. & Adachi, C. Benzimidazobenzothiazole-Based Bipolar Hosts to Harvest Nearly All of the Excitons from Blue Delayed Fluorescence and Phosphorescent Organic Light-Emitting Diodes. *Angew. Chem. Int. Ed.* 55, 6864-6868 (2016).

Non-Patent Literature 18: May, F et al. Design rules for charge-transport efficient host materials for phosphorescent organic light-emitting diodes. *J. Am. Chem. Soc.* 134, 13818-13822(2012).

Non-Patent Literature 19: Kim, D., Coropceanu, V. & Brédas, J.-L. Design of efficient ambipolar host materials for organic blue electrophosphorescence: theoretical characterization of hosts based on carbazole derivatives. *J. Am. Chem. Soc.* 133, 17895-17900 (2011).

Non-Patent Literature 20: Holmes, R. J. et al. Efficient, deep-blue organic electrophosphorescence by guest charge trapping. *Appl. Phys. Lett.* 83, 3818-3820 (2003).

Non-Patent Literature 21: Wu, C., Djurovich, P. I. & Thompson. M. E. Study of Energy Transfer and Triplet Exciton Diffusion in Hole-Transporting Host Materials. *Adv. Funct. Mater* 19, 3157-3164 (2009).

Non-Patent Literature 22: Zhang, Y., Lee, J. & Forrest. S. R. Tenfold increase in the lifetime of blue phosphorescent organic light-emitting diodes. *Nat. Commun.* 5, 5008 (2014).

Non-Patent Literature 23: Malliaras, G. G & Scott, J. C. The roles of injection and mobility in organic light emitting diodes. *J. Appl. Phys.* 83, 5399-5403(1998).

Non-Patent Literature 24: Cui, L.-S. et al. Controlling Synergistic Oxidation Processes for Efficient and Stable Blue Thermally Activated Delayed Fluorescence Devices. *Adv. Mater* 28, 7620-7625 (2016).

Non-Patent Literature 25: Giebink, N., DAndrade, B., Weaver, M., Brown, J. & Forrest, S. Direct evidence for degradation of polaron excited states in organic light emitting diodes. *J. Appl. Phys.* 105, 124514 (2009).

Non-Patent Literature 26: Kulkami, A. P., Tonzola, C. J., Babel, A. & Jenekhe, S. A. Electron transport materials for organic light-emitting diodes. *Chem. Mater:* 16, 4556-4573 (2004).

Non-Patent Literature 27: Abbaszadeh, D. et al. Elimination of charge carrier trapping in diluted semiconductors. *Nat. Mater* 15, 628-633 (2016).

Non-Patent Literature 28: Zhang, D. et al. High-Efficiency Fluorescent Organic Light-Emitting Devices Using Sensitizing Hosts with a Small Singlet-Triplet Exchange Energy. *Adv. Mater* 26, 5050-5055 (2014).

Non-Patent Literature 29: Nakanotani, H. et al. Promising operational stability of high-efficiency organic light-emitting diodes based on thermally activated delayed fluorescence. *Sci. Rep.* 3, 2127(2013).

Non-Patent Literature 30: Poriel, C. and Rault-Berthelot, J. Structure-Properties Relationship of 4-Substituted-Spirobifluorenes as Hosts for Phosphorescent Organic Light Emitting Diodes: An overview. *J. Mater Chem. C,* 5, 3869-3897 (2017).

Non-Patent Literature 31: Zhang, D. et al. Sterically shielded blue thermally activated delayed fluorescence emitters with improved efficiency and stability. *Mater Horiz.* 3, 145-151 (2016).

Non-Patent Literature 32: Hirata, S. et al. Highly efficient blue electroluminescence based on thermally activated delayed fluorescence. *Nat. Mater.* 14, 330-336 (2015).

Non-Patent Literature 33: Cui, L.-S. et al. Pure Hydrocarbon Hosts for≈100% Exciton Harvesting in Both Phosphorescent and Fluorescent Light-Emitting Devices. *Adv. Mater.* 27, 4213-4217 (2015).

Non-Patent Literature 34: Zhang, Q. et al. Efficient blue organic light-emitting diodes employing thermally activated delayed fluorescence. *Nat. Photonics,* 8, 326-332 (2014).

Non-Patent Literature 35: Uoyama, H. et al. Highly efficient organic light-emitting diodes from delayed fluorescence. *Nature* 492, 234-238 (2012).

Non-Patent Literature 36: Zhang, Y., Lee, J. & Forrest. S. R. Tenfold increase in the lifetime of blue phosphorescent organic light-emitting diodes. *Nat. Commun.* 5, 5008 (2014).

SUMMARY OF INVENTION

Organic light-emitting diodes (OLEDs) have become a mainstream display technology because of their desirable features. Third-generation OLEDs that use a new light-emitting mechanism called thermally activated delayed fluorescence (TADF) are currently garnering much attention. However, unsatisfactory device stability is still an unresolved issue in this field. Here we demonstrate that n-type hosts that have the intrinsic ability to balance the charge fluxes and broaden the recombination zone in TADF OLEDs while at the same time preventing the formation of high-energy exciton. The n-type hosts lengthen the lifetimes of green and blue TADF OLEDs by more than 30 and 1,000 times, respectively. Our results indicate that n-type hosts are suitable to realize stable TADF OLEDs.

We also provide the following inventions:

[1] A compound having a triazine ring substituted by a spiro aromatic group.

[2] The compound according to [1], wherein the spiro aromatic group is a spirofluorenyl group.

[3] The compound according to [1] or [2], wherein the triazine ring is further substituted by two aromatic groups.

[4] The compound according to [1], which is represented by the following formula (1):

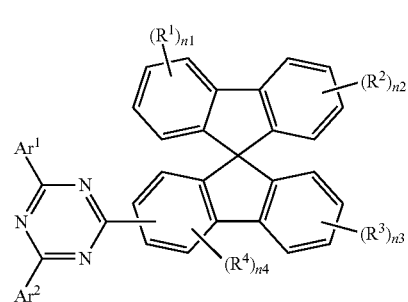

Formula (1)

wherein $Ar^1$ and $Ar^2$ each independently represent a substituted or unsubstituted aromatic group, $R^1$ to $R^4$ each independently represent a substituent, n1 to n3 are each independently an integer of from 1 to 4, and n4 is an integer of from 0 to 3.

[5] The compound according to [4], wherein $Ar^1$ and $Ar^2$ are each independently a substituted or unsubstituted phenyl group.

[6] The compound according to [4] or [5], wherein $Ar^1$ and $Ar^2$ are each independently a phenyl group which may be substituted by an alkyl group, an aryl group, a heteroaryl group, an alkoxy group, an aryloxy group or a heteroaryl group; preferably an alkyl group having 1-20 carbon atoms, an aryl group having 6-40 carbon atoms, a heteroaryl group having 3-40 carbon atoms, an alkoxy group having 1-20 carbon atoms, an aryloxy group having 6-40 carbon atoms, or a heteroaryloxy group having 3-40 carbon atoms; more preferably an alkyl group having 1-10 carbon atoms, an aryl group having 6-20 carbon atoms, a heteroaryl group having 3-20 carbon atoms, an alkoxy group having 1-10 carbon atoms, an aryloxy group having 6-20 carbon atoms, or a heteroaryloxy group having 3-20 carbon atoms; still more preferably an alkyl group having 1-6 carbon atoms, or an alkoxy group having 1-6 carbon atoms.

[7] The compound according to any one of [4] to [6], wherein $R^1$ to $R^4$ are each independently a phenyl group which may be substituted by an alkyl group, an aryl group, a heteroaryl group, an alkoxy group, an aryloxy group or a heteroaryl group; preferably an alkyl group having 1-20 carbon atoms, an aryl group having 6-40 carbon atoms, a heteroaryl group having 3-40 carbon atoms, an alkoxy group having 1-20 carbon atoms, an aryloxy group having 6-40 carbon atoms, or a heteroaryloxy group having 3-40 carbon atoms; more preferably an alkyl group having 1-10 carbon atoms, an aryl group having 6-20 carbon atoms, a heteroaryl group having 3-20 carbon atoms, an alkoxy group having 1-10 carbon atoms, an aryloxy group having 6-20 carbon atoms, or a heteroaryloxy group having 3-20 carbon atoms; still more preferably an alkyl group having 1-6 carbon atoms, or an alkoxy group having 1-6 carbon atoms.

[8] The compound according to any one of [1] to [7], wherein the spirofluorenyl group is bonded to the triazine ring at 2-position of the spirofluorene.

[9] The compound according to any one of [1] to [7], wherein the spirofluorenyl group is bonded to the triazine ring at 3-position of the spirofluorene.

[10] The compound according to any one of [1] to [7], wherein the spirofluorenyl group is bonded to the triazine ring at 4-position of the spirofluorene.

[11] A light-emitting lifetime lengthening agent containing an n-type compound.

[12] The light-emitting lifetime lengthening agent according to [11], wherein the n-type compound is the compound of any one of [1] to [10].

[13] The light-emitting lifetime lengthening agent according to [11] or [12], which is used for lengthening light-emitting lifetime of a light-emitting device containing an emitter having a HOMO level of −5.75 eV or less.

[14] The light-emitting lifetime lengthening agent according to [11] or [12], which is used for lengthening light-emitting lifetime of a light-emitting device containing a delayed fluorescence emitter.

[15] The light-emitting lifetime lengthening agent according to [11] or [12], which is used for lengthening light-emitting lifetime of a light-emitting device containing a thermally activated delayed fluorescence emitter.

[16] The light-emitting lifetime lengthening agent according to any one of [11] to [15], which is used for lengthening light-emitting lifetime of a light-emitting device containing a compound having a $\Delta E_{ST}$ of 0.3 eV or less.

[17] Use of an n-type compound as a host material for a delayed fluorescence emitter.

[18] Use of the compound of any one of [1] to [10] as a host material for a delayed fluorescence emitter.

[19] Use of an n-type compound as a host material for a compound having a $\Delta E_{ST}$ of 0.3 eV or less.

[20] Use of the compound of any one of [1] to [10] as a host material for a compound having a $\Delta E_{ST}$ of 0.3 eV or less.

[21] A film containing an n-type compound and a delayed fluorescence emitter.

[22] A film containing an n-type compound and a compound having a $\Delta E_{ST}$ of 0.3 eV or less.

[23] The film according to [22], further containing an emitter.

[24] The film according to any one of [21] to [23], wherein the n-type compound is the compound of any one of [1] to [10].

[25] The film according to any one of [21] to [23] wherein the delayed fluorescence emitter or the compound having a $\Delta E_{ST}$ of 0.3 eV or less has a benzene ring substituted with at least one cyano group and at least one electron-donating group.

[26] The film according to [25], wherein the delayed fluorescence emitter or the compound having a $\Delta E_{ST}$ of 0.3 eV or less has a benzene ring substituted with at least one cyano group and at least one diarylamino group.

[27] The film according to [26], wherein the two aryl groups of the diarylamino group are bonded to each other to form a ring.

[28] The film according to any one of [21] to [27], which can emit a light by injection of holes and electrons from opposing surfaces of the film.

[29] The film according to any one of [21] to [27], which can emit a light by irradiation of an excitation light.

[30] A light-emitting device having the film of any one of [21] to [29] as a light-emitting layer.

[31] The light-emitting device according to [30], wherein the n-type compound is also contained in a layer which is in contact with a light-emitting layer.

[32] The light-emitting device according to [30] or [31], which is an organic electroluminescence device.

[33] The light-emitting device according to any one of [30] to [32], which emits a delayed fluorescent light.

BRIEF DESCRIPTION OF DRAWINGS

FIG. 1A-FIG. 1E: Molecular structures and properties. FIG. 1A, Distribution of HOMO, LUMO and TSDD in SF3-TRZ. Optimized structures of the HOMO, LUMO and TSDD of SF3-TRZ were calculated by TD-DFT (Gaussian09/B3LYP/6-31G+(d)). FIG. 1B, Absorption and photoluminescence spectra (298 K) of spirobifluorene (SF), triazine (TRZ), SF2-TRZ, SF3-TRZ and SF4-TRZ in dilute toluene solution. FIG. 1C, Phosphorescent spectra of SF2-TRZ, SF3-TRZ, and SF4-TRZ in 2-methyltetrahydrofuran glass at 77 K. FIG. 1D, Hole and electron transport in an SF2-TRZ neat film. Hole and electron current density (J) versus applied voltage (V) in an SF2-TRZ neat film. FIG. 1E, Hole and electron transport in an SF4-TRZ neat film. Hole and electron J against V in an SF4-TRZ neat film.

FIG. 2A and FIG. 2B: Structures of red, green and blue TADF OLEDs. FIG. 2A, Chemical structures of the TADF emitters used in the emitting layers (EMLs) of TADF OLEDs. FIG. 2B, Structures of TADF OLEDs.

FIG. 3A-FIG. 3D: Performance characteristics of red, green and blue TADF OLEDs. FIG. 3A, EQE, current efficiency (CE) and power efficiency (PE) versus luminance of devices G1, G2 and G3. FIG. 3A, EQE, CE and PE versus luminance of devices R1, B1 and B2. FIG. 3C, Electroluminescence (EL) spectra of device G2, R1 and B1 measured at a current density J of 10 mA/cm². FIG. 3D, Operational lifetime of the red, green and blue TADF OLEDs. The initial luminance of the green (G1-3), red (R1) and blue (B1 and 2)

devices was 5,000, 2,000 and 1,000 cd/m², respectively. The control device with mCBP as a host was operated at an initial luminance of 5,000 cd/m².

FIG. 4A and FIG. 4B: Hole and electron transport of host and TADF emitter-doped host films. FIG. 4A, Hole and electron current density J versus applied voltage V in an SF3-TRZ neat film and 15 wt % 4CzIPN-doped SF3-TRZ film. FIG. 4B, Hole and electron J versus V in an mCBP neat film and 15 wt % 4CzIPN-doped mCBP film.

FIG. 5: Calculated spatial distributions of HOMO, LUMO and triplet spin density (TSDD) of SF2-TRZ, SF3-TRZ, and SF4-TRZ.

FIG. 6: UV-Vis absorption spectra and PL emission spectra of SF2-TRZ, SF3-TRZ, and SF4-TRZ in neat film states.

FIG. 7: Photoelectron spectral measurement of SF2-TRZ neat film under nitrogen atmosphere.

FIG. 8: Photoelectron spectral measurement of SF3-TRZ neat film under nitrogen atmosphere.

FIG. 9: Photoelectron spectral measurement of SF4-TRZ neat film under nitrogen atmosphere.

FIG. 10A and FIG. 10B: FIG. 10A TGA thermograms of compounds SF2-TRZ, SF3-TRZ, and SF4-TRZ. The temperatures shown in the figure correspond to the 5% weight loss. FIG. 10B DSC thermograms of SF2-TRZ, SF3-TRZ, and SF4-TRZ.

FIG. 11: Electron mobility plotted with respect to E1/2 for SF3-TRZ.

FIG. 12: Energy levels of the materials employed in the devices.

FIG. 13: J-V curves for the hole-only devices (ITO/HAT-CN (10 nm)/α-NPD (30 nm)/Tris-PCz (20 nm)/mCBP (10 nm)/mCBP: x wt % TADF (100 nm)/Tris-PCz (20 nm)/Al (100 nm), where x=0 or 15) and the electron-only devices (ITO/T2T (20 nm)/mCBP: x wt % TADF (100 nm)/T2T (10 nm)/Bebq$_2$ (35 nm)/LiF (0.8 nm)/Al (120 nm), where x=0 or 15).

FIG. 14: J-V curves for the hole-only devices (ITO/HAT-CN (10 nm)/α-NPD (30 nm)/Tris-PCz (20 nm)/mCBP (10 nm)/SF3-TRZ: x wt % TADF (100 nm)/Tris-PCz (20 nm)/Al (100 nm), where x=0 or 15) and the electron-only devices (ITO/SF3-TRZ (20 nm)/SF3-TRZ: x wt % TADF (100 nm)/SF3-TRZ (10 nm)/Bebq$_2$ (35 nm)/LiF (0.8 nm)/Al (120 nm), where x=0 or 15).

FIG. 15: The EL spectrum at 10 mA/cm² for the device G1, G2 and G3.

FIG. 16: EQE versus luminance curve of mCBP-based device.

FIG. 17: J-V curves of device G1, G2, G3 and mCBP-based device.

FIG. 18: J-V curves of device R1, B2 and B3.

FIG. 19: Changes in voltage of the devices G1, G2, G3 and mCBP-based device versus operational time during which the devices driven at an initial luminescence of 5,000 cd/cm².

FIG. 20: Changes in voltage of the devices R1, B1 and B2 versus operational time during which the devices R1, B1 and B2 driven at an initial luminescence of 2,000 cd/cm², 1,000 cd/cm² and 1,000 cd/cm², respectively.

FIG. 21: $^1$H NMR spectrum of SF2-TRZ.
FIG. 22: $^{13}$C NMR spectrum of SF2-TRZ.
FIG. 23: $^1$H NMR spectrum of SF3-TRZ.
FIG. 24: $^{13}$C NMR spectrum of SF3-TRZ.
FIG. 25: $^1$H NMR spectrum of SF4-TRZ.
FIG. 26: $^{13}$C NMR spectrum of SF4-TRZ.

FIG. 27: Schematic cross sectional view showing an example of a layer structure of an organic electroluminescence device.

DETAILED DESCRIPTION OF INVENTION

The invention is described in detail hereinunder. The constitutional elements may be described below with reference to representative embodiments and specific examples of the invention, but the invention is not limited to the embodiments and the examples. In this description, the numerical range expressed by the wording "a number to another number" means the range that falls between the former number indicating the lower limit of the range and the latter number indicating the upper limit thereof. In the invention, the hydrogen atom that is present in the molecule of the compound used in the invention is not particularly limited in isotope species, and for example, all the hydrogen atoms in the molecule may be $^1$H, and all or a part of them may be $^2$H (deuterium D).

Most TADF molecules consist of p-type (donor) and n-type (acceptor) moieties, leading to bipolar transport properties.[28] Unlike some stable fluorescent and phosphorescent emitters, the HOMO levels of TADF molecules are normally lower than −5.80 eV because of intrinsic properties of the emitters (Table 3). Undoubtedly, the orbital energy levels of TADF emitters and host materials are critical for hole and electron transport channels in EMLs.[29] To realize charge balance and avoid high-energy exciton formation in EMLs, the ideal charge transport mode is hole transport on the TADF molecules and electron transport via the host molecules. To ensure that holes tend to be transported on the TADF molecules, the HOMO levels of the host molecules should be much deeper than those of the TADF molecules. Thus, we reasoned that n-type hosts are the preferred option for TADF emitters to improve both device efficiency and operational stability.

To validate this hypothesis, we designed and synthesized three simple n-type hosts. Single-carrier current-voltage (V) measurements clearly demonstrate that the hole and electron mobilities of these n-type hosts strongly depend on the TADF guest molecules. Such tuneable charge-carrier mobilities allow us to balance the hole and electron fluxes, broaden the exciton distribution and suppress the formation of high-energy exciton in EMLs. Through this strategy, we lengthen the lifetime of TADF OLEDs by more than 30 times, revealing the possibility to achieve efficient and stable TADF OLEDs.

Results

Characterization of n-Type Hosts

The syntheses of our new n-type hosts SF2-TRZ, SF3-TRZ and SF4-TRZ are described below. The three n-type hosts exhibit good thermal stability with clear glass transition temperatures above 130° C. (FIG. 10a), and the decomposition temperatures at 5% loss are estimated to be nearly 400° C. (FIG. 10b). The HOMOs of these isomers are located on the spirobifluorene (SF) group, whereas their LUMOs have slightly different distributions (FIG. 5). Because of the large dihedral angle between the SF planes and triazine (TRZ) plane (36.3°) in an SF4-TRZ molecule, the LUMO of SF4-TRZ is only localized on the TRZ group and peripheral phenyl rings. Conversely, the dihedral angles completely vanished in SF2-TRZ and SF3-TRZ, and the LUMOs of both SF2-TRZ and SF3-TRZ spread over not only the TRZ group but also the SF unit. Spatially separated HOMOs and LUMOs are beneficial for intramolecular charge transfer. The triplet spin density distributions (TSDDs) of these isomers were simulated to estimate their T₁ excited state locations. The TSDDs of SF2-TRZ and SF4-TRZ are mainly delocalized over SF and TRZ units, while that of SF3-TRZ is localized on the TRZ unit, suggesting a higher $T_1$ for SF3-TRZ (FIG. 1a).

FIG. 1b depicts the ultraviolet-visible (UV-vis) absorption and photoluminescence (PL) spectra of the three n-type hosts. The hosts present analogous absorption bands in the range of 304-315 nm with maxima at 309 nm, similar to the main absorption band of SF, which is attributed to characteristic π-π* transitions of the fluorene fragment in SF. SF2-TRZ displays a strong absorption band at 326-370 nm, which is attributed to the extension of the I-conjugation length between the C2-substituted SF and TRZ units. Conversely, SF3-TRZ and SF4-TRZ show weaker absorption between 323 and 360 nm. This can be attributed to disruption of I-conjugation induced by the meta-linking mode and large torsion angle in SF3-TRZ and SF4-TRZ, respectively.

The PL spectra of the three analogues strongly depend on their substitution positions. SF2-TRZ exhibits a well-resolved emission spectrum ($\lambda_{max}$=403/417 nm) that is a mirror image of its absorption spectrum. Conversely, SF3-TRZ and SF4-TRZ show structureless emission spectra with peaks at 412 and 448 nm, respectively. This indicates that SF3-TRZ and SF4-TRZ display charge transfer (¹CT) characteristics in their $S_1$ states, whereas the $S_1$ state of SF2-TRZ is identified as a localized state (¹LE). These differences are well explained by the distributions of their frontier molecular orbitals (FIG. 5). In addition, the emission peak of SF4-TRZ is red-shifted by approximately 36 nm compared with that of SF3-TRZ. This is because the $S_1$ state of SF4-TRZ undergoes substantial rigidification, such as a planarization of the structure, with the TRZ substituent conjugated to the SF core.[30] Thus, a bathochromic shift of emission and large Stokes shift are clearly observed for SF4-TRZ.

The solid-state UV-vis absorption and PL spectra of the three hosts (FIG. 6) closely resemble those in solution state. This indicates that intermolecular interactions of these compounds are efficiently suppressed in their amorphous states because of their orthogonal molecular structures. The HOMO energy levels of SF2-TRZ, SF3-TRZ and SF4-TRZ thin films were determined to be −6.56 eV, −6.54 eV and −6.55 eV, respectively, using an AC-3 ultraviolet photoelectron spectrometer (FIGS. 7-9). The LUMO energy levels of SF2-TRZ, SF3-TRZ, and SF4-TRZ were estimated to be −3.27 eV, −3.10 eV and −3.23 eV, respectively, by adding the optical energy gaps determined from the absorption edges of thin films to the HOMO energy levels. The $T_1$ of SF2-TRZ, SF3-TRZ, and SF4-TRZ were determined to be 2.53, 2.80 and 2.65 eV, respectively, from the highest energy vibronic peak of their phosphorescent (Phos) spectra in 2-methyltetrahydrofuran (2-MeTHF) at 77 K (FIG. 1c). The high $T_1$ of SF3-TRZ makes it promising as a host for blue TADF emitters.

To evaluate the carrier transport properties of the n-type hosts, hole-only devices (HODs) and electron-only devices (EODs) with structures of indium tin oxide (ITO)/MoO₃ (1 nm)/host (100 nm)/MoO₃ (10 nm)/Al (100 nm) and ITO/Cs (10 nm)/host (100 nm)/Cs (10 nm)/Al (100 nm), respectively, were fabricated. The current density (J-V) characteristics of the devices (FIGS. 1d and 1e) show two distinct regions at low and high bias, which are assigned as the Schottky thermionic region and space-charge-limited current (SCLC) region, respectively. The SCLC can be expressed as, $$J = \frac{9}{8}\varepsilon\varepsilon_0\mu_0\exp\left(\beta\sqrt{\frac{V}{L}}\right)\frac{V^2}{L^3}, \quad (1)$$

where V is the applied voltage; $\mu_0$ is the zero-field charge mobility; ε and $\varepsilon_0$ are the relative dielectric constant and free-space permittivity, respectively; L is the thickness of the host material and β is the Poole-Frenkel factor. Within this model, the mobility is expressed as $$\mu = \mu_0\exp\left(\beta\sqrt{\frac{V}{L}}\right). \quad (2)$$

The estimated zero-field hole and electron mobilities ($\mu_{0h}$ and $\mu_{0e}$, respectively) of these n-type hosts are around 7-11×10⁻⁹ and 2-6×10⁻⁵ cm²/Vs. The detailed data are summarized in Tables 5 and 6. The results are in good agreement with the mobilities measured by the conventional time-of-flight method (FIG. 11).

TADF OLED Performance

We examined the electroluminescence (EL) properties of these n-type hosts in devices with the structure of ITO/HAT-CN (10 nm)/α-NPD (30 nm)/Tris-PCz (20 nm)/mCBP (10 nm)/EML (30 nm)/host (10 nm)/Bebq₂ (35 nm)/LiF (0.8 nm)/Al (120 nm), where HAT-CN, α-NPD, Tris-PCz, mCBP and Bebq₂ are 1,4,5,8,9,11-hexaazatriphenylene hexacarbonitrile, N,N'-diphenyl-N,N'-bis(1-naphthyl)-1,10-biphenyl-4,4'-diamine, 9,9',9"-triphenyl-9H,9'H,9"H-3,3':6'3"-tercarbazole, 3,3-di(9H-carbazol-9-yl)biphenyl and bis(10-hydroxybenzo[h]quinolinato)beryllium, respectively. EMLs consisting of the common TADF emitter 1,2,3,5-tetrakis (carbazol-9-yl)-4,6-dicyanobenzene (4CzIPN) doped in SF2-TRZ, SF3-TRZ and SF4-TRZ with the optimized doping concentration of 15 wt % were used in devices G1, G2 and G3, respectively, while the EML of device R1 consisted of 10 wt % 2,6-bis(4-(diphenylamino)phenyl)anthracene-9, 10-dione (DPA-AQ) doped in SF3-TRZ (FIGS. 2A and 2B). For comparison, a control device with the conventional p-type material mCBP as host was constructed.

As illustrated in FIG. 3a, high and stable efficiencies were achieved in devices G1, G2 and G3. The maximum efficiencies of device G2 were as high as 20.6% for external quantum efficiency (EQE), 68.3 cd/A for current efficiency (CE), and 61.3 lm/W for the power efficiency (PE). Device G3 exhibited moderate maximum efficiencies of 18.3% for EQE, 60.6 cd/A for CE, and 54.3 lm/W for PE. The efficiency of device G1 was lower than those of device G2 and G3, with maximum efficiencies being 14.5% for EQE, 50.1 cd/A for CE, and 45.0 lm/W for PE. The difference between the EQE values of devices G1, G2 and G3 is consistent with the trend of the PL quantum yields of 4CzIPN doped in these n-type hosts, which was determined by their $T_1$ energies (Table 4). In addition, all three devices exhibited lower efficiency roll-off at higher luminance compared to that of the mCBP-based device.

We define the critical luminance ($L_{90}$) as the luminance at which the EQE decreases to 90% of its maximum value. A higher $L_{90}$ indicates lower roll-off in an OLED. The $L_{90}$ values of the SF-TRZ-based devices are as high as 3,000 cd/m², and much higher than that of the mCBP-based device (1,700 cd/m², FIG. 16). This can be ascribed to the wellbalanced electron/hole transport in the EMLs of device G1, G2 and G3 with n-type hosts, as described in detail in the following section.

The operational stability of the devices was also evaluated (FIG. 3d). The devices with the n-type hosts displayed long-term operational stability, with device lifetime extended more than 30 times compared to that of the device with a p-type host. FIG. 6 reveals that the half-lives ($T_{50}$) of devices G1, G2 and G3 are 565, 654 and 329 h at an initial brightness of 5,000 cd/m². The relatively short lifetime of device G3 may be caused by the weak bond dissociation energy between TRZ and SF moieties (bond C) in SF4-TRZ (Table 2). The lifetime of device G2 is predicted to be 10,934 h at 1,000 cd/m² according to the formula $LT(L_1)=LT(L_0)(L_0/L_1)^{1.75}$, where $L_1$ is the desired luminance of 1,000 cd/m².[31]

Device R1 with a red emitter exhibits a high EQE of 11.5% and $T_{50}$ of 594 h at an initial brightness of 2,000 cd/m² (FIGS. 3b and 3d). The high $T_1$ of SF3-TRZ allowed it to be used as a host for blue TADF emitters. The EMLs of devices B1 and B2 respectively consisted of 15 and 30 wt % 9-(4-(4,6-diphenyl-1,3,5-triazin-2-yl)phenyl)-9'-phenyl-9H,9'H-3,3'-bicarbazole (BCz-TRZ) doped in SF3-TRZ. The EL spectra of devices G1, R1, and B1 are depicted in FIG. 3c. The maximum EQEs of device B1 and B2 were 11.0% and 8.8%, respectively (FIG. 3b). Importantly, the lifetime of device B1 was longer than that of device B2, with these devices displaying $T_{50}$ of 137 and 454 h, respectively, at an initial brightness of 1,000 cd/m² (FIG. 3d). These values are amongst the longest reported for TADF OLEDs with such simple device architectures.

Hole-Only and Electron-Only Devices

To investigate the charge transport and exciton recombination zone in the EMLs, HODs and EODs with 15 wt % 4CzIPN-doped n- and p-type hosts, respectively, were fabricated. FIGS. 4A and 4B present the J-V characteristics of HODs and EODs with 15 wt % 4CzIPN-doped SF3-TRZ and mCBP layers. According to equation (1), doping 4CzIPN into SF3-TRZ leads to a more than thirtyfold increase in $\mu_{h0}$ of SF3-TRZ, whereas $\mu_{e0}$ of 4CzIPN-doped SF3-TRZ was nearly two orders of magnitude lower than that of SF3-TRZ. Therefore, the difference between the hole and electron mobilities of 4CzIPN-doped SF3-TRZ is relatively small. Conversely, $\mu_{h0}$ of 4CzIPN-doped mCBP is about ten times lower than that of neat mCBP. Because its electron density was too low, $\mu_{e0}$ of a neat mCBP film could not be measured. However, the estimated $\mu_{e0}$ of the 4CzIPN-doped mCBP film was about $1.0\times10^{-10}$ cm²/Vs. We believe that the electron mobility of mCBP should be increased by doping with 4CzIPN.

The difference between the hole and electron mobilities of 4CzIPN-doped mCBP is much larger than that of 4CzIPN-doped SF3-TRZ. Detailed data for the charge drift mobilities are listed in Table 6. Thus, we infer that use of n-type hosts in TADF OLEDs is greatly beneficial to balance the charge fluxes and subsequently broaden the recombination zone, avoid excessive charge and exciton accumulation, and lower leakage current in the devices. The negative effects on device stability induced by charge and exciton accumulation should be suppressed by using n-type hosts in TADF OLEDs. We further verified our hypothesis by fabricating HODs and EODs based on our EL device architectures. The differences between J of the HODs and EODs based on n-type host SF3-TRZ are much smaller than those of ones based on p-type host mCBP at the same voltage (FIGS. 13 and 14).

Discussion

Our observations can be well explained from the perspective of the different hole and electron transport channels in the EMLs caused by the difference between the orbital energy levels of host molecules and TADF emitters. TADF materials typically possess both hole and electron transport properties because of their intrinsic molecular structures. The HOMO levels of TADF emitters are usually deeper than those of fluorescent and phosphorescent emitters. For example, the HOMO level of 4CzIPN is −5.80 eV, which is close to that of p-type host mCBP. Thus, holes tend to be transported on host molecules in a 4CzIPN-doped mCBP film. Although the electron mobility of mCBP can be improved by doping, electron transport is difficult to balance with hole transport because of their intrinsic asymmetry. In contrast, holes tend to be transported on TADF molecules in a 4CzIPN-doped SF3-TRZ film because of the deep HOMO level of the n-type host. This approach can increase the hole mobilities of n-type hosts, although TADF molecules do simultaneously lower the electron mobilities of n-type hosts through the dilution effect. Overall, the difference between the hole and electron mobilities of n-type host-based EMLs is much smaller than that of EMLs with a p-type host, indicating superior charge-carrier balance and a broad recombination zone in EMLs with an n-type host. In addition, the orbital levels of n-type hosts usually encourage exciton formation on TADF molecules, which can suppress high-energy exciton formation on host molecules and further extend device lifetime. These advantages are the most important reasons why n-type hosts are beneficial to improve the stability of TADF devices. However, the electron mobilities of EMLs based on p-type hosts are much lower than their hole mobilities. Therefore, hole and electron fluxes are unbalanced, resulting in exciton accumulation at the interface of the EML. Above all, n-type hosts are proved to be the best choice for TADF OLEDs.

CONCLUSIONS

TADF molecules usually consist of donor and acceptor moieties, and the acceptor unit determines the HOMO level of a TADF emitter, which is typically deeper than −5.80 eV. This situation is quite different from that of the emitters in some stable fluorescent and phosphorescent OLEDs. Thus, efficient and stable TADF OLEDs require strict criteria regarding host selection to match with TADF emitters. Fortunately, n-type hosts possess inherent advantages to balance charge fluxes and suppress high-energy exciton formation because of their deep HOMO levels and excellent electron transport properties. Here we demonstrated a thirtyfold increase in the lifetime of TADF OLEDs upon using n-type hosts. Green TADF OLEDs with SF3-TRZ as the host achieved a maximum EQE of 20.6% and predicted $T_{50}$ of 10,934 h at an initial brightness of 1,000 cd/m². More importantly, SF3-TRZ can also function as a host for sky-blue TADF OLEDs because of its high $T_1$. A sky-blue TADF OLED with a high EQE of 8.8% and lifetime of 454 h at an initial brightness of 1,000 cd/m² was produced. The lifetime is three orders of magnitude higher than the mCBP-based device according to our previous report.[24] Although the lifetimes reported here lag behind the criteria for consumer electronics, further lifetime improvements should be achieved by finding the most suitable host/dopant combinations. Our work offers guidelines to realize long-lived and efficient TADF OLEDs.

Experimental Section
Materials and Methods

Unless otherwise noted, all chemicals and materials were purchased from Aldrich, Xi'an Polymer Light Technology Co. or Luminescence Technology Co. and used without additional purification. The molecular structures of the as-synthesized TADF molecules were fully characterized by NMR spectroscopy, mass spectrometry and elemental analysis.

All reagents were used as received from commercial sources and were used without further purification. 2-chloro-4,6-diphenyl-1,3,5-triazine, tetrakis(triphenylphosphine)platinum, potassium carbonate were purchased from TCI. Chromatographic separations were carried out using silica gel (200-300 nm). Spirobifluorene boracic acids were synthesized according to our previous reported procedures.[33] The three new hosts investigated in this paper were synthesized by following the procedures described below. Host materials SF2-TRZ, SF3-TRZ, and SF4-TRZ were purified by temperature gradient vacuum sublimation twice. $^1$H nuclear magnetic resonance (NMR) and $^{13}$C NMR spectra were obtained in dimethylsulfoxide-$d_6$ (DMSO-$d_6$) with a Bruker Biospin Avance-III 500 NMR spectrometer at ambient temperature. Chemical shifts (δ) are given in parts per million (ppm) relative to tetramethylsilane (TMS; δ=0) as the internal reference. Mass spectra were measured in positive-ion atmospheric-pressure chemical ionization (APCI) mode on a Waters 3100 mass detector. Elemental analyses (C, H and N) were carried out with a Yanaco MT-5 elemental analyzer. Toluene solutions containing the three hosts ($1\times10^{-6}$ mol/L) were prepared to investigate their absorption and photoluminescence characteristics in the solution state. Neat film samples were deposited on quartz glass substrates by vacuum evaporation to study their excitons confinement properties in the film state. Ultraviolet-visible absorption (UV-vis) and photoluminescence (PL) spectra were recorded on a Perkin-Elmer Lambda 950 KPA spectrophotometer and a JobinYvon FluoroMax-3 fluorospectrophotometer. Phosphorescent spectra were recorded on a JASCO FP-6500 fluorescence spectrophotometer at 77 K. Absolute PL quantum yields were measured on a Quantaurus-QY measurement system (C11347-11, Hamamatsu Photonics) under nitrogen flow and all samples were excited at 360 nm. The transient photoluminescence decay characteristics of film samples were recorded using a Quantaurus-Tau fluorescence lifetime measurement system (C11367-03, Hamamatsu Photonics). The prompt and delayed PL spectra of the samples were measured under vacuum using a streak camera system (Hamamatsu Photonics, C4334) equipped with a cryostat (Iwatani, GASESCRT-006-2000, Japan). A nitrogen gas laser (Lasertechnik Berlin, MNL200) with an excitation wavelength of 337 nm was used. The HOMO levels of neat films (100 nm) were measured by a Riken Keiki AC-3 photoelectron spectroscopy.

Quantum Chemical Calculations

All calculations were carried out using the Gaussian 09 program package. The geometries in the ground state were optimized via DFT calculations at the B3LYP/6-31+G(d) level. Calculations on the electronic triplet state of host molecules were also carried out employing DFT with the same basis sets. TD-DFT calculations for the S0→Sn and S0→T1 transitions using the B3LYP functional were then performed according to the geometry optimization in the lowest-lying singlet and triplet states, respectively. In addition, Mulliken population analysis was performed to characterize the spin density distributions (TSDDs) of unpaired electrons in the triplet state for SF2-TRZ, SF3-TRZ, and SF4-TRZ molecules. The blue and green colors represent α and β spin density distributions, respectively. The radius of the circles corresponds to the value of the TSDD on each atom. Bond dissociation energy (BDE) was calculated according to the enthalpy change in the corresponding reaction of homolytic cleavage of a single bond in the gas phase at 298 K and 1 atm. Calculations on the excited states energies of the molecules were carried out using time-dependent DFT (TD-DFT) theory at the level of B3LYP/6-31+G(d).

Device Fabrication and Measurements

The OLEDs were fabricated through vacuum deposition of the materials at ca. $3.0\times10^{-4}$ Pa onto ITO-coated glass substrates having a sheet resistance of ca. 15Ω per square. The ITO surface was cleaned ultrasonically-sequentially with acetone, ethanol, and deionized water, then dried in an oven, and finally exposed to UV-ozone for about 30 min. Organic layers were deposited at a rate of 2-3 Å/s, subsequently, LiF was deposited at 0.2 Å/s and then capped with Al (ca. 4 Å/s). The devices were exposed once to nitrogen gas after the formation of the organic layers because a metal mask was included to define the cathode area. For all the OLEDs, the emitting areas were determined by the overlap of two electrodes as 0.04 cm$^2$. The J-V-luminance characteristics were evaluated using a Keithley 2400 source meter and an absolute EQE measurement system (C9920-12, Hamamatsu Photonics, Japan).

Charge Carrier Transport Properties

The J-V characteristics show two distinct regions at low and high biases, such as Schottky thermionic region and SCLC region, respectively. As voltage increases, the J-V characteristics switch to the SCLC and the SCLC can be expressed as $$J = \frac{9}{8}\varepsilon\varepsilon_0\mu_0 \frac{V^2}{L^3}, \tag{1}$$

where V is the applied voltage, ε and ε₀ are the relative dielectric constant and the permittivity of the free space, respectively, and L is the thickness of the organic layer. The carrier mobility is affected by the energetic disorder due to the interaction of each hopping charge with randomly oriented and randomly located dipoles in the organic thin film. Therefore, the mobility is dependent on the electric field and can be expressed by a Poole-Frenkel PF equation, $$\mu = \mu_0 \exp\left(\beta\sqrt{\frac{V}{L}}\right), \tag{2}$$

where $\mu_0$ is the zero-field mobility and $\beta$ is Poole-Frenkel factor. From the combination of equations (1) and (2), the field dependent SCLC can be easily expressed by $$J = \frac{9}{8}\varepsilon\varepsilon_0\mu_0\exp\left(\beta\sqrt{\frac{V}{L}}\right)\frac{V^2}{L^3}. \quad (3)$$

The detailed data are summarized in Tables 5 and 6.

TABLE 1

Calculated HOMO, LUMO, Bandgap, S1, T1 values from DFT and TD-DFT at B3LYP/6-31g(d) level.

| Compound | HOMO (eV) | LUMO (eV) | Bandgap (eV) | $S_1$@$S_0$ (eV) | $T_1$@$S_0$ (eV) |
|---|---|---|---|---|---|
| SF-TRZ2 | −5.70 | −1.86 | 3.84 | 3.34 | 2.63 |
| SF-TRZ3 | −5.71 | −1.79 | 3.92 | 3.45 | 2.82 |
| SF-TRZ4 | −5.67 | −1.82 | 3.84 | 2.37 | 2.70 |

TABLE 2

Bond dissociation energies (BDE) in the SF2-TRZ, SF3-TRZ, and SF4-TRZ.

| Compound | Bond | Bond Dissociation Reaction | Average BDE (kcal/mol) |
|---|---|---|---|
| | a | SF2-TRZ •⁻ → SF2-TRZ • + Ph⁻ | 115.5 |
| | | SF2-TRZ •⁻ → SF2-TRZ⁻ + Ph• | 108.4 |
| | b | SF2-TRZ •⁻ → SF2-TRZ • + Ph⁻ | 115.8 |
| | | SF2-TRZ •⁻ → SF2-TRZ • + Ph⁻ | 105.4 |
| | c | SF2-TRZ •⁻ → SF• + TRZ⁻ | 106.5 |
| | | SF2-TRZ •⁻ → SF⁻ + TRZ• | 108.38 |

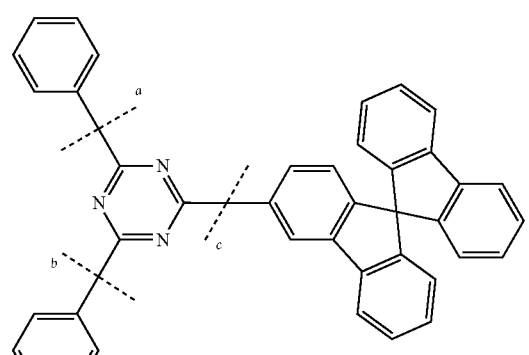

SF2-TRZ

| | a | SF3-TRZ •⁻ → SF2-TRZ • + Ph⁻ | 113.5 |
|---|---|---|---|
| | | SF3-TRZ •⁻ → SF2-TRZ⁻ + Ph• | 102.2 |
| | b | SF3-TRZ •⁻ → SF2-TRZ • + Ph⁻ | 113.5 |
| | | SF3-TRZ •⁻ → SF2-TRZ • + Ph⁻ | 102.4 |
| | c | SF3-TRZ •⁻ → SF• + TRZ⁻ | 103.8 |
| | | SF3-TRZ •⁻ → SF⁻ + TRZ• | 106.3 |

SF3-TRZ

TABLE 2-continued

Bond dissociation energies (BDE) in the SF2-TRZ, SF3-TRZ, and SF4-TRZ.

| Compound | Bond | Bond Dissociation Reaction | Average BDE (kcal/ mol) |
|---|---|---|---|
| 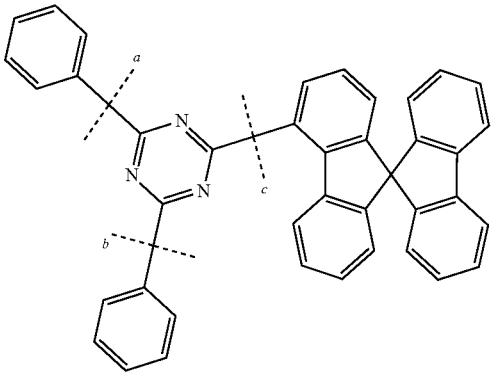 SF4-TRZ | a | SF4-TRZ·⁻ → SF2-TRZ· + Ph⁻ | 114.8 |
| | | SF4-TRZ·⁻ → SF2-TRZ⁻ + Ph· | 100.8 |
| | b | SF4-TRZ·⁻ → SF2-TRZ· + Ph⁻ | 114.8 |
| | | SF4-TRZ·⁻ → SF2-TRZ⁻ + Ph· | 100.8 |
| | c | SF4-TRZ·⁻ → SF· + TRZ⁻ | 92.2 |
| | | SF4-TRZ·⁻ → SF⁻ + TRZ· | 90.2 |

TABLE 3-1

HOMO and LUMO levels of reported TADF, fluorescent and phosphorescent emitters.

| Material | HOMO (eV) | LUMO (eV) |
|---|---|---|
| 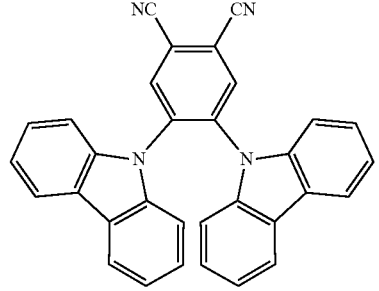 2CzPN | −5.80 | −3.0 |
| 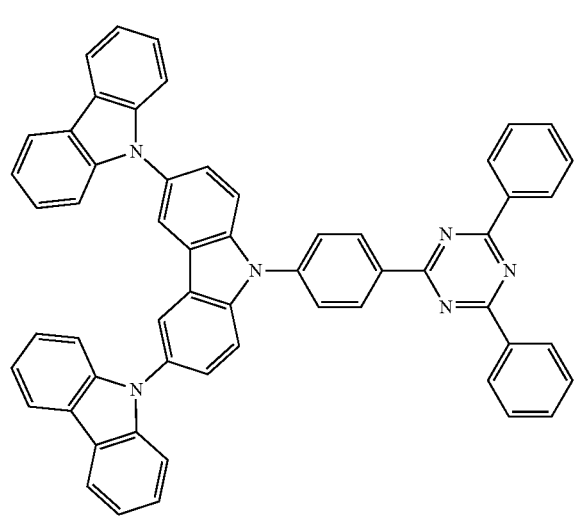 3Cz-TRZ | −5.9 | −2.8 |

TABLE 3-1-continued
HOMO and LUMO levels of reported TADF, fluorescent and phosphorescent emitters.
| Material | HOMO (eV) | LUMO (eV) |
|---|---|---|
| 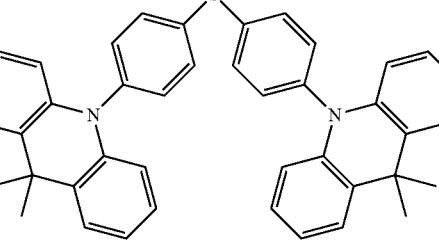 DMAC-DPS | −5.92 | −2.92 |
| 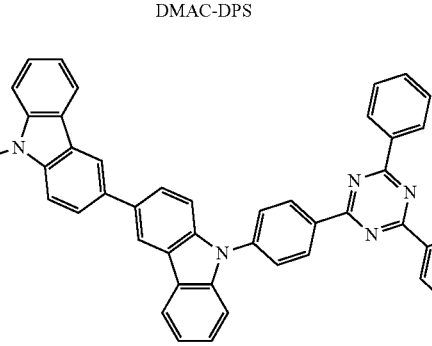 BCz-TRZ | −5.7 | −2.7 |
| 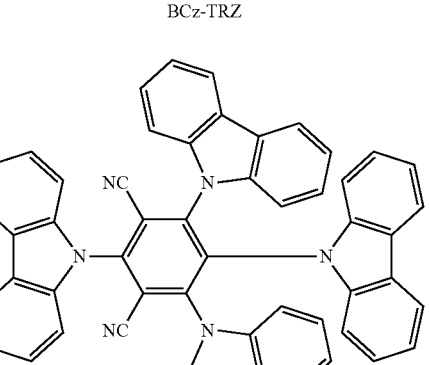 4 CzIPN | −5.8 | −3.4 |
TABLE 3-2
HOMO and LUMO levels of reported TADF, fluorescent and phosphorescent emitters. (continued)
| Material | HOMO (eV) | LUMO (eV) |
|---|---|---|
| 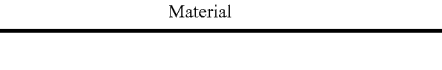 HK13 | −5.9 | −3.6 |

TABLE 3-2-continued

HOMO and LUMO levels of reported TADF, fluorescent and phosphorescent emitters. (continued)

| Material | HOMO (eV) | LUMO (eV) |
|---|---|---|
| 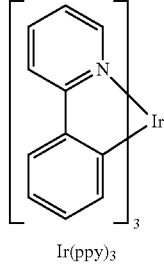  Ir(ppy)$_3$ | −5.2 | −2.7 |
| 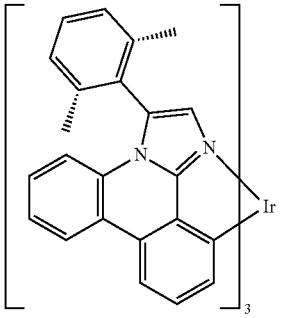  Ir(dmp)$_3$ | −5.0 | — |
| 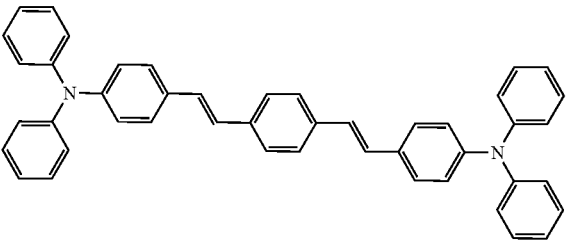  DSA-Ph | −5.4 | −2.7 |

TABLE 4

The photoluminescence quantum yields (PLQYs) of n-type hosts doped with TADF emitters.

| Film (60 nm) | PLQY |
|---|---|
| SF2-TRZ: 15 wt % 4CzIPN | 65% |
| SF3-TRZ: 15 wt % 4CzIPN | 90% |
| SF4-TRZ: 15 wt % 4CzIPN | 76% |
| SF3-TRZ: 10 wt % DPA-AQ | 80% |
| SF3-TRZ: 15 wt % BCz-TRZ | 82% |
| SF3-TRZ: 30 wt % BCz-TRZ | 78% |

Note
all films were measured under N$_2$ flow at room temperature.

TABLE 5

Zero-field mobility and Poole-Frenkel factor of SF2-TRZ and SF4-TRZ neat films.

| Material | $\mu_{0\,h}$ (10$^{-9}$ cm$^2$/Vs) | $\mu_{0\,e}$ (10$^{-8}$ cm$^2$/Vs) | $\beta_h$ (10$^{-4}$ cm$^{0.5}$/V$^{0.5}$) | $\beta_e$ (10$^{-3}$ cm$^{0.5}$/V$^{0.5}$) |
|---|---|---|---|---|
| SF2-TRZ | 7.50 | 6.68 | 2.70 | 1.74 |
| SF4-TRZ | 11.9 | 2.11 | 5.14 | 0.4 |

TABLE 6

Zero-field mobility and Poole-Frenkel factor of SF3-TRZ, mCBP and 4CzIPN-doped SF3-TRZ and mCBP films.

| Material | $\mu^0 h$ ($10^{-9}$ cm²/Vs) | $\mu^0 e$ ($10^{-8}$ cm²/Vs) | $\beta h$ ($10^{-4}$ cm$^{0.5}$/V$^{0.5}$) | $\beta e$ ($10^{-3}$ cm$^{0.5}$/V$^{0.5}$) |
|---|---|---|---|---|
| SF3-TRZ | 8.81 | 6990 | 5.56 | 1.42 |
| mCBP | 305 | — | 11.22 | — |
| SF3-TRZ: 15 wt % 4CzIPN | 35.1 | 25.4 | 26.99 | 0.44 |
| mCBP: 15 wt % 4CzIPN | 10.3 | 0.0101 | 87.88 | 0.41 |

Further Detailed Description of Invention

The present application discloses a compound having a triazine ring substituted by a spiro aromatic group. The "triazine ring" in the present application includes a 1,3,5-triazine ring. The "spiro aromatic group" in the present application is an aromatic group including a spiro structure, preferably an aromatic group in which the spiro carbon atom is bonded to the aromatic ring bonded to the triazine ring.

The compound having a triazine ring substituted by a spiro aromatic group is preferably represented by the following formula (1):

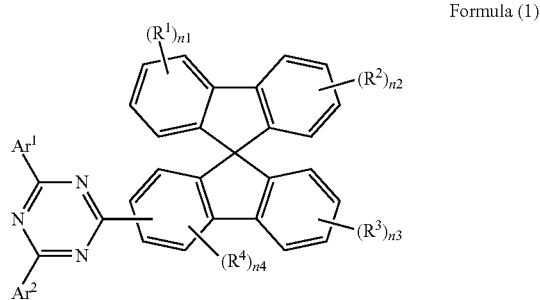

Formula (1)

In the formula (1), $Ar^1$ and $Ar^2$ each independently represent a substituted or unsubstituted aromatic group. The "aromatic group" includes substituted or unsubstituted aryl groups and substituted or unsubstituted heteroaryl groups. The groups represented by $Ar^1$ and $Ar^2$ may be the same or different. $R^1$ to $R^4$ each independently represent a substituent. The substituents represented by $R^1$ to $R^4$ may be the same or different. n1 to n3 are each independently an integer of from 1 to 4 and n4 is an integer of from 0 to 3. The numbers represented by n1 to n4 may be the same or different.

Examples of the substituent in the substituted aromatic group that $Ar^1$ and $Ar^2$ may represent and the substituent that $R^1$ to $R^4$ may represent include a hydroxy group, a halogen atom, a cyano group, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, trialkylsilylalkynyl group having 5 to 20 carbon atoms, a nitro group, etc. Among these examples, the substituents that may be further substituted with a substituent may be substituted. Preferred substituents include an alkyl group, an aryl group, a heteroaryl group, an alkoxy group, an aryloxy group or a heteroaryl group; more preferably an alkyl group having 1-20 carbon atoms, an aryl group having 6-40 carbon atoms, a heteroaryl group having 3-40 carbon atoms, an alkoxy group having 1-20 carbon atoms, an aryloxy group having 6-40 carbon atoms, or a heteroaryloxy group having 3-40 carbon atoms. Still more preferred substituents include an alkyl group having 1-10 carbon atoms, an aryl group having 6-20 carbon atoms, a heteroaryl group having 3-20 carbon atoms, an alkoxy group having 1-10 carbon atoms, an aryloxy group having 6-20 carbon atoms, or a heteroaryloxy group having 3-20 carbon atoms. Still further more preferred substituents include an alkyl group having 1-6 carbon atoms, or an alkoxy group having 1-6 carbon atoms.

The spirofluorenyl group in the formula (1) is bonded to the triazine ring at 2-, 3- or 4-position of the spirofluorene.

n1, n2, n3 and n4 may be selected from 0,1 and 2, and may be selected from 0 and 1. All of n1 to n4 may be 0.

In the following, specific examples of the compound represented by the formula (1) are exemplified. However, the compound represented by the formula (1) that is usable in the invention should not be interpreted in a limited way by these examples.

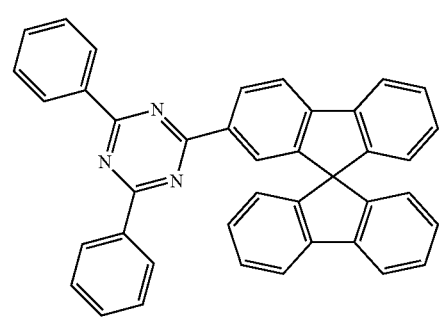

(SF2-TRZ)

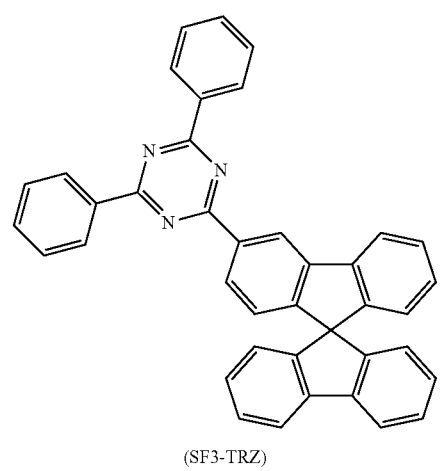

(SF3-TRZ)

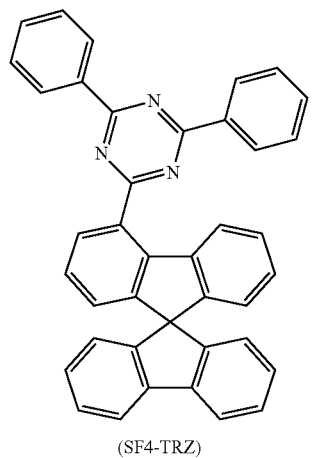
(SF4-TRZ)
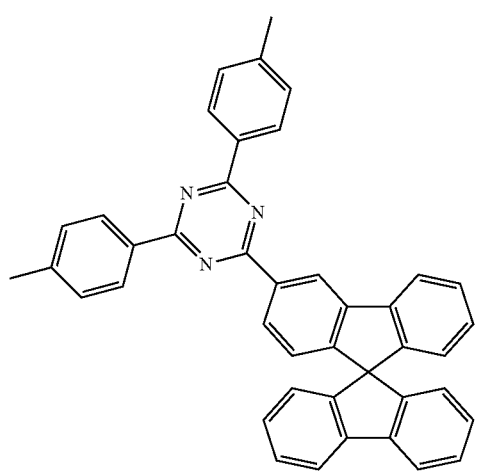
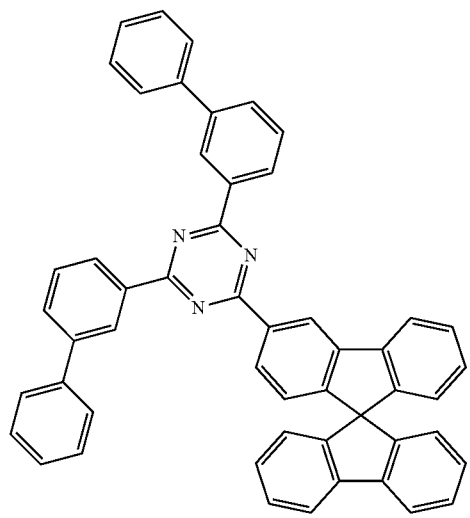
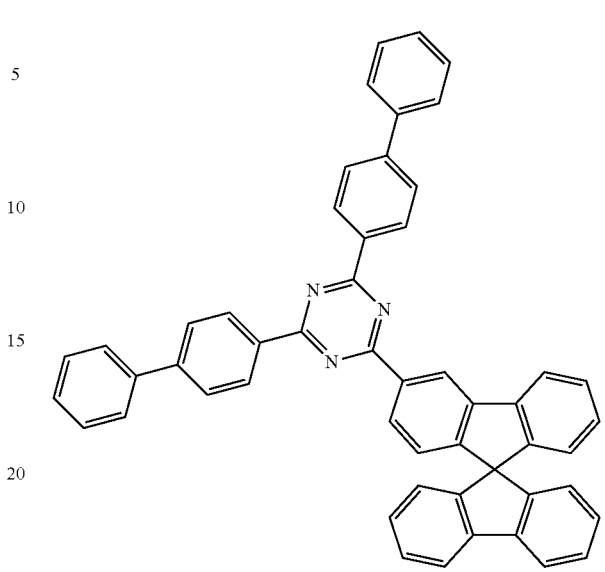
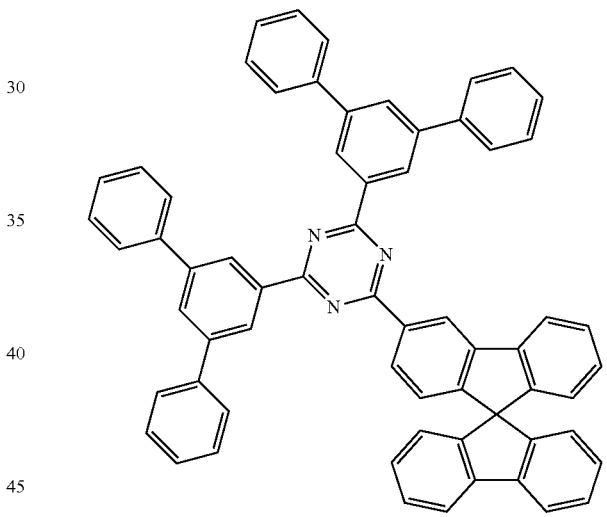

9
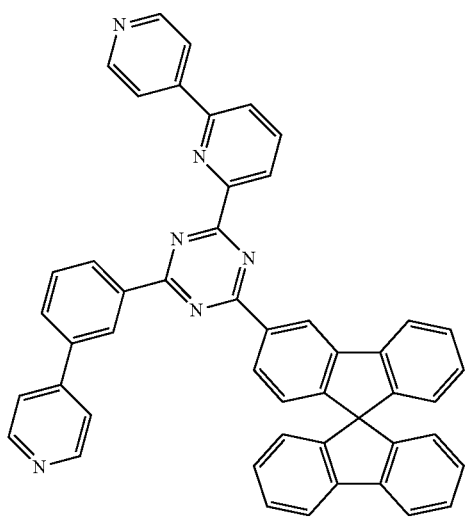
10
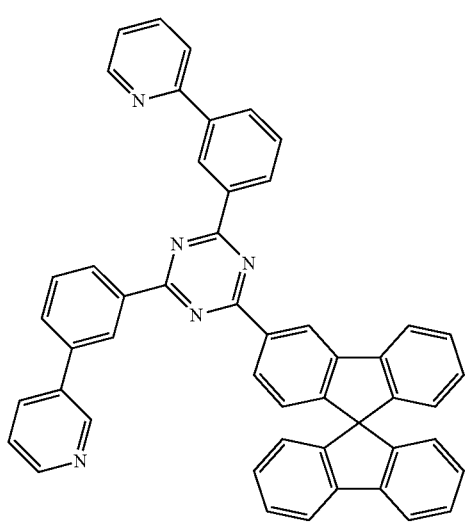
11
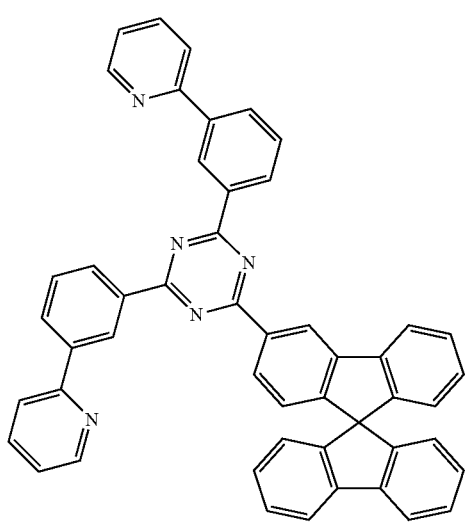
12
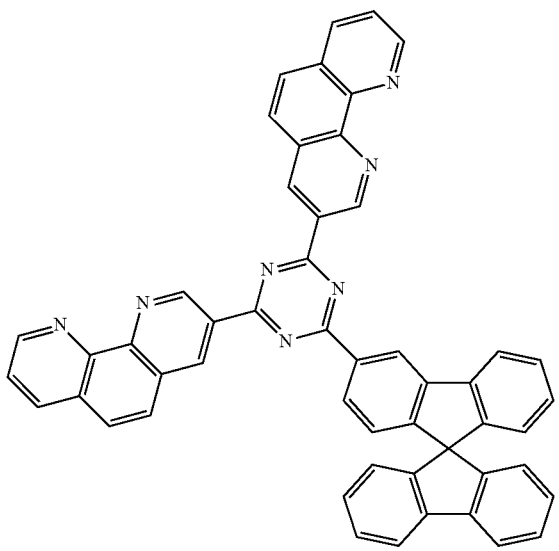
13
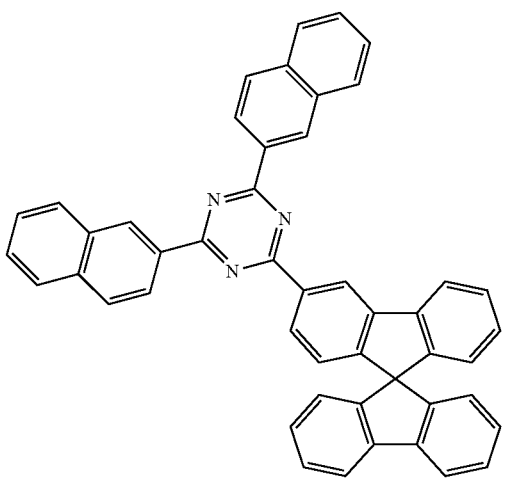
14
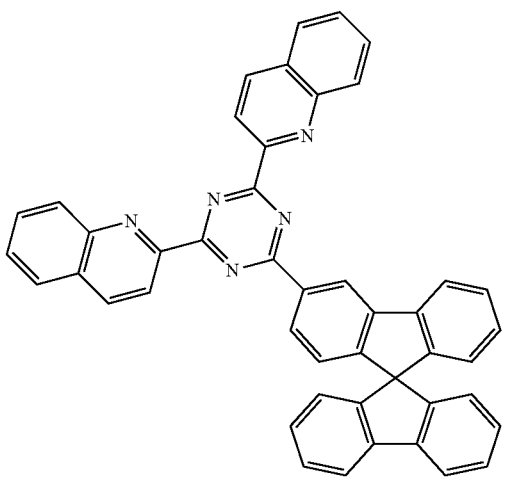

15
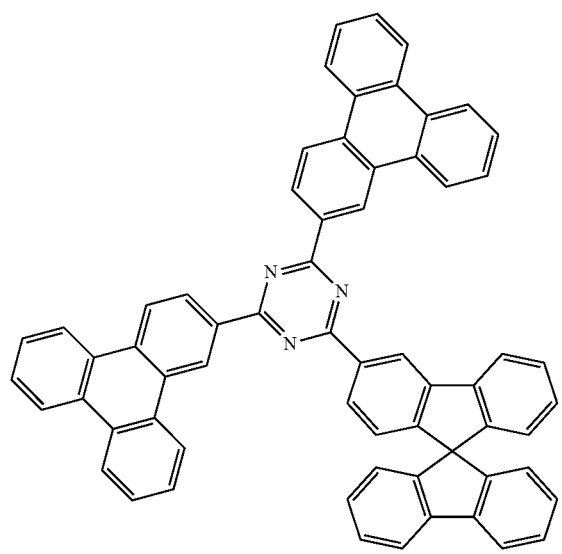
16
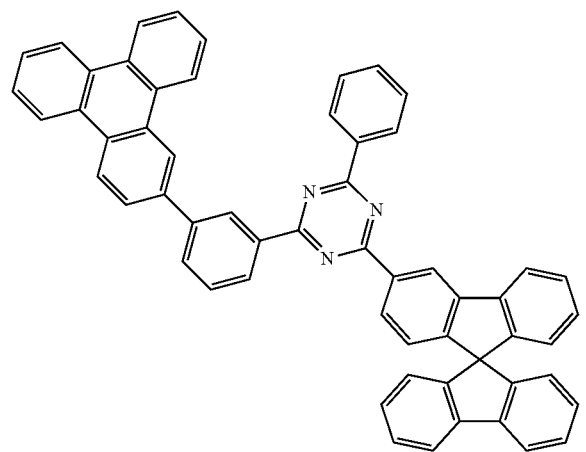
17
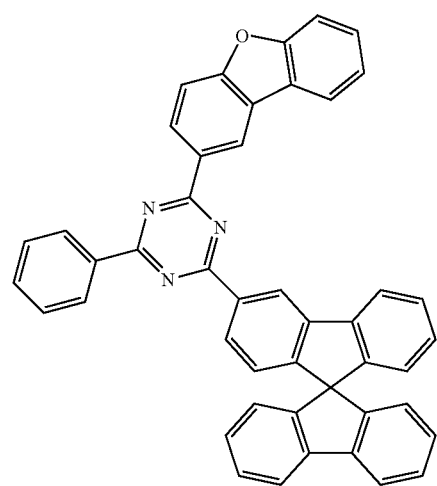
18
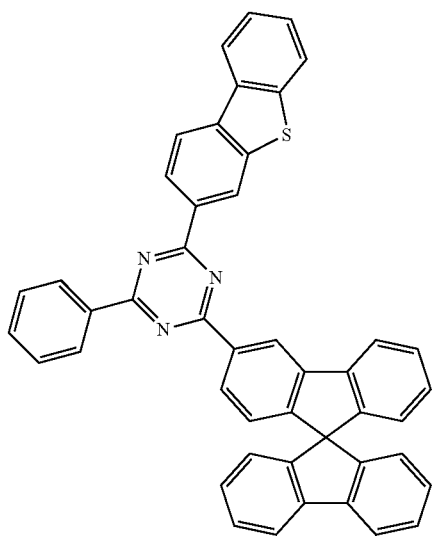
19
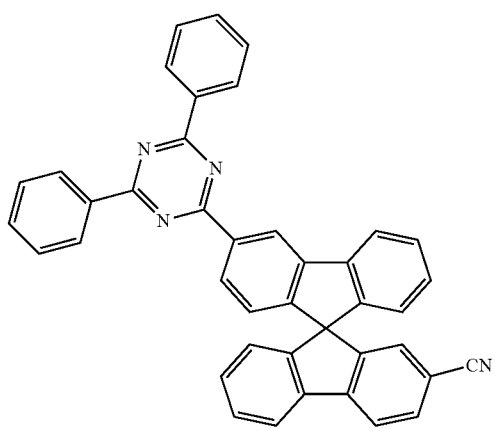
20
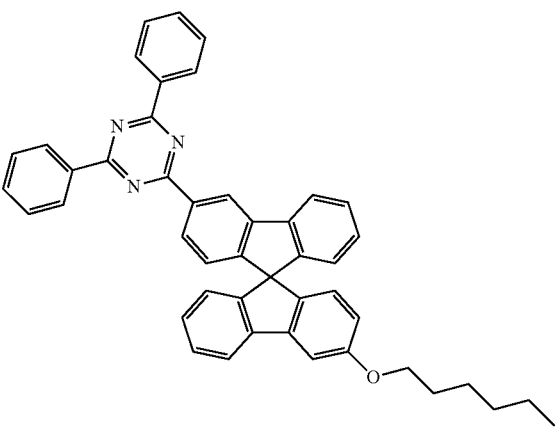

-continued
21
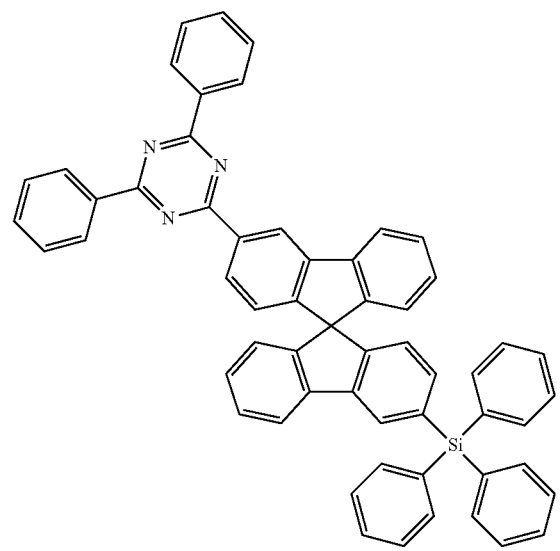
22
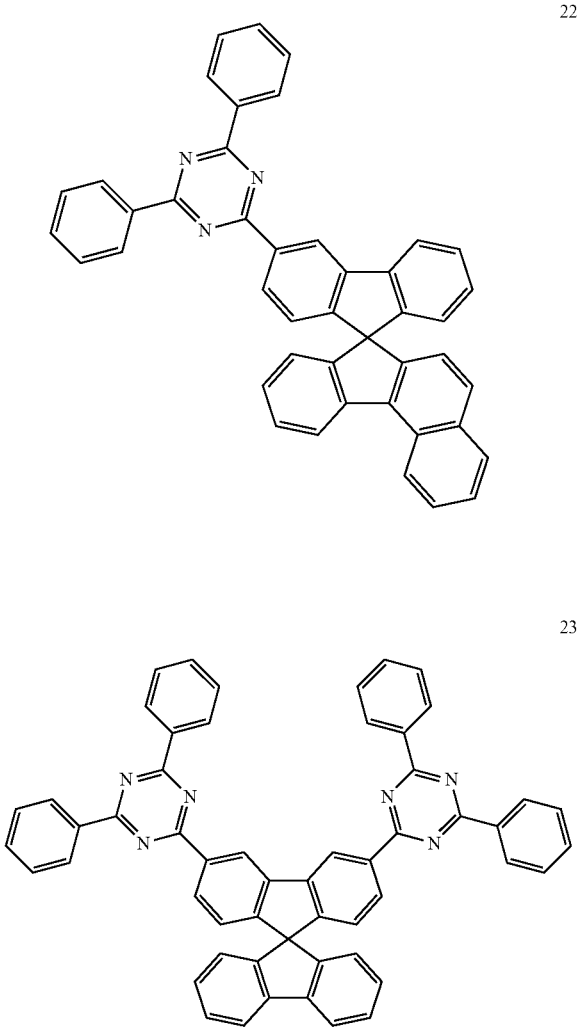
23
-continued
24
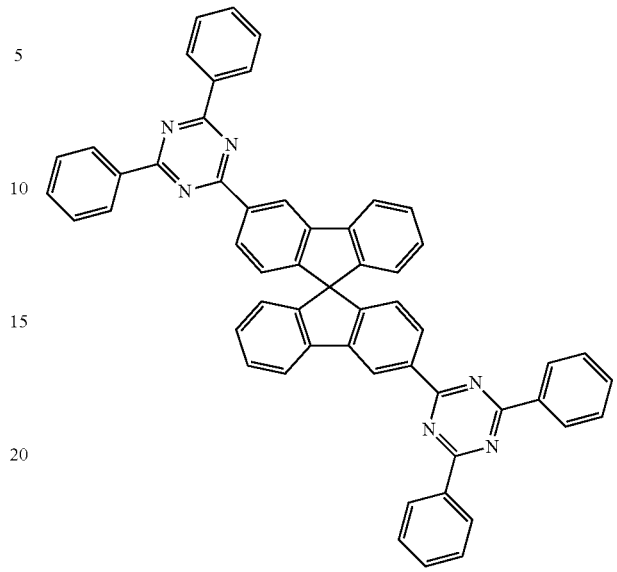
25
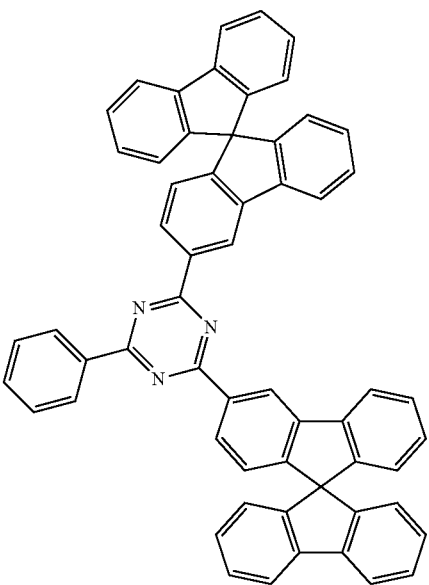

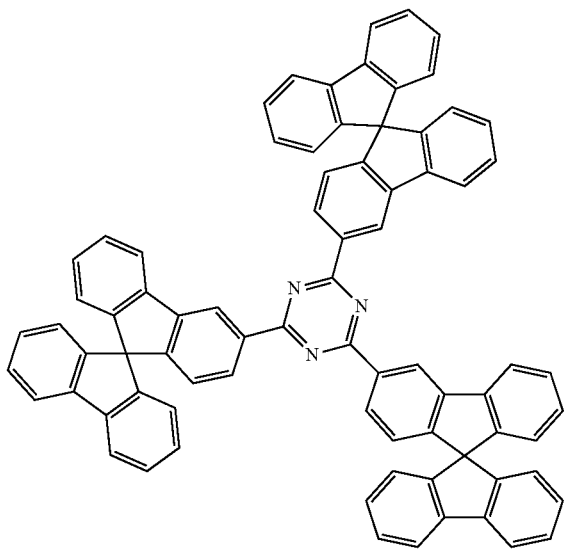

The molecular weight of the compound represented by the formula (1) is, for example, in the case of using it by forming an organic layer that contains a compound represented by the formula (1) according to a vapor deposition method, preferably 1500 or less, more preferably 1200 or less, even more preferably 1000 or less, still more preferably 900 or less. The lower limit of the molecular weight is the molecular weight of the smallest compound represented by the formula (1).

The compound represented by the formula (1) may be formed into a film according to a coating method irrespective of the molecular weight thereof. According to a coating method, even a compound having a relatively large molecular weight can be formed into a film.

By applying the invention, it may be taken into consideration to use a compound containing plural structures represented by the formula (1) in the molecule thereof.

For example, a polymerizable group is previously introduced in the structure represented by the formula (1), and it may be taken into consideration to use a polymer obtained through polymerization of the polymerizable group. Specifically, a monomer containing a polymerizable functional group in any of $R^1$, $R^2$, $R^3$, $R^4$, $Ar^1$ and $Ar^2$ in the formula (1) is prepared, and this is homo-polymerized singly or copolymerized with any other monomer to give a polymer having a repeating unit. Alternatively, compounds each having a structure represented by the formula (1) are coupled to give a dimer or a trimer.

Examples of the polymer having a repeating unit that contains a structure represented by the formula (1) include polymers containing a structure represented by the following formula (2) or (3).

Formula (2)

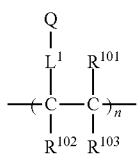

Formula (3)

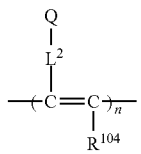

In the formulae (2) and (3), Q represents a group containing the structure represented by the formula (1), and $L^1$ and $L^2$ each represent a linking group. The carbon number of the linking group is preferably 0 to 20, more preferably 1 to 15, even more preferably 2 to 10. The linking group preferably has a structure represented by $-X^{11}-L^{11}-$. Here, $X^{11}$ represents an oxygen atom or a sulfur atom, and is preferably an oxygen atom. $L^{11}$ represents a linking group, and is preferably a substituted or unsubstituted alkylene group or a substituted or unsubstituted arylene group, more preferably a substituted or unsubstituted alkylene group having 1 to 10 carbon atoms or a substituted or unsubstituted phenylene group.

In the formulae (2) and (3), $R^{101}$, $R^{102}$, $R^{103}$ and $R^{104}$ each independently represent a substituent. Preferably, they each are a substituted or unsubstituted alkyl group having 1 to 6 carbon atoms, a substituted or unsubstituted alkoxy group having 1 to 6 carbon atoms, or a halogen atom, more preferably an unsubstituted alkyl group having 1 to 3 carbon atoms, an unsubstituted alkoxy group having 1 to 3 carbon atoms, a fluorine atom or a chlorine atom, and even more preferably an unsubstituted alkyl group having 1 to 3 carbon atoms, or an unsubstituted alkoxy group having 1 to 3 carbon atoms.

The linking group represented by $L^1$ and $L^2$ may bond to any of $R^1$, $R^2$, $R^3$, $R^4$, $Ar^1$ and $Ar^2$ in the structure of the formula (1). Two or more linking groups may bond to one Q to form a crosslinked structure or a network structure.

Specific structural examples of the repeating unit include structures represented by the following formulae (4) to (7).

Formula (4)

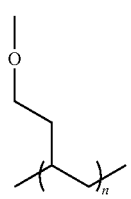

Formula (5)

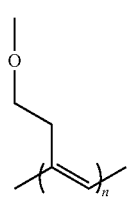

Formula (6)

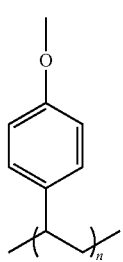

-continued

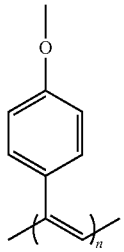

Formula (7)

Polymers having a repeating unit of the formulae (4) to (7) may be synthesized by previously introducing a hydroxy group into any of $R^1$, $R^2$, $R^3$, $R^4$, $Ar^1$ and $Ar^2$ in a structure of the formula (1), then introducing a polymerizable group into the structure through reaction with any of the following compounds via the hydroxy group serving as a linker, and polymerizing the polymerizable group.

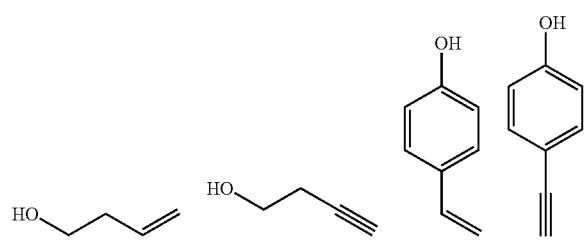

The polymer having a structure represented by the formula (1) in the molecule may be a polymer containing a repeating unit alone having a structure represented by the formula (1) or may be a polymer containing a repeating unit having any other structure. The repeating unit having a structure represented by the formula (1) contained in the polymer may be one type alone or may contain two or more types of repeating units. A repeating unit not having a structure represented by the formula (1) includes those derived from monomers to be used in ordinary copolymerization. For example, there are mentioned repeating units derived from monomers having an ethylenic unsaturated bond such as ethylene, styrene, etc.

[Organic Light-Emitting Device]

The compound having a triazine ring substituted by a spiro aromatic group, particularly the compound represented by the formula (1) of the invention may be used as a material for an organic light-emitting device. They may be used as a light-emitting lifetime lengthening agent. The compound represented by the formula (1) of the invention is particularly useful as a host material or an electron transport material for an organic light-emitting device. Accordingly, the compound represented by the formula (1) of the invention may be effectively used as host material in a light-emitting layer or as an electron transport material in an electron transport layer of an organic light-emitting device whereby an organic light-emitting device with high luminous efficiency and long lifetime is provided.

By using the compound represented by the formula (1) of the invention as a host material or an electron transport material, there can be provided excellent organic light-emitting devices such as organic photoluminescence devices (organic PL devices), organic electroluminescence devices (organic EL devices), etc. An organic photoluminescence device has a structure that contains a substrate having formed thereon at least a light-emitting layer. An organic electroluminescence device has a structure containing at least an anode, a cathode and an organic layer formed between the anode and the cathode. The organic layer contains at least a light-emitting layer, and may be formed only of a light-emitting layer, or may have one or more organic layer in addition to the light-emitting layer. Examples of the organic layer include a hole transport layer, a hole injection layer, an electron barrier layer, a hole barrier layer, an electron injection layer, an electron transport layer and an exciton barrier layer. The hole transport layer may be a hole injection and transport layer having a hole injection function, and the electron transport layer may be an electron injection and transport layer having an electron injection function. A specific structural example of an organic electroluminescence device is shown in FIG. 27. In FIG. 27, the numeral 1 denotes a substrate, 2 denotes an anode, 3 denotes a hole injection layer, 4 denotes a hole transport layer, 5 denotes a light-emitting layer, 6 denotes an electron transport layer, and 7 denotes a cathode.

The members and the layers of the organic electroluminescence device will be described below. The compound represented by the formula (1) of the invention may be used in at least one layer between the cathode and the anode of the organic electroluminescence device. The descriptions for the substrate and the light-emitting layer may also be applied to the substrate and the light-emitting layer of the organic photoluminescence device.

(Substrate)

The organic electroluminescence device of the invention is preferably supported by a substrate. The substrate is not particularly limited and may be those that have been commonly used in an organic electroluminescence device, and examples thereof used include those formed of glass, transparent plastics, quartz and silicon.

(Anode)

The anode of the organic electroluminescence device used is preferably formed of as an electrode material include a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

(Cathode)

The cathode is preferably formed of as an electrode material including a metal having a small work function (4 eV or less) (referred to as an electron injection metal), an alloy or an electroconductive compound, or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the organic electroluminescence device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

(Light-Emitting Layer)

The light-emitting layer is a layer, in which holes and electrons injected from the anode and the cathode, respectively, are recombined to form excitons, and the layer may contain an emitter only or may contain an emitter and a host material. The emitter may be selected from known emitters. Any of a fluorescent material, a delayed fluorescent material and a phosphorescent material can be used. Preferred is a delayed fluorescent material since a high luminous efficiency is achieved.

At least one compound represented by the formula (1) may be used as a host material. It is desirable to select those of such that at least any one of the lowest excited singlet energy and the lowest excited triplet energy thereof is higher than that of the emitter. It is more desirable to select those of such that both of the lowest excited singlet energy and the lowest excited triplet energy thereof are higher than that of the emitter. Consequently, the singlet excitons and the triplet excitons generated in the emitter can be confined in the molecule of the emitter, thereby eliciting the luminous efficiency of the material sufficiently. The light emission may be fluorescence emission, delayed fluorescence emission or phosphorescence emission and may include two or more emission. However, the light emission may partly include light emission from the host material as a part thereof.

The content of the emitter in the light-emitting layer is preferably 50 wt % or less. The upper limit of the content of the emitter is preferably less than 30 wt %, and may be, for example, less than 20 wt %, less than 10 wt %, less than 5 wt %, less than 3 wt %, less than 1 wt % or less than 0.5 wt %. The lower limit is preferably 0.001 wt % or more, and may be, for example, more than 0.01 wt %, more than 0.1 wt %, more than 0.5 wt % or more than 1 wt %. An emitter having a HOMO level of −5.70 eV or less, more preferably −5.75 eV or less, still more preferably −5.80 eV or less is preferably in a light-emitting layer containing a compound represented by the formula (1) as a host material.

The Light-Emitting Layer Contains

The light-emitting layer preferably contains a compound having a $\Delta E_{ST}$ of 0.3 eV or less. $\Delta E_{ST}$ is the difference between the lowest excited singlet energy level and the lowest excited triplet energy level. In the compound having a $\Delta E_{ST}$ of 0.3 eV or less, reverse intersystem crossing from the excited triplet state to the excited singlet state occurs easier. Thus, the compound having a $\Delta E_{ST}$ of 0.3 eV or less can be effectively used as a material capable of converting the excited triplet energy to the excited singlet energy. The light-emitting layer may contain a compound having a $\Delta E_{ST}$ of 0.3 eV or less as an emitter and the compound functions as a delayed fluorescent material emitting a delayed fluorescence whereby a high luminous efficiency is achieved. $\Delta E_{ST}$ is preferably 0.2 eV or less, more preferably 0.1 eV or less, still more preferably 0.05 eV or less. The light-emitting layer may contain a compound having a $\Delta E_{ST}$ of 0.3 eV or less as a dopant and an n-type compound as a host. The light-emitting layer may further contain an emitter as a dopant in addition to a compound having a $\Delta E_{ST}$ of 0.3 eV or less and an n-type compound, in which the emitter as a dopant emits a light mainly and the compound having a $\Delta E_{ST}$ of 0.3 eV or less functions as an assist dopant.

The principle of realizing a high luminous efficiency by the use of a delayed fluorescent material may be described as follows for an organic electroluminescence device as an example. In an organic electroluminescence device, carriers are injected from an anode and a cathode to an emitter to form an excited state for the emitter, with which light is emitted. In the case of a carrier injection type organic electroluminescence device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescence device. In the case where a delayed fluorescent material is used in an organic electroluminescence device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the luminous efficiency.

The light-emitting layer may contain a compound having a $\Delta E_{ST}$ of 0.3 eV or less as an assist dopant. The assist dopant is used in combination with a host material and an emitter and has a function of enhancing the light emission of the emitter. In a light-emitting layer containing a compound having a $\Delta E_{ST}$ of 0.3 eV or less as an assist dopant, the excited triplet energy in the host material generated by carrier recombination in the light-emitting layer and the excited triplet energy generated in the assist dopant is converted to the excited singlet energy by reverse intersystem crossing of the assist dopant whereby the excited singlet energy can be effectively used for fluorescence of the emitter. In such a device using an assist dopant, a delayed fluorescent material and a fluorescent material capable of emitting light by radiation deactivation from the excited singlet state are preferably used. As a host material, at least one compound represented by the formula (1) may be used. The assist dopant preferably has a $\Delta E_{ST}$ of 0.3 eV or less and a lowest excited singlet energy level that is higher than the emitter and lower than the host material. By using such an assist dopant, the excited singlet energy generated in the host material is easily transferred to the assist dopant and the emitter, and the excited singlet energy generated in the assist dopant and the excited singlet energy transferred from the host material to the assist dopant are easily transferred to the emitter. Thus, the excited singlet state in the emitter is efficiently generated whereby high luminous efficiency is achieved. The assist dopant preferably has a lowest excited triplet energy level that is lower than the host material whereby the excited triplet energy is easily transferred to the assist dopant and is converted to an excited singlet energy by reverse intersystem crossing of the assist dopant. Consequently, the excited singlet energy of the assist dopant is transferred to the emitter, and the excited singlet state of the emitter can be generated more efficiently whereby extremely high luminous efficiency is achieved.

The content of an assist dopant is preferably less than the content of a host material and more than an emitter in a light-emitting layer consisting of an emitter, an assist dopant and a host material, i.e. the content of an emitter<the content of an assist dopant<the content of a host material. In the light-emitting layer, the upper limit of the content of the assist dopant is preferably less than 50 wt %, more preferably less than 40 wt %, and may be, for example, less than 30 wt %, less than 20 wt % or less than 10 wt %. The lower limit of the content is preferably more than 0.1 wt %, and may be, for example, more than 1 wt % or more than 3 wt %.

The content of a compound represented by the formula (1) is preferably 50 wt % or more, more preferably more than 60 wt %, and may be, for example, more than 70 wt %, more than 80 wt %, more than 90 wt %, more than 95 wt %, more than 97 wt %, more than 99 wt % or more than 99.5 wt % in a light-emitting layer consisting of an emitter and a host material or in a light-emitting layer consisting of an emitter, an assist dopant and a host material. The upper limit of the content is preferably 99.999 wt % or less in a light-emitting layer consisting of an emitter and a host material. The upper limit of the content is preferably 99.899 wt % or less in a light-emitting layer consisting of an emitter, an assist dopant and a host material.

$\Delta E_{ST}$ in the present application is the difference between the lowest excited singlet energy ($E_{S1}$) and the lowest excited triplet energy ($E_{T1}$), i.e. $\Delta E_{ST} = E_{S1} - E_{T1}$. The lowest excited singlet energy ($E_{S1}$) and the lowest excited triplet energy ($E_{T1}$) can be determined as follows:

(1) Lowest Excited Singlet Energy $E_{S1}$

The compound to be measured and mCP are vapor-codeposited to a thickness of 100 nm on a Si substrate to make a concentration of the compound to be measured of 6% by weight, which is designated as a specimen. Alternatively, a toluene solution of the compound to be measured in $1 \times 10^{-5}$ mol/L is prepared. The specimen is measured for a fluorescence spectrum at ordinary temperature (300 K). The light emission is accumulated from immediately after the incidence of excitation light to after 100 nsec from the incidence, thereby providing a fluorescence spectrum with the fluorescence intensity as the ordinate and the wavelength as the abscissa. In the fluorescence spectrum, the ordinate is the light emission, and the abscissa is the wavelength. A tangent line is drawn for the downfalling part of the light emission spectrum on the short wavelength side, and the wavelength $\lambda_{edge}$ [nm] of the intersection point of the tangent line and the abscissa is obtained. The wavelength value is converted to an energy value according to the following conversion expression to provide the singlet energy $E_{S1}$.

$$E_{S1} [eV] = 1{,}239.85/\lambda_{edge} \qquad \text{Conversion Expression}$$

The light emission spectrum is measured with a nitrogen laser (MNL200, produced by Lasertechnik Berlin GmbH) as an excitation light source and a streak camera (C4334, produced by Hamamatsu Photonics K.K.) as a detector.

(2) Lowest Excited Triplet Energy $E_{T1}$

The same specimen as used for the singlet energy $E_{S1}$ is cooled to 5 K, the specimen for measuring phosphorescent light is irradiated with excitation light (337 nm), and the phosphorescence intensity is measured with a streak camera. The light emission is accumulated from after 1 msec from the incidence of excitation light to after 10 msec from the incidence, thereby providing a phosphorescence spectrum with the phosphorescence intensity as the ordinate and the wavelength as the abscissa. A tangent line is drawn for the upstanding part of the phosphorescence spectrum on the short wavelength side, and the wavelength $\lambda_{edge}$ [nm] of the intersection point of the tangent line and the abscissa is obtained. The wavelength value is converted to an energy value according to the following conversion expression to provide the triplet energy $E_{T1}$.

$$E_{T1} [eV] = 1{,}239.85/\lambda_{edge} \qquad \text{Conversion Expression}$$

The tangent line for the upstanding part of the phosphorescence spectrum on the short wavelength side is drawn in the following manner. Over the range in the phosphorescence spectrum curve of from the short wavelength end to the maximum peak value closest to the short wavelength end among the maximum peak values of the spectrum, a tangent line is assumed while moving within the range toward the long wavelength side. The gradient of the tangent line is increased while the curve is standing up (i.e., the value of the ordinate is increased). The tangent line that is drawn at the point where the gradient thereof became maximum is designated as the tangent line for the upstanding part of the phosphorescence spectrum on the short wavelength side.

A maximum peak having a peak intensity that is 10% or less of the maximum peak intensity of the spectrum is not included in the maximum peak values and thus is not designated as the maximum peak value closest to the short wavelength end, and the tangent line that is drawn at the point where the gradient became maximum that is closest to the maximum peak value closest to the short wavelength end is designated as the tangent line for the upstanding part of the phosphorescence spectrum on the short wavelength side.

(Injection Layer)

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transport layer and between the cathode and the light-emitting layer or the electron transport layer. The injection layer may be provided depending on necessity.

(Barrier Layer)

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transport layer, and inhibits electrons from passing through the light-emitting layer toward the hole transport layer. Similarly, the hole barrier layer may be disposed between the light-emitting layer and the electron transport layer, and inhibits holes from passing through the light-emitting layer toward the electron transport layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

(Hole Barrier Layer)

The hole barrier layer has the function of an electron transport layer in a broad sense. The hole barrier layer has a function of inhibiting holes from reaching the electron transport layer while transporting electrons, and thereby enhances the recombination probability of electrons and holes in the light-emitting layer. As the material for the hole barrier layer, the materials for the electron transport layer described later may be used depending on necessity.

(Electron Barrier Layer)

The electron barrier layer has the function of transporting holes in a broad sense. The electron barrier layer has a function of inhibiting electrons from reaching the hole transport layer while transporting holes, and thereby enhances the recombination probability of electrons and holes in the light-emitting layer.

(Exciton Barrier Layer)

The exciton barrier layer is a layer for inhibiting excitons generated through recombination of holes and electrons in the light-emitting layer from being diffused to the charge transport layer, and the use of the layer inserted enables effective confinement of excitons in the light-emitting layer, and thereby enhances the luminous efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transport layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transport layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the delayed fluorescent material, respectively.

(Hole Transport layer)

The hole transport layer is formed of a hole transport material having a function of transporting holes, and the hole transport layer may be provided as a single layer or plural layers.

The hole transport material has one of injection or transporting property of holes and barrier property of electrons, and may be any of an organic material and an inorganic material. Examples of known hole transport materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

(Electron Transport layer)

The electron transport layer is formed of a material having a function of transporting electrons, and the electron transport layer may be provided as a single layer or plural layers.

The electron transport material (which may also function as a hole barrier material in some cases) needs only to have a function of transporting electrons, which are injected from the cathode, to the light-emitting layer. The compound represented by the formula (1) of the invention may be used as an electron transport material. Examples of the other electron transport materials that may be used in the electron transport layer include a pyridine derivative, a thiazine derivative, a triazine derivative, a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transport material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescence device, the compound represented by the formula (1) may be used not only in a single layer but also in two or more layers. In this case, the compound represented by the formula (1) used in one layer and the compound represented by the formula (1) used in the other layers may be the same as or different from each other. For example, the compound represented by the formula (1) may be used in the light-emitting layer and also in the injection layer, the barrier layer, the hole barrier layer, the electron barrier layer, the exciton barrier layer, the hole transport layer, the electron transport layer and the like described above. The film forming method of the layers are not particularly limited, and the layers may be produced by any of a dry process and a wet process.

Specific examples of preferred materials that may be used in the organic electroluminescence device are shown below, but the materials that may be used in the invention are not construed as being limited to the example compounds. The compound that is shown as a material having a particular function may also be used as a material having another function. In the structural formulae of the example compounds shown below, Me represents a methyl group, R represents a hydrogen atom or a substituent, and n represents an integer of 3 to 5 unless otherwise defined.

Followings are examples of the compounds that can be used as a delayed fluorescent material for an emitter in the light-emitting layer or as an assist dopant in the light-emitting layer:

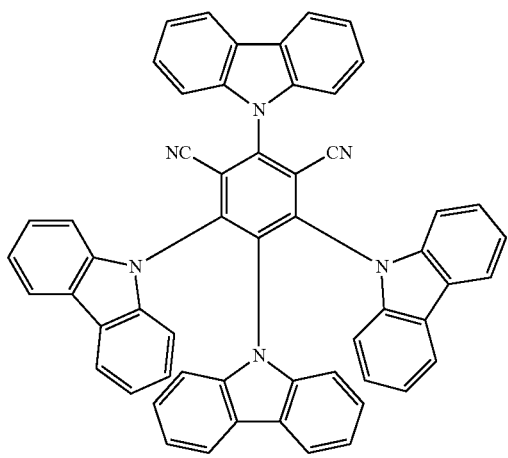

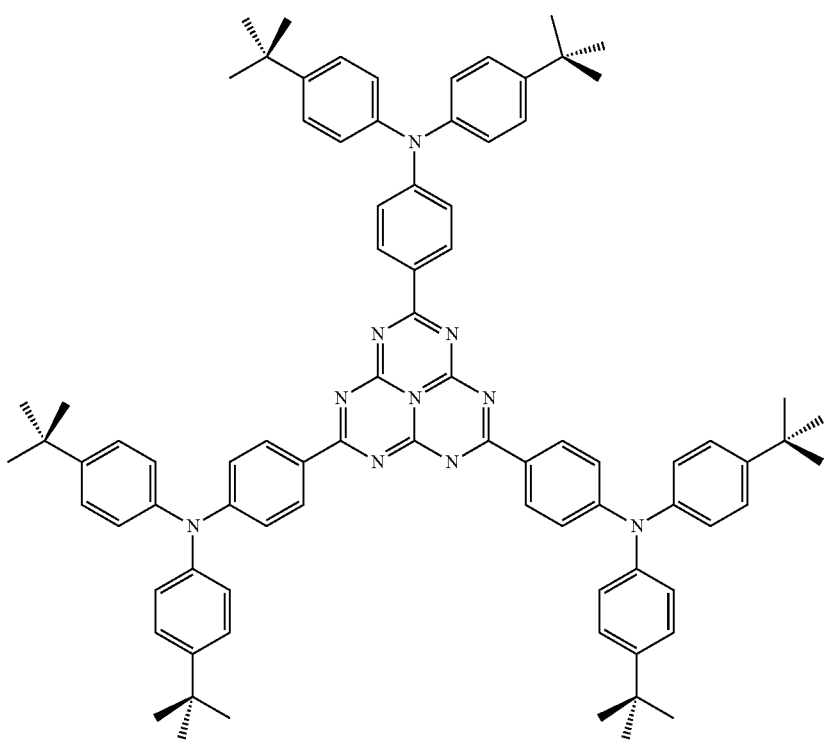

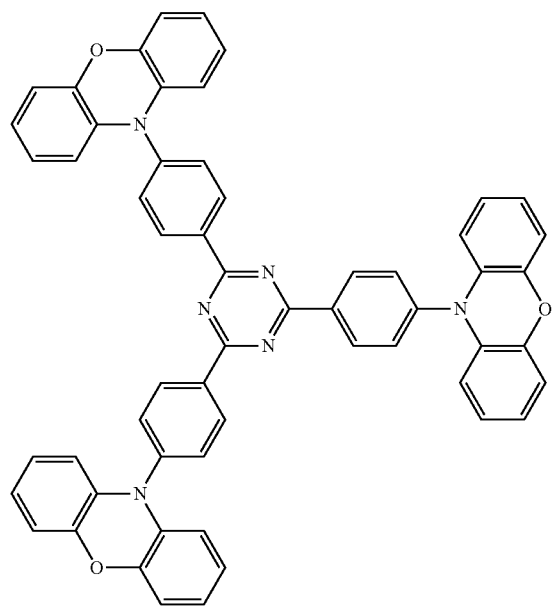
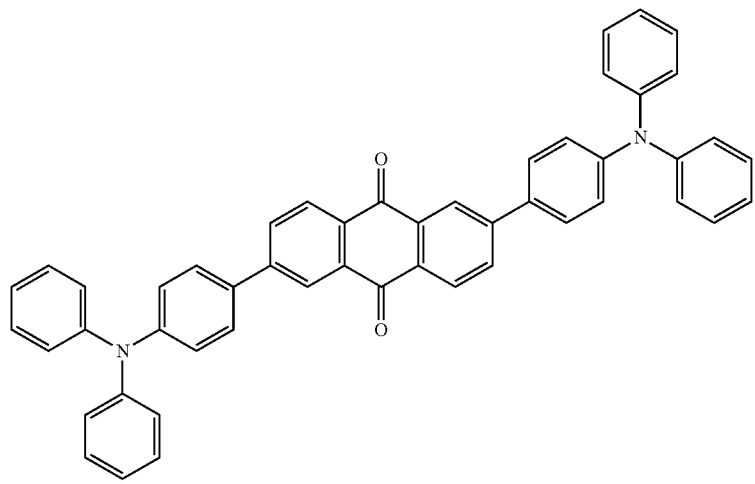
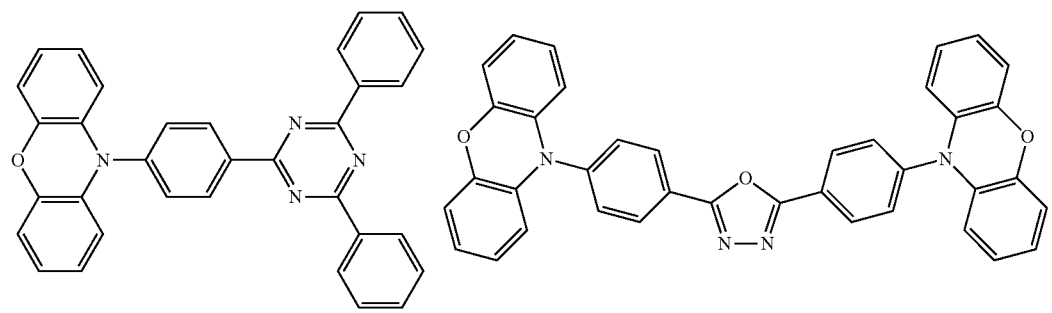

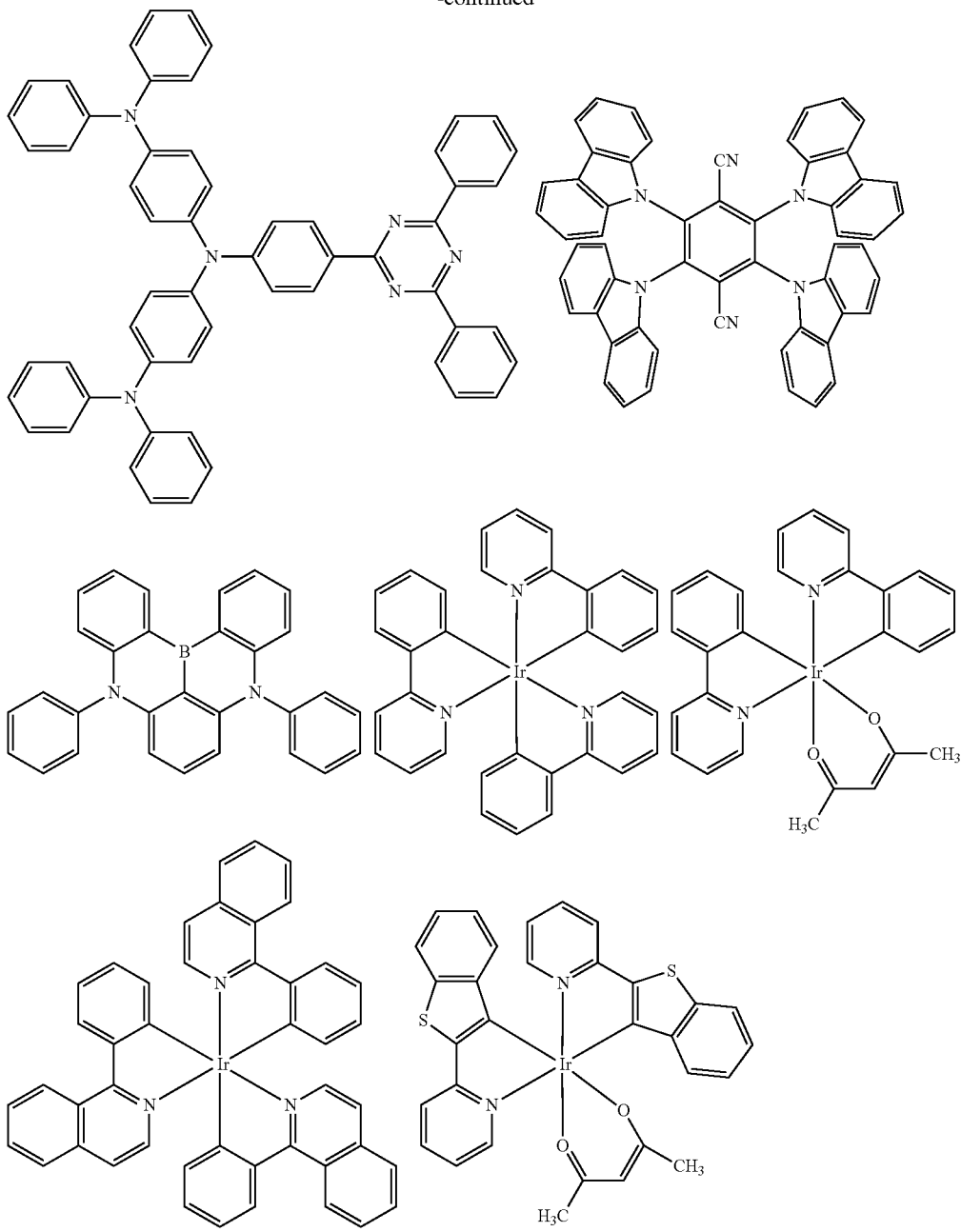

For example, the exemplified compounds and the compounds included in the formulae disclosed in the following paragraphs can be preferably used as a delayed fluorescent material: WO2013/154064, paragraphs 0008-0048 and 0095-0133; WO2013/011954, paragraphs 0007-0047 and 0073-0085; WO2013/011955, paragraphs 0007-0033 and 0059-0066: WO2013/081088, paragraphs 0008-0071 and 0118-0133; JP-A 2013-256490, paragraphs 0009-0046 and 0093-0134; JP-A 2013-116975, paragraphs 0008-0020 and 0038-0040; WO2013/133359, paragraphs 0007-0032 and 0079-0084; WO2013/161437, paragraphs 0008-0054 and 0101-0121; JP-A 2014-9352, paragraphs 0007-0041 and 0060-0069; and JP-A 2014-9224, paragraphs 0008-0048 and 0067-0076. The compounds capable of emitting a delayed fluorescence which are disclosed in the following publications can be also used preferably: JP-A 2013-253121; WO2013/133359; WO2014/034535; WO2014/115743; WO2014/122895; WO2014/126200; WO2014/136758; WO2014/133121; WO2014/136860; WO2014/196585; WO2014/189122; WO2014/168101; WO2015/008580; WO2014/203840; WO2015/002213; WO2015/016200; WO2015/019725; WO2015/072470; WO2015/108049; WO2015/080182; WO2015/072537; WO2015/080183; JP-A 2015-129240; WO2015/129714; WO2015/129715; WO2015/133501; WO2015/136880; WO2015/137244; WO2015/137202; WO2015/137136; WO2015/146541; and WO2015/159541. The above publications in this paragraph are herein incorporated by reference.

Preferred examples of compounds usable as a hole injection material are mentioned below 49 50
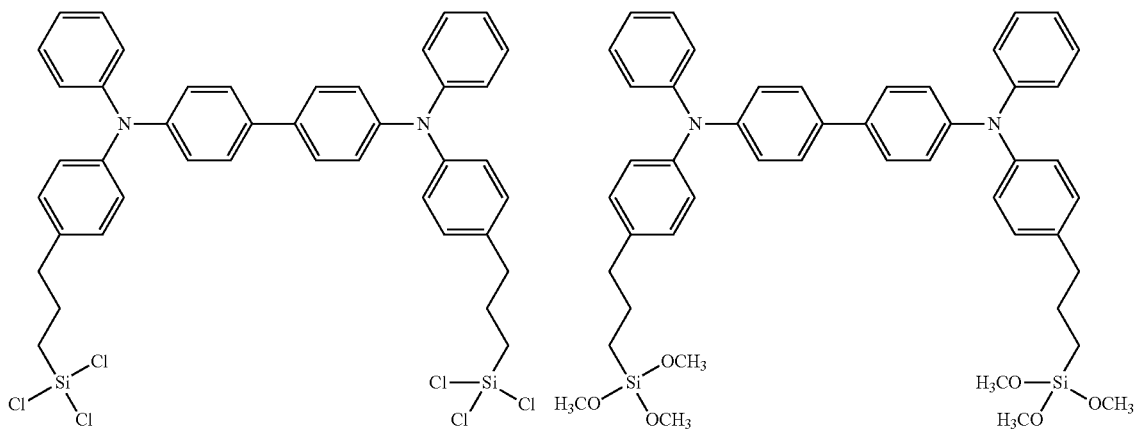
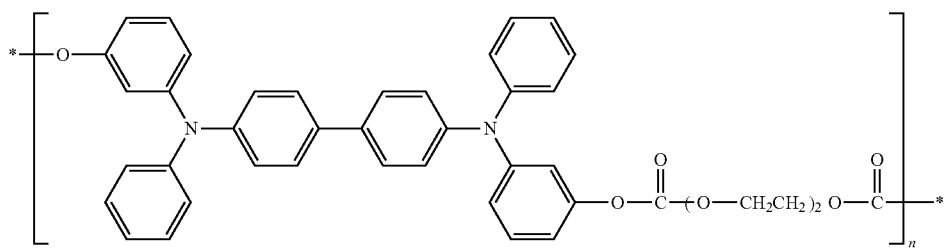
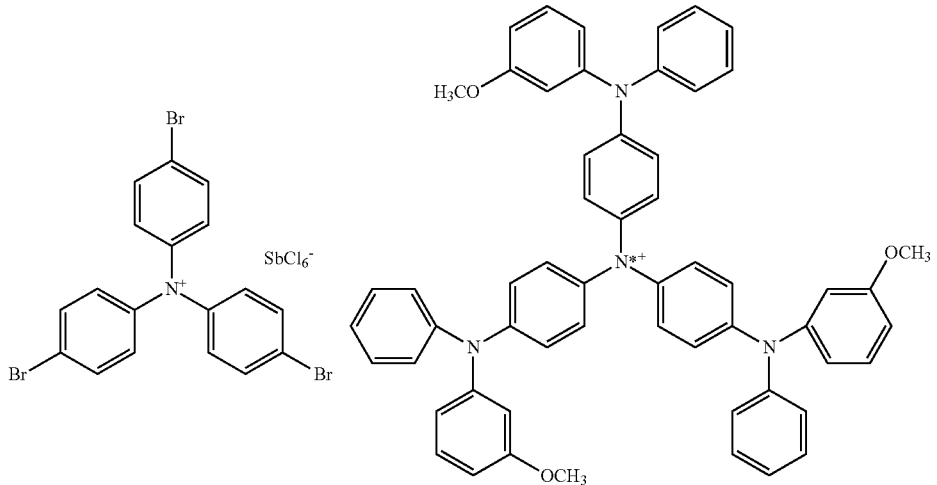
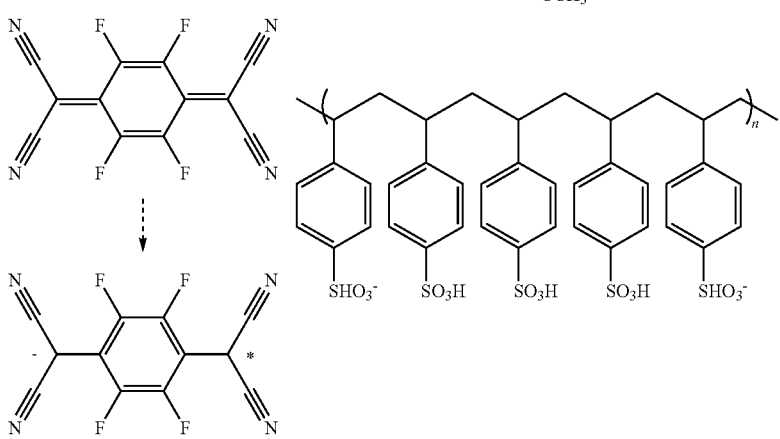

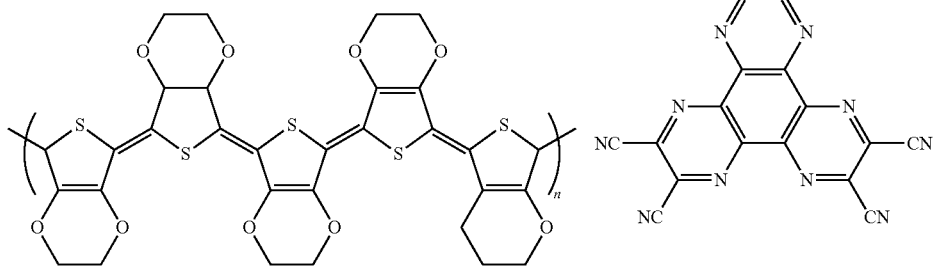
Next, preferred examples of compounds usable as a hole transport material are mentioned below.
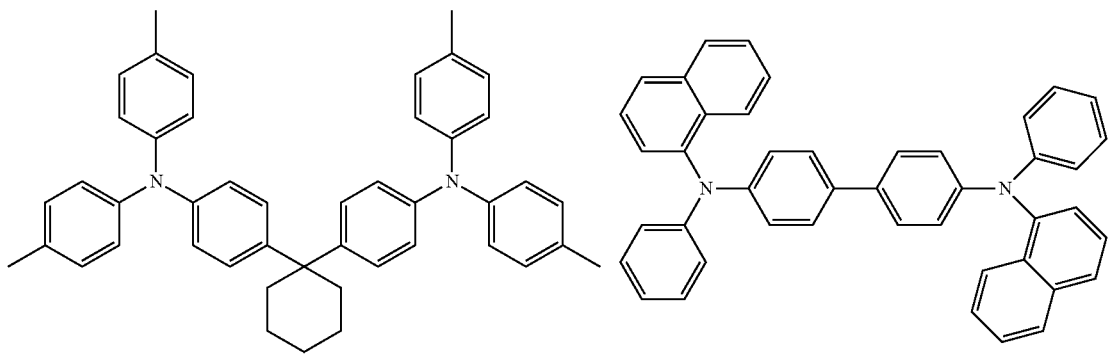
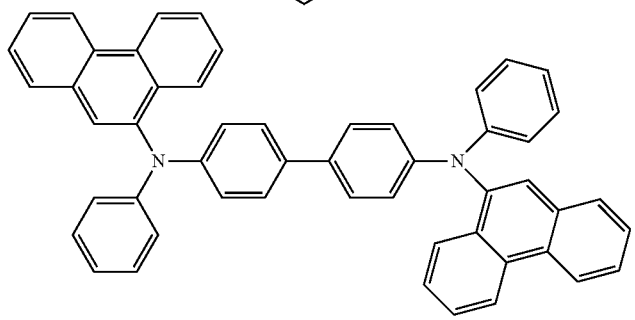
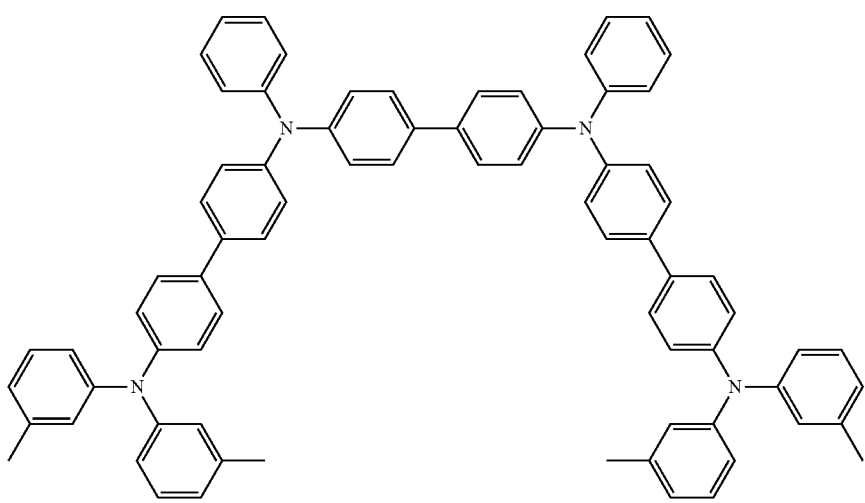

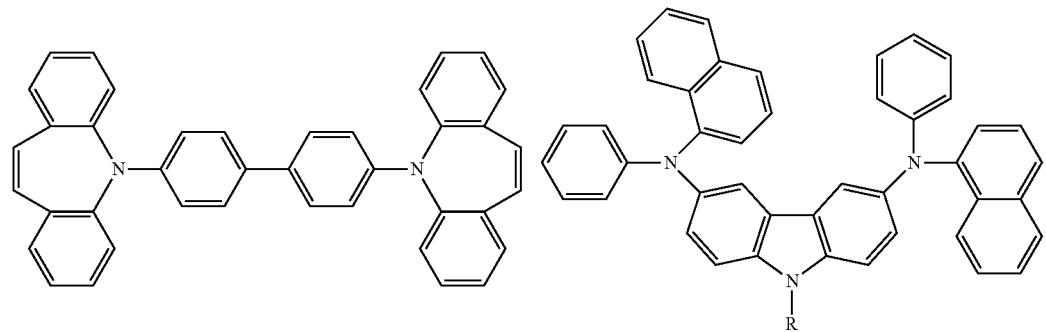
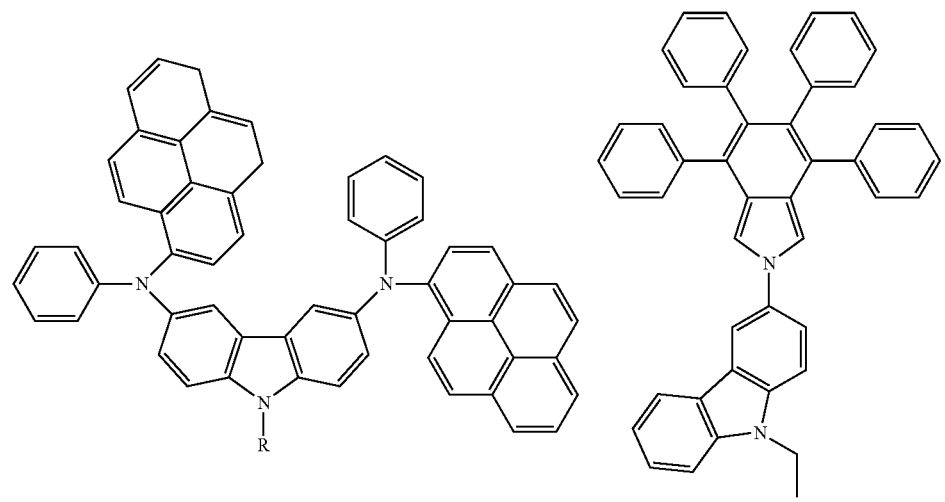
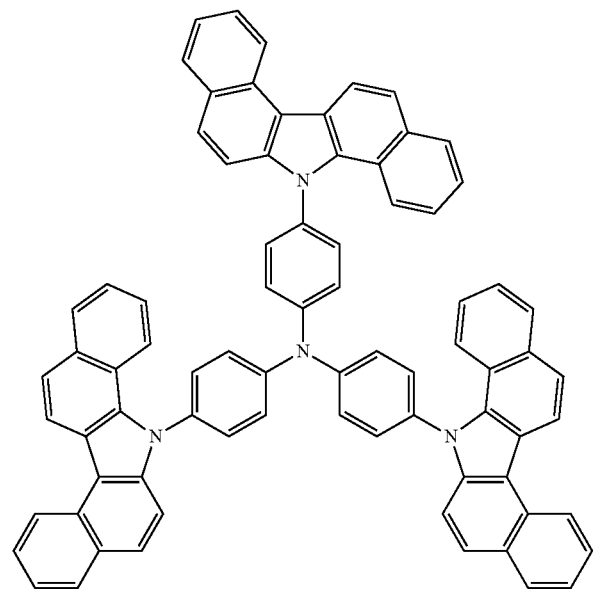

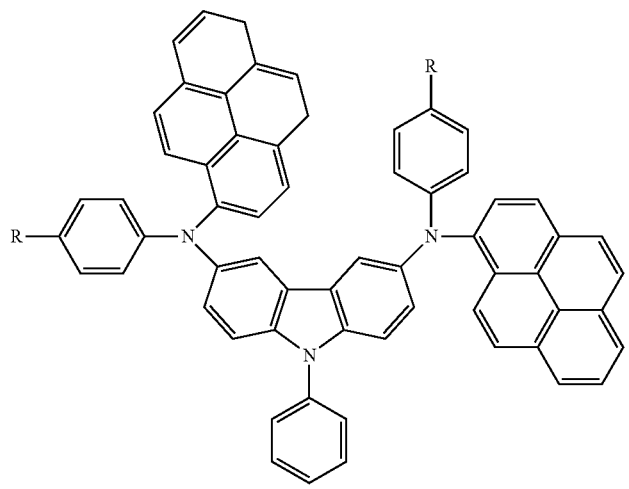
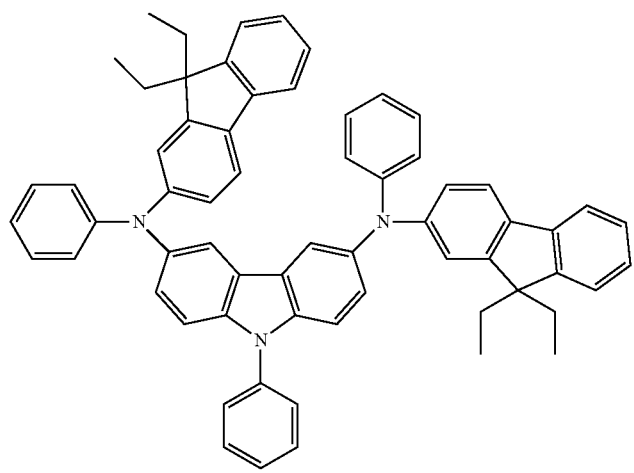
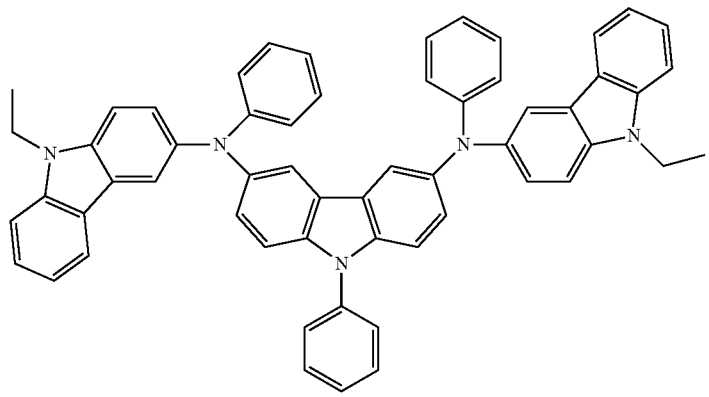

57 58
-continued
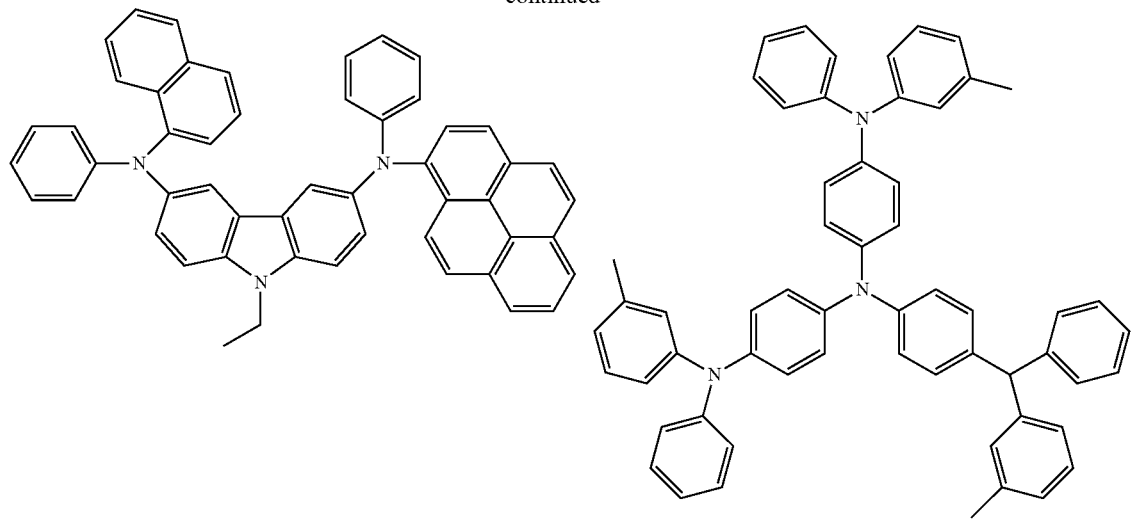
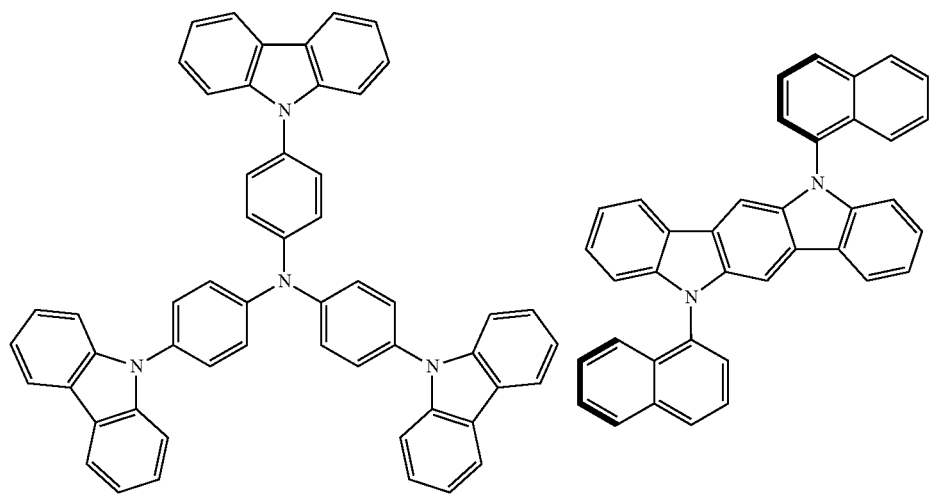
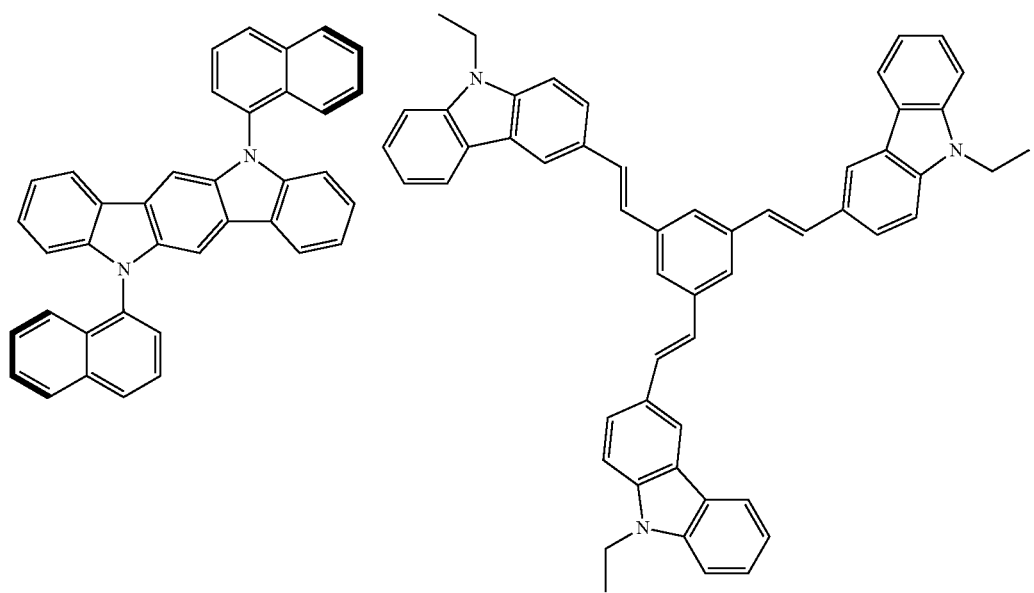

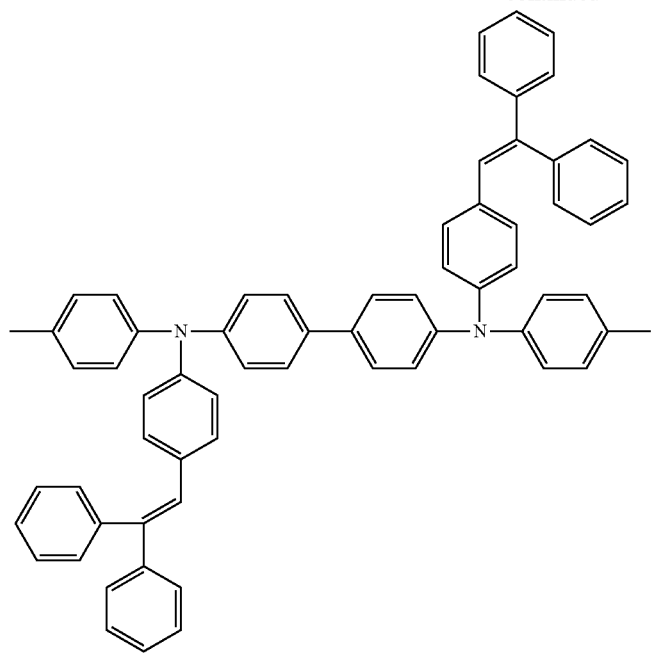
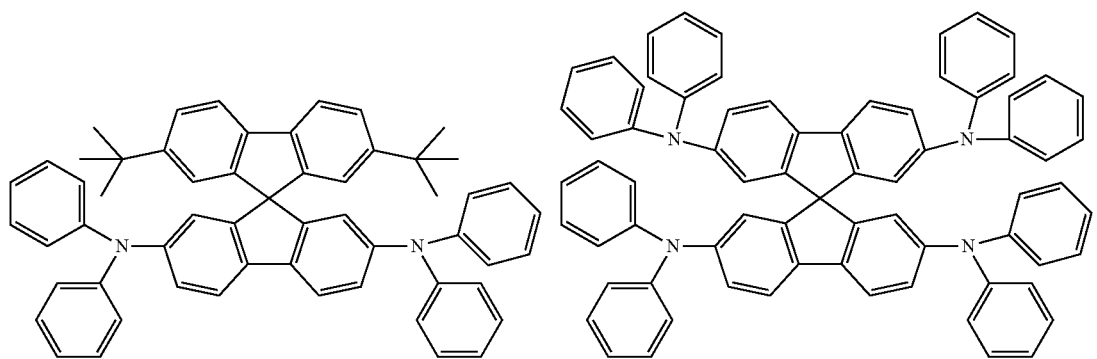
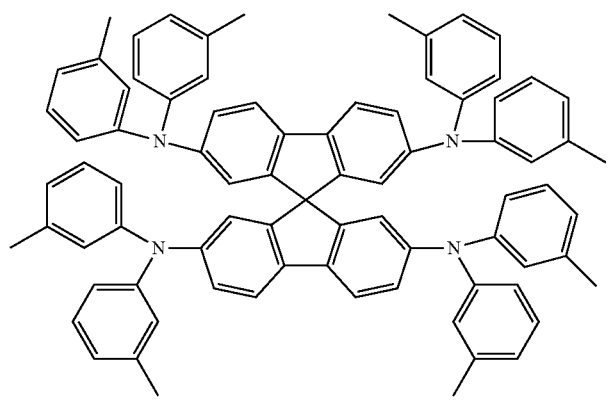

-continued
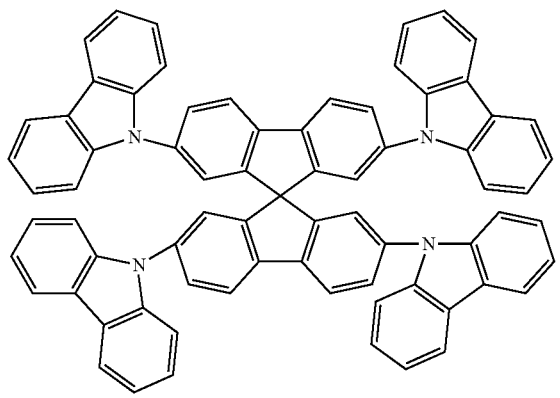
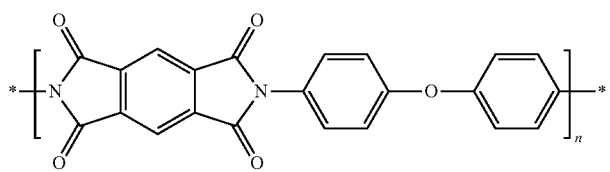
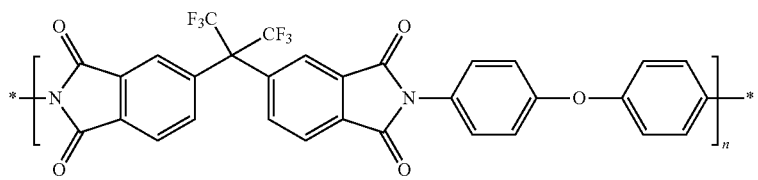
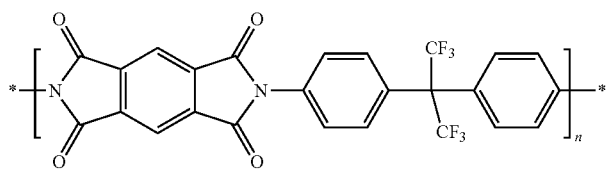
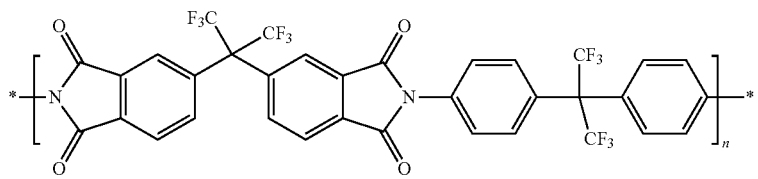
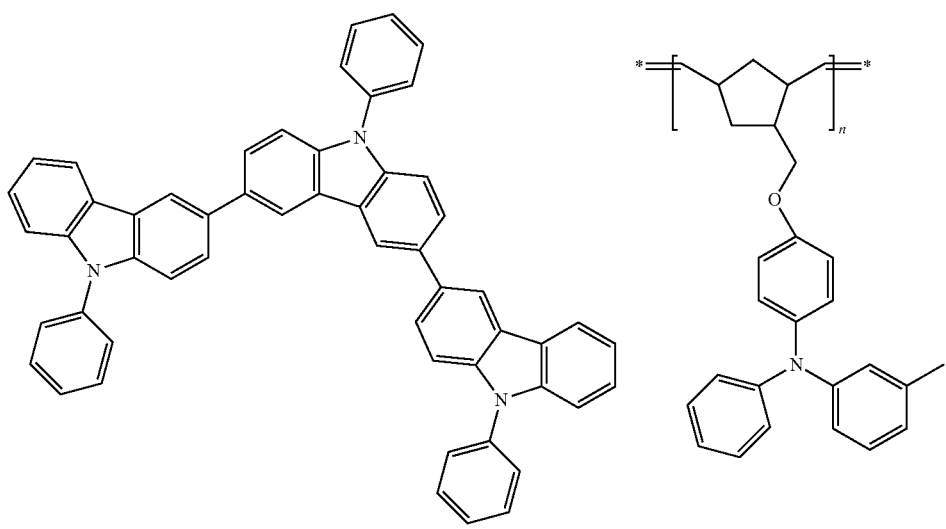

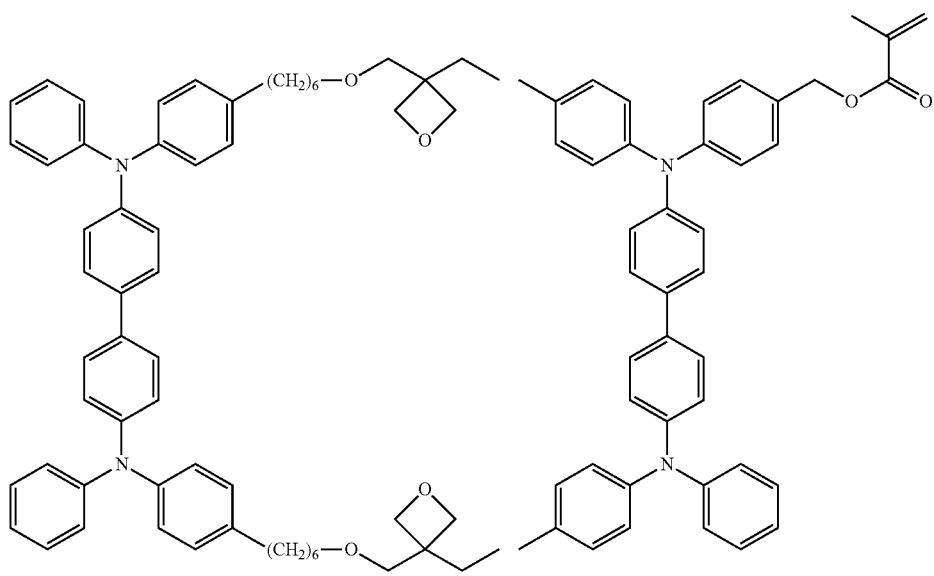
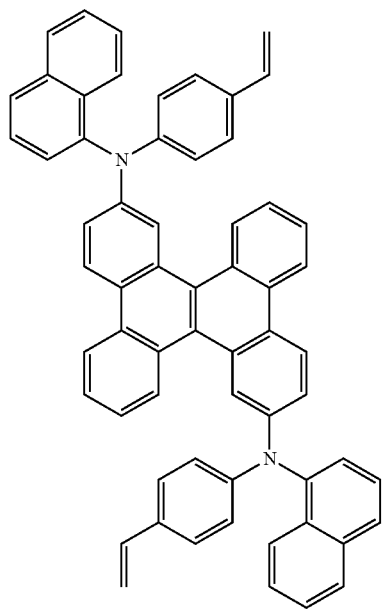
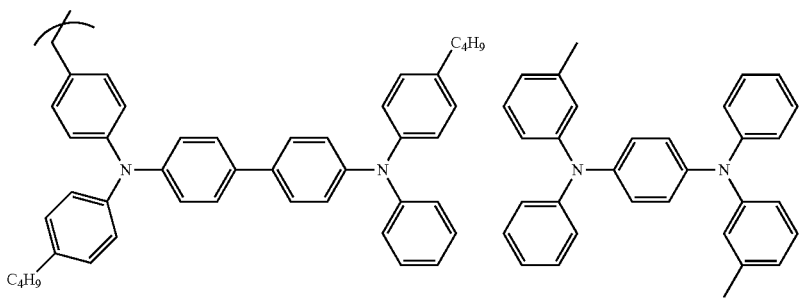

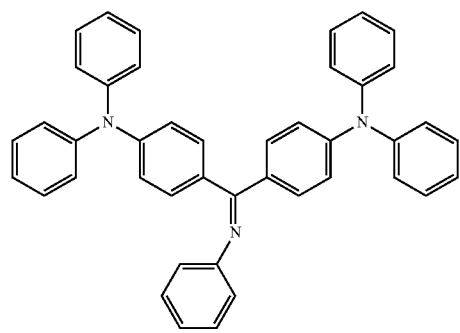
-continued
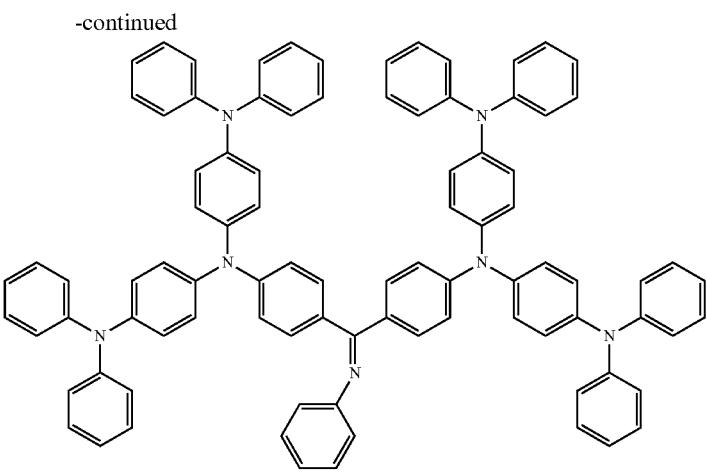
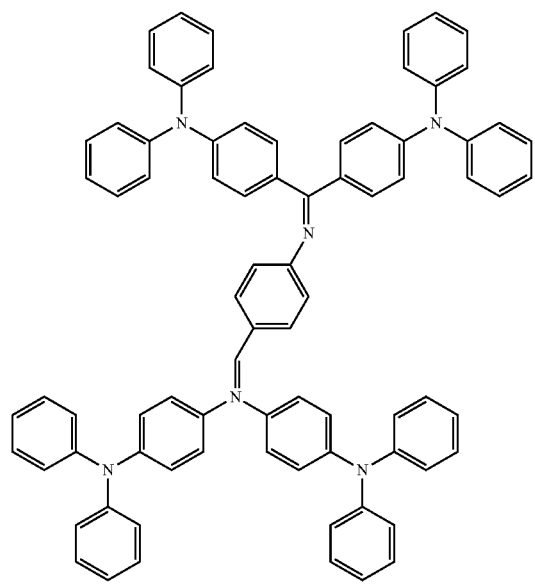

-continued
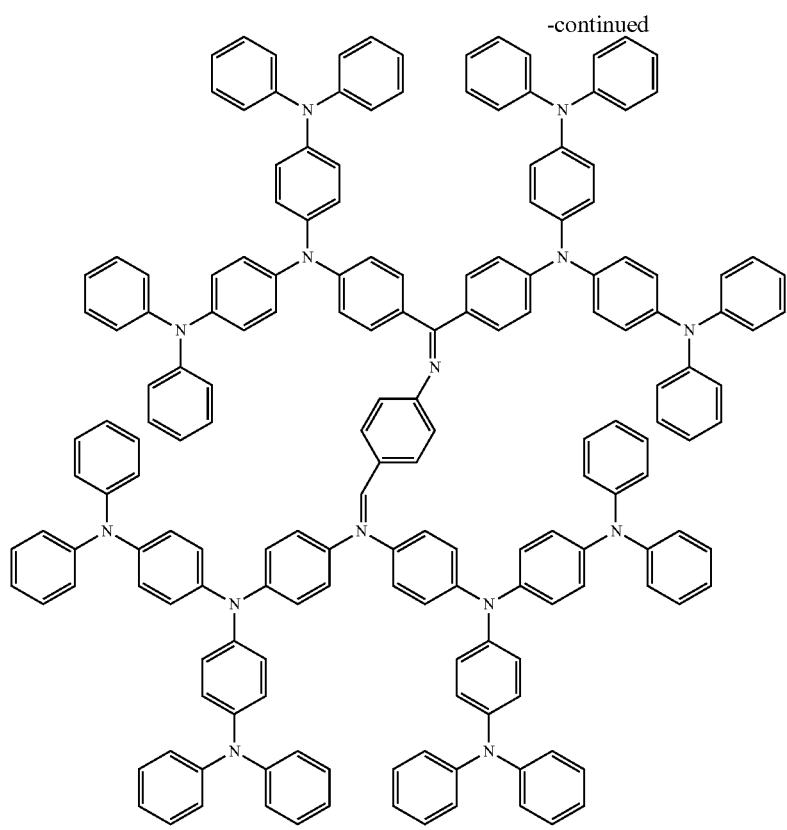
Next, preferred examples of compounds usable as an electron barrier material are mentioned below.
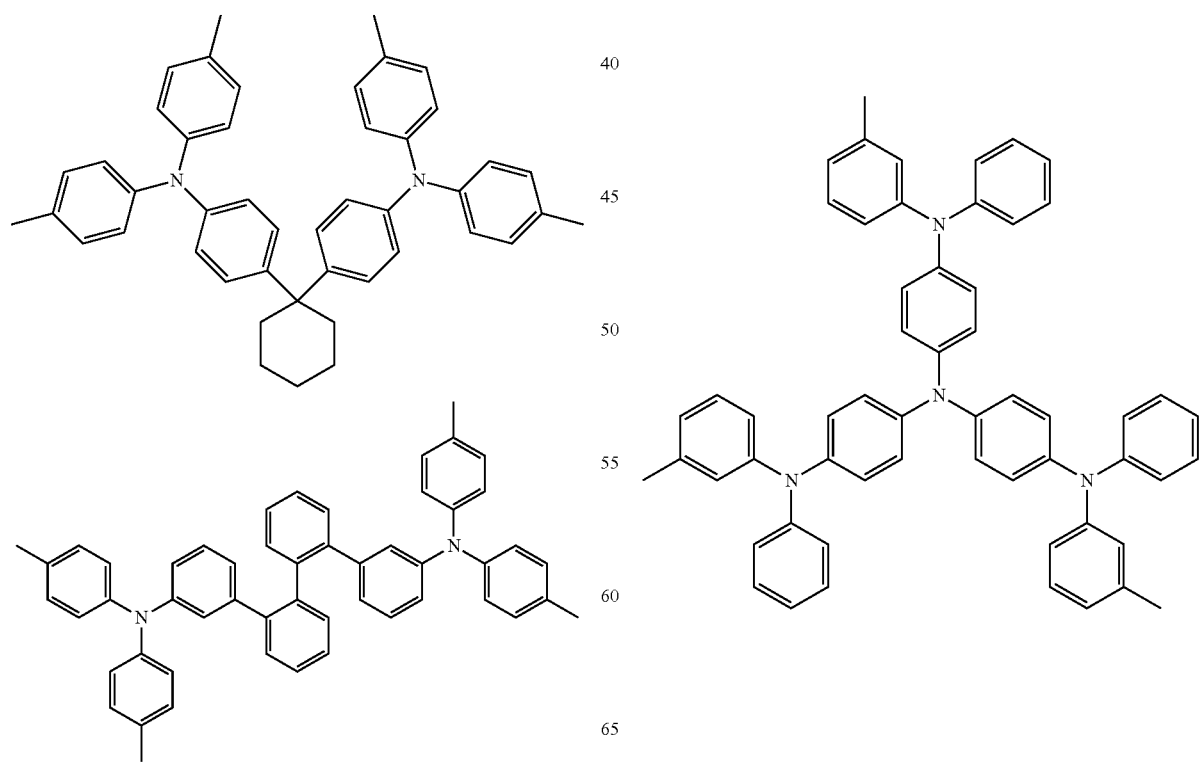
-continued

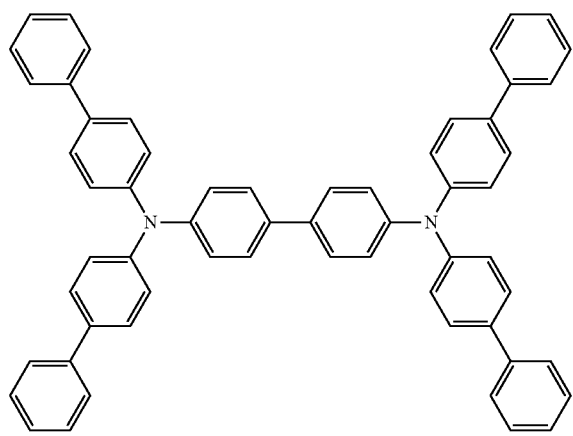
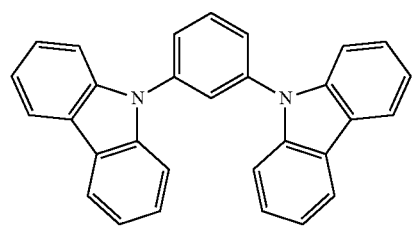
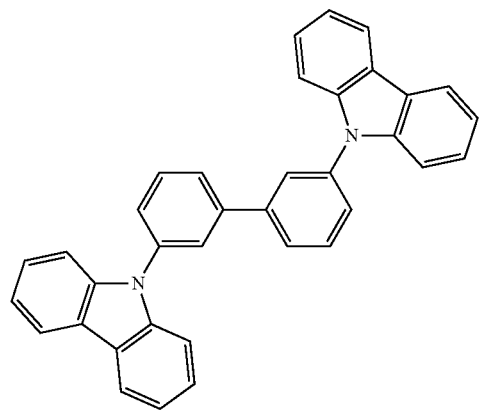
Next, preferred examples of compounds usable as a hole transport material are mentioned below.
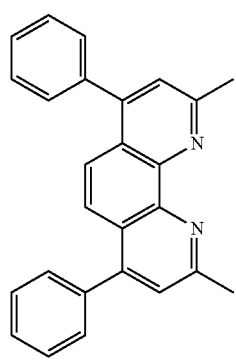
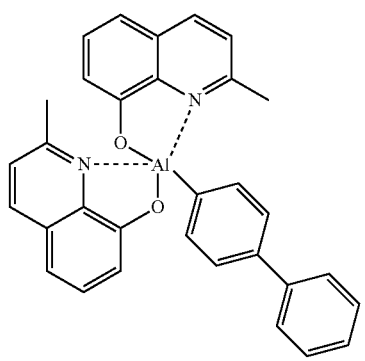
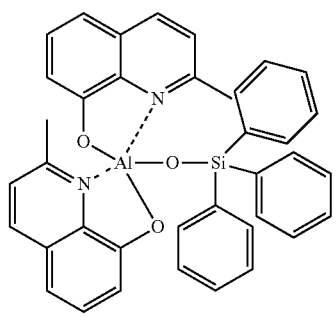
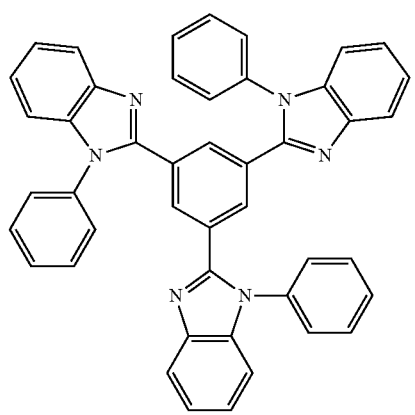
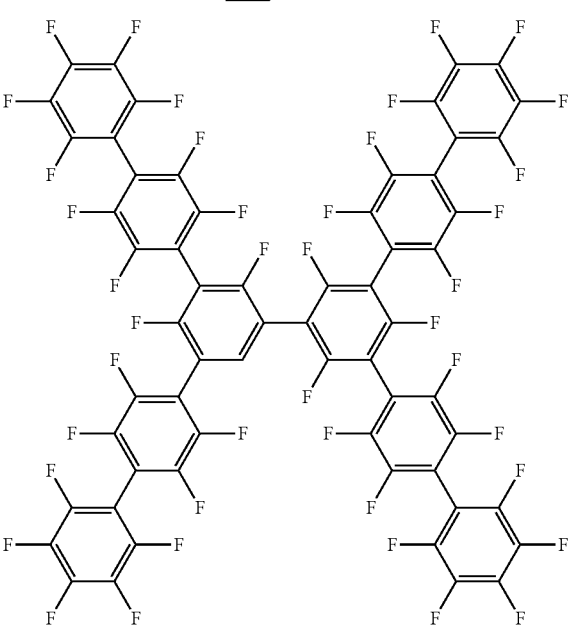

71
-continued
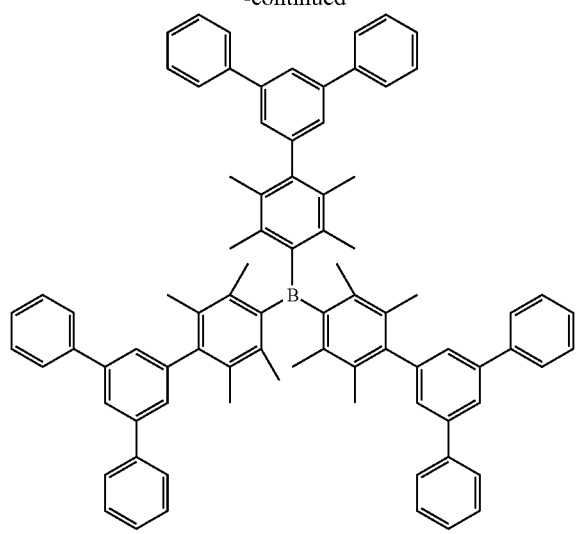
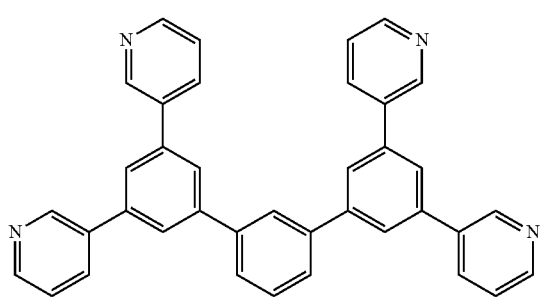
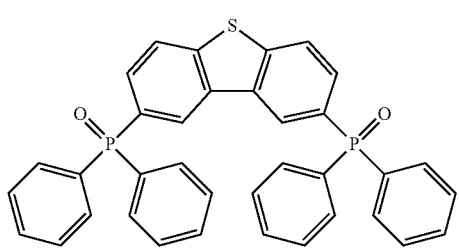
72
-continued
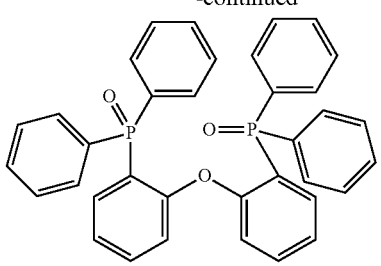
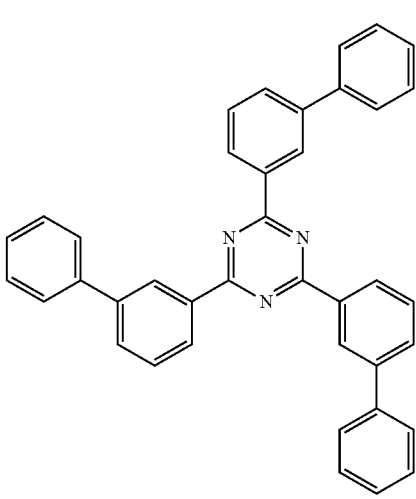
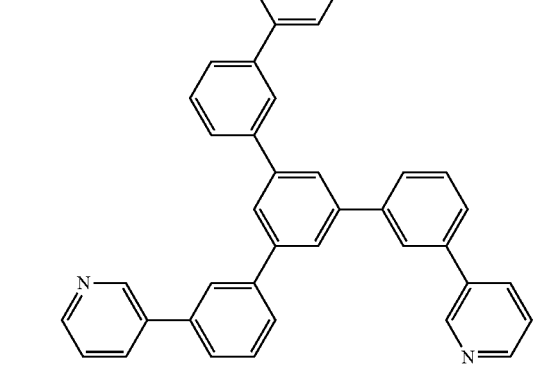
Next, preferred examples of compounds usable as a hole transport material are mentioned below.

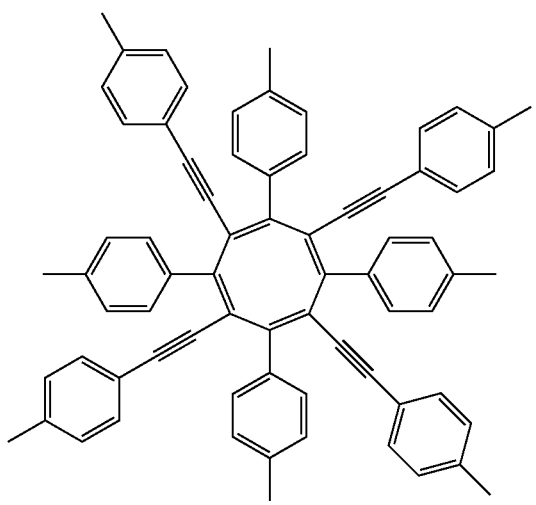
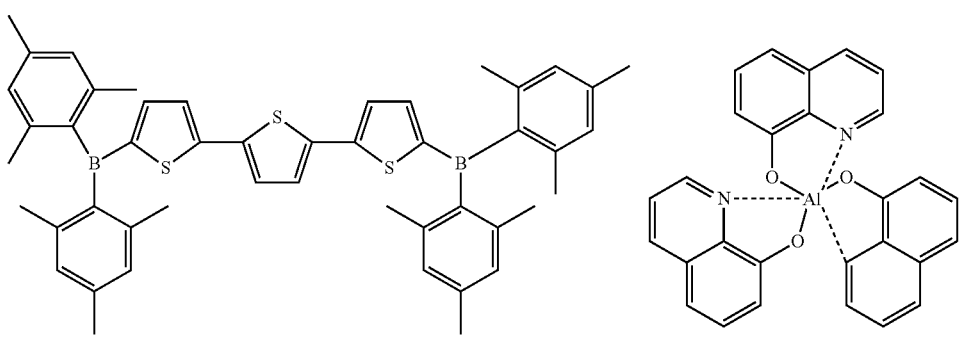
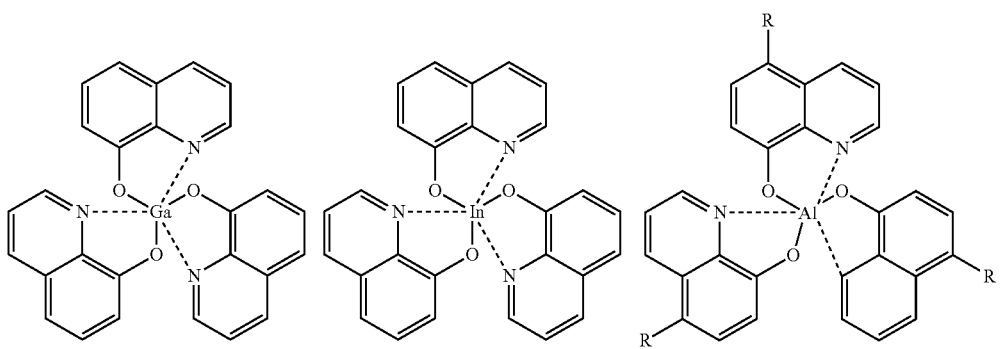
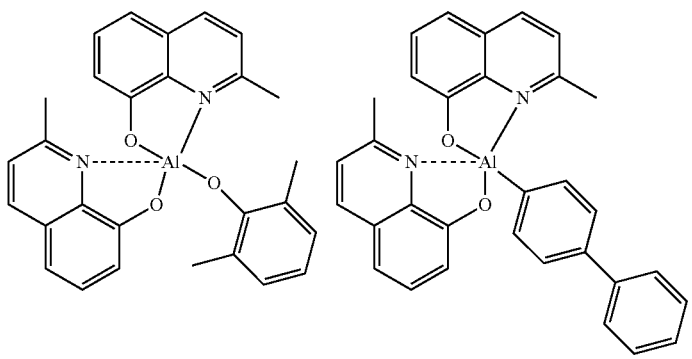

75
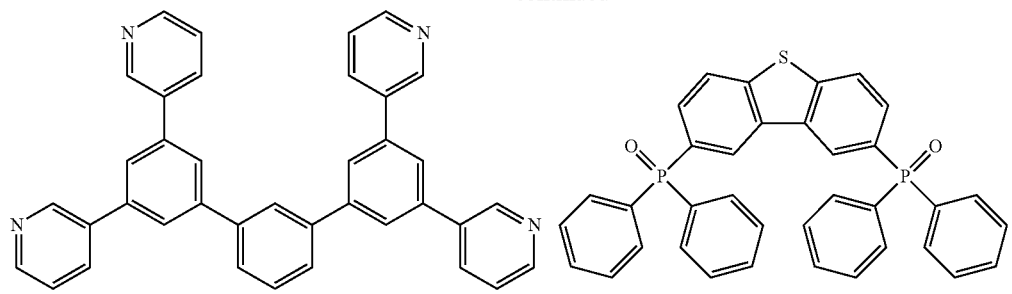
-continued
76
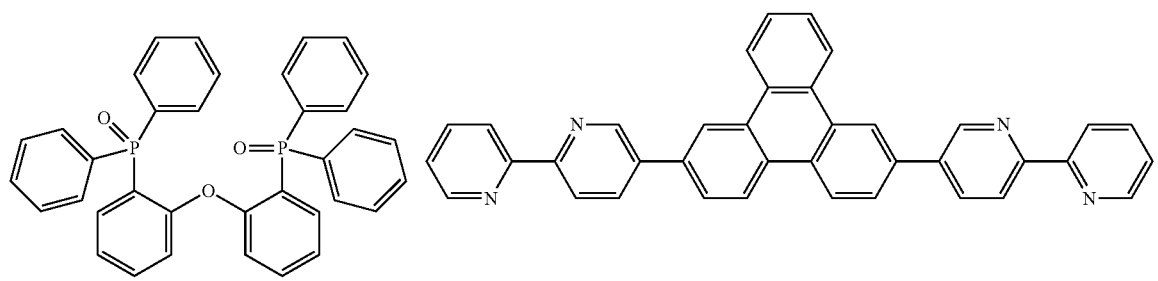
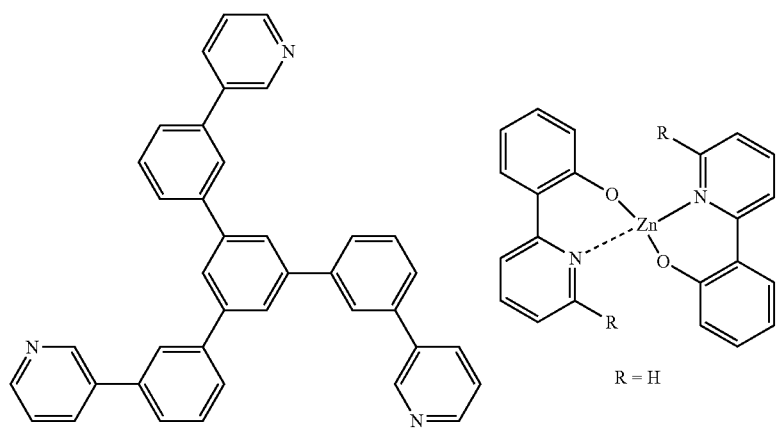
R = H
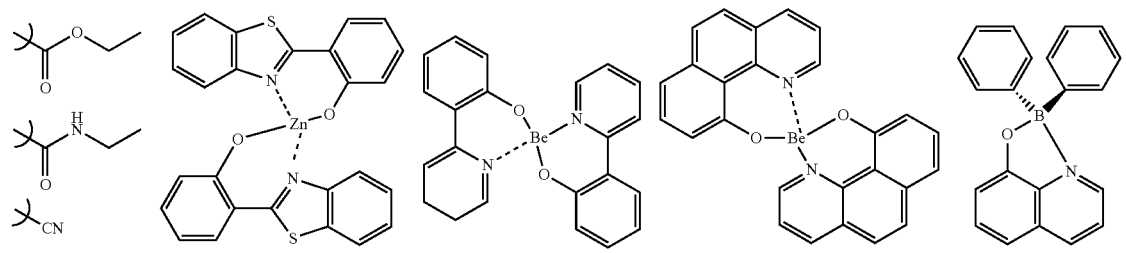

-continued
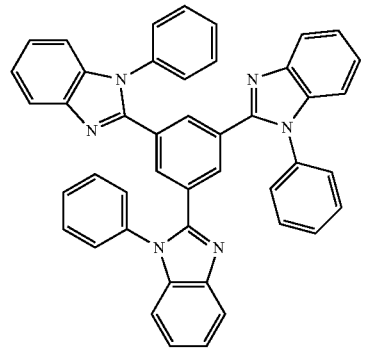
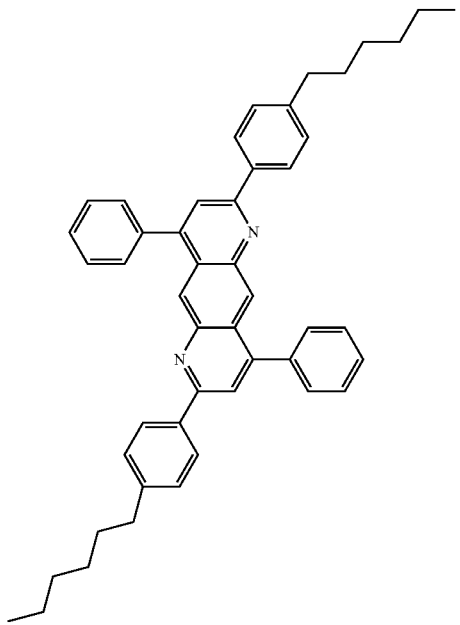
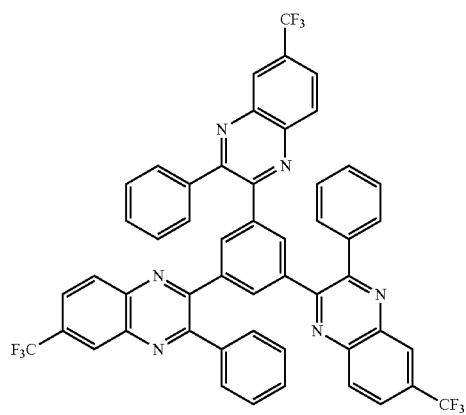
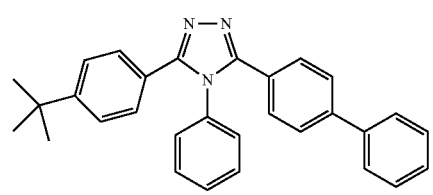
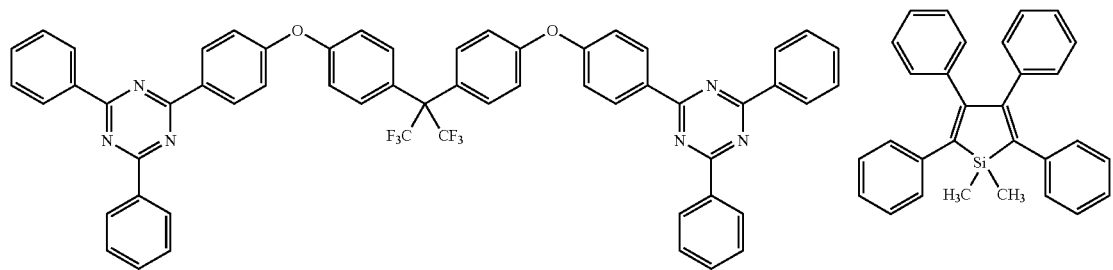
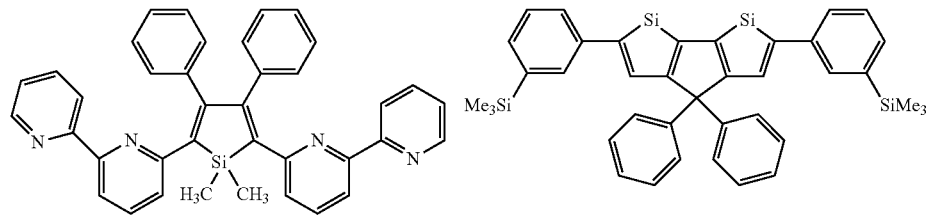

-continued
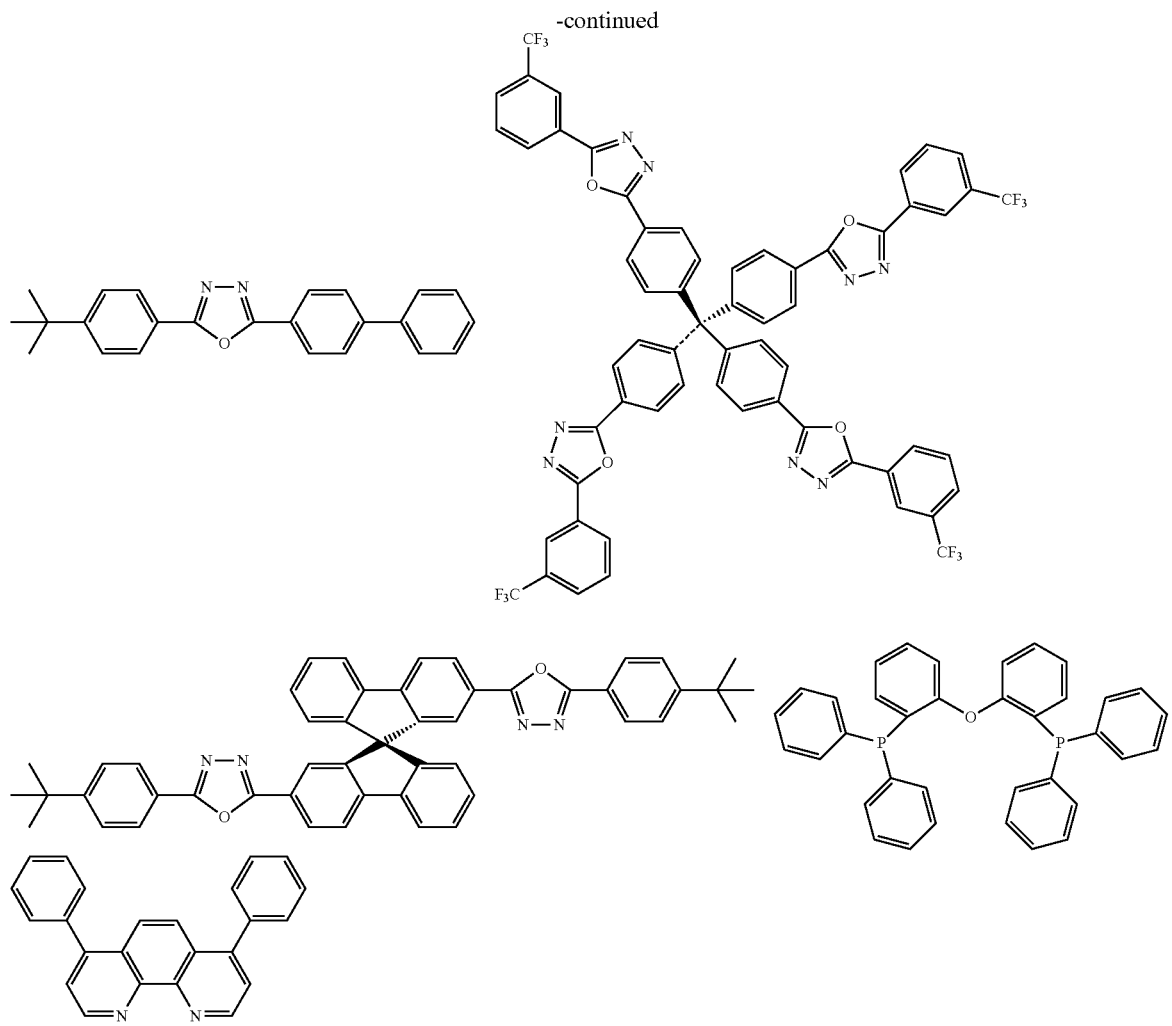
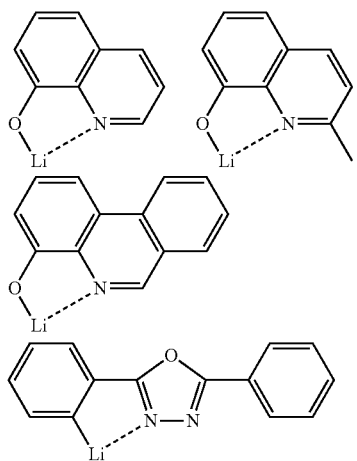
Next, preferred examples of compounds usable as an electron injection material are mentioned below.
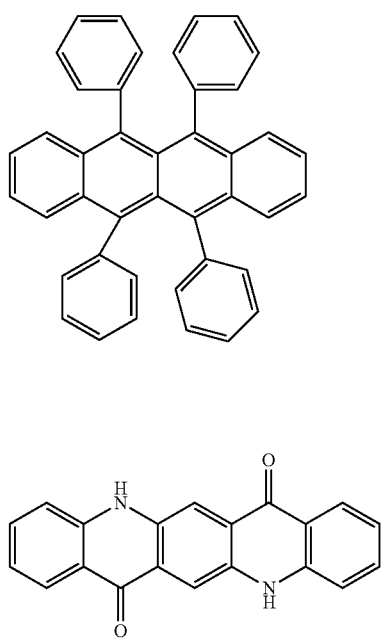
Further, preferred examples of additive compounds are mentioned below. For example, the compounds may be added as a stabilization material.

-continued

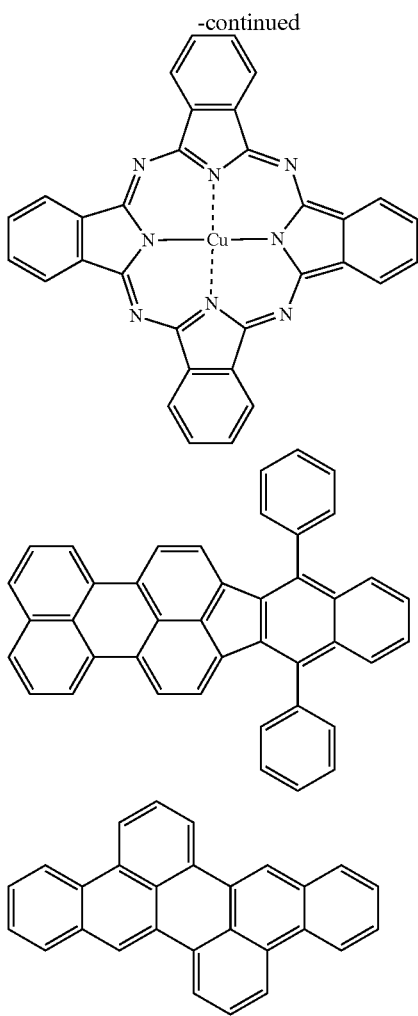

The organic electroluminescence device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

On the other hand, the phosphorescent light could not be substantially observed with an emitter consisting of an organic compound at room temperature since the excited triplet energy is converted to heat or the like due to the instability thereof, high rate constant of thermal deactivation and low rate constant of light emission and is immediately deactivated with a short lifetime. The excited triplet energy of the normal organic compound may be measured by observing light emission under an extremely low temperature condition.

The organic electroluminescence device of the invention may be applied to any of a single device, a structure with plural devices disposed in an array, and a structure having anodes and cathodes disposed in an X-Y matrix. According to the invention, an organic light-emitting device that is largely improved in luminous efficiency and lifetime may be obtained by adding the compound represented by the formula (1) to a layer between the cathode and the anode. The organic light-emitting device, such as the organic electroluminescence device, of the invention may be applied to a further wide range of purposes. For example, an organic electroluminescent display apparatus may be produced with the organic electroluminescence device of the invention, and for the details thereof, reference may be made to Seiji Tokito, Chihaya Adachi and Hideyuki Murata, "Yuki EL Display" (Organic EL Display) (Ohm-sha, Ltd.). In particular, the organic electroluminescence device of the invention may be applied to organic electroluminescent illumination and backlight which are highly demanded.

EXAMPLES

The features of the invention will be described more specifically with reference to examples below. The materials, processes, procedures and the like shown below may be appropriately modified unless they deviate from the substance of the invention. Accordingly, the scope of the invention is not construed as being limited to the specific examples shown below.

(Example 1) Synthesis of Compounds 1 to 3

(1) Synthesis of Compound 1

2-(9,9'-spirobi[fluoren]-2-yl)-4,6-diphenyl-1,3,5-triazine (SF2-TRZ)

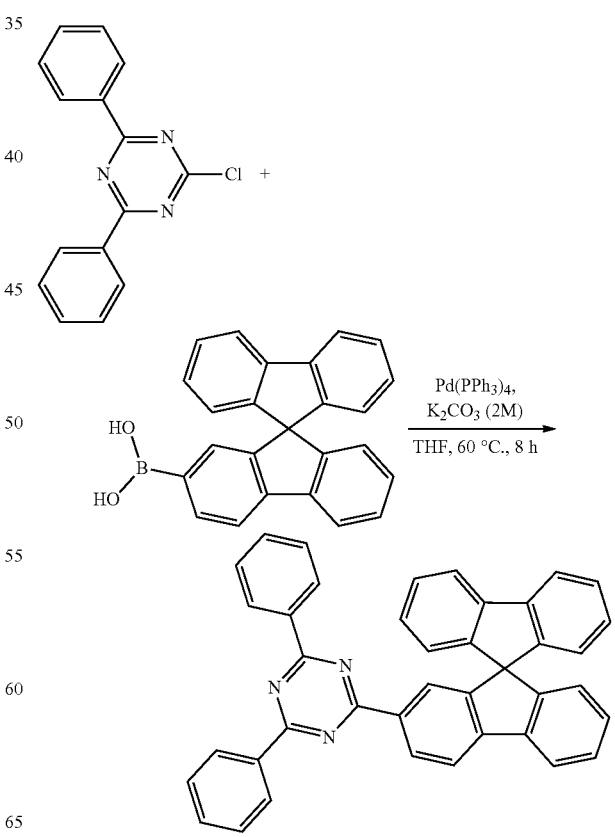

A mixture of 2-chloro-4,6-diphenyl-1,3,5-triazine (1.34 g, 5.01 mmol), 9,9'-spirobi[fluoren]-2-ylboronic 5 acid (1.89 g, 5.26 mmol), Pd(PPh$_3$)$_4$ (0.3 g, 0.27 mmol) and potassium carbonate (1.38 g, 10.02 mmol) in 30 ml of THF and 10 ml of distilled water in a 100 ml round bottom was refluxed for 6 hours under argon. The mixture was extracted with chloroform. The combined organic extracts were dried over Na$_2$SO$_4$ and concentrated by rotary evaporation. The crude product was purified by column chromatography on silica gel using 1:4 ethyl acetate/petroleum as eluent to afford a white solid SF2-TRZ (2.36 g, 86% yield). $^1$H NMR (500 MHz, DMSO-d$_6$) δ (ppm): 8.89 (d, J=8.0 Hz, 1H) 8.55 (d, J=8.5 Hz, 4H) 8.34 (d, J=8.0 Hz, 1H) 8.20 (d, J=7.5 Hz, 1H) 8.13 (d, J=7.5 Hz, 2H) 7.86 (s, 1H) 7.70-7.57 (m, 6H) 7.52-7.42 (m, 3H) 7.26-7.14 (m, 3H) 6.73 (d, J=7.5 Hz, 2H) 6.65 (d, J=7.5 Hz, 1H). $^{13}$C NMR (125 MHz, DMSO-d$_6$) δ(ppm): 171.3, 171.2, 150.0, 149.1, 148.0, 146.7, 141.8, 140.5, 135.7, 135.5, 133.4, 129.9, 129.7, 129.4, 128.9, 128.7, 124.0, 123.5, 122.1, 121.6, 121.3, 66.01. HRMS m/z: 547.26 [M]$^+$. Anal. calcd for C$_{40}$H$_{25}$N$_3$(%): C, 87.73, H, 4.60, N, 7.67; found: C, 87.70, H, 4.62, N, 7.69.

(2) Synthesis of Compound 2

2-(9,9'-spirobi[fluoren]-3-yl)-4,6-diphenyl-1,3,5-triazine (SF3-TRZ)

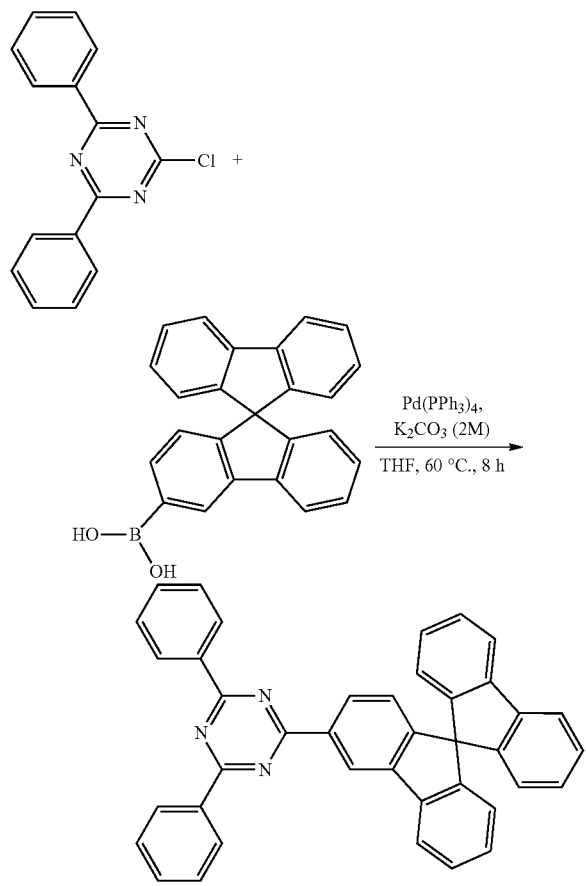

SF3-TRZ was synthesized according to the same procedure followed for SF2-TRZ using 9,9'-spirobi[fluoren]-3-ylboronic acid (1.89 g, 5.26 mmol) instead of 9,9'-spirobi[fluoren]-2-ylboronic acid. After evaporation of the solvent, the crude product was subjected to column chromatography on silica gel using 1:4 dichloromethane/petroleum as eluent to afford a yellow solid with a yield of 82%. $^1$H NMR (500 MHz, DMSO-d$_6$) δ (ppm): 9.31 (s, 1H) 8.81 (d, J=8.0 Hz, 4H) 8.54 (d, J=8.0 Hz, 1H) 8.38 (d, J=7.5 Hz, 1H) 8.09 (d, J=8.0 Hz, 2H) 7.80-7.65 (m, 6H) 7.54-7.41 (m, 3H) 7.27-7.11 (m, 3H) 6.74-6.65 (m, 3H). $^{13}$C NMR (125 MHz, DMSO-d$_6$) δ (ppm): 171.5, 148.1, 141.8, 135.8, 133.5, 129.5, 129.2, 128.6, 124.0, 123.5, 122.7, 121.2, 66.0. HRMS m/z: 547.26 [M]+. Anal. calcd for C$_{40}$H$_{25}$N$_3$(%): C, 87.73, H, 4.60, N, 7.67; found: C, 87.71, H, 4.62, N, 7.65.

(3) Synthesis of Compound 3

2-(9,9'-spirobi[fluoren]-4-yl)-4,6-diphenyl-1,3,5-triazine (SF4-TRZ)

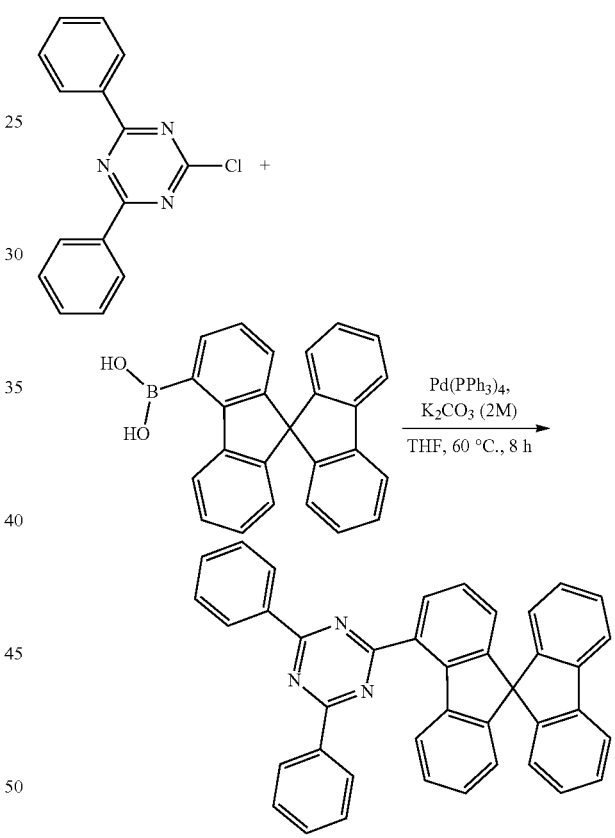

SF4-TRZ was synthesized according to the same procedure followed for SF2-TRZ using 9,9'-spirobi[fluoren]-4-ylboronic acid (1.89 g, 5.26 mmol) instead of 9,9'-spirobi[fluoren]-2-ylboronic acid. After evaporation of the solvent, the crude product was subjected to column chromatography on silica gel using 1:4 dichloromethane/petroleum as eluent to afford a yellow solid with a yield of 75%. $^1$H NMR (500 MHz, DMSO-d$_6$) δ (ppm): 8.76 (d, J=7.0 Hz, 4H) 8.08 (d, J=7.5 Hz, 2H) 8.01-7.97 (m, 2H) 7.77-7.67 (m, 6H) 7.48-7.42 (m, 2H) 7.38-7.33 (m, 1H) 7.21-7.12 (m, 4H) 6.84 (d, J=7.5 Hz, 1H) 6.75 (d, J=7.5 Hz, 2H) 6.66 (d, J=7.5 Hz, 1H). $^{13}$C NMR (125 MHz, DMSO-d$_6$) δ (ppm): 174.6, 171.5, 150.4, 149.3, 148.5, 141.8, 140.6, 139.8, 135.7, 133.5, 131.7, 129.5, 129.2, 129.1, 128.7, 128.6, 127.9, 126.5, 125.1, 124.0, 123.9, 121.1, 65.59. HRMS m/z: 547.22 [M]+. Anal. calcd for $C_{40}H_{25}N_3$(%): C, 87.73, H, 4.60, N, 7.67; found: C, 87.70, H, 4.61, N, 7.66.

(Example 2) Fabrication of Organic Electroluminescence Device Using Compound 2 as Electron Transport Material Respective thin films were deposited on a glass substrate formed with an anode made of an ITO (indium tin oxide) having a thickness of 100 nm by vacuum vapor deposition at pressures less than $3 \times 10^{-4}$ Pa. First, HAT-CN was formed to a thickness of 10 nm on ITO, Tris-PCz was formed to a thickness of 25 nm thereon, and subsequently mCBP was formed to a thickness of 5 nm. Next, mCBP and 4CzIPN as a thermally activated delayed fluorescent material were co-deposited from separate vapor deposition sources to form a layer having a thickness of 30 nm as a light-emitting layer. At this time, the concentration of 4CzIPN was 20% by weight. Compound 2 was formed to a thickness of 10 nm on the formed light-emitting layer, as a hole blocking layer. Subsequently, a co-deposition film of Compound 2 and Liq was formed to a thickness of 40 nm as an electron transport layer. At this time, the concentration of Liq was 30% by weight. Furthermore, Liq was deposited to 2 nm, and then a cathode was formed by depositing Al (aluminum) to a thickness of 100 nm, thereby achieving an organic electroluminescence device.

(Example 3) Fabrication of Organic Electroluminescence Device Using BPy-TP2

An organic electroluminescence device was fabricated in the same manner as in Example 2, except that a co-deposition film of BPy-TP2 and Liq was formed to a thickness of 40 nm instead of Compound 2 when the electron transport layer was formed.

(Comparative Example 2) Fabrication of Organic Electroluminescence Device Using T2T An organic electroluminescence device was fabricated in the same manner as in Example 2, except that T2T was formed to a thickness of 10 nm instead of Compound 2 when the electron hole blocking layer was formed.

(Comparative Example 3) Fabrication of Organic Electroluminescence Device Using T2T and BPy-TP2

An organic electroluminescence device was fabricated in the same manner as in Example 2, except that T2T was formed to a thickness of 10 nm instead of Compound 2 when the hole blocking layer was formed and a co-deposition film of BPy-TP2 and Liq was formed to a thickness of 40 nm instead of Compound 2 when the electron transport layer was formed.

(Comparative Example 4) Fabrication of Organic Electroluminescence Device Using Ir(Ppy)$_3$ An organic electroluminescence device was fabricated in the same manner as in Example 2, except that Ir(ppy)$_3$, which was a green phosphorescent material, was used as a light-emitting material instead of 4CzIPN when the light-emitting layer was formed.

(Comparative Example 5) Fabrication of Organic Electroluminescence Device Using TTPA An organic electroluminescence device was fabricated in the same manner as in Example 2, except that TTPS, which is a green fluorescent material not emitting thermally activated delayed fluorescence, was used as a light-emitting material instead of 4CzIPN when the light-emitting layer was formed.

For each of the organic electroluminescence devices fabricated in Examples 2 and 3 and Comparative Examples 2 and 3, the measurement results of the voltage-current density-luminance characteristics are shown in Table 7. V, J, EQE, LE, PE, $\lambda_{max}$ represent a driving voltage, a current density, an external quantum efficiency, a current efficiency, and a luminous efficiency at 1,000 cd/m² in luminance, respectively.

TABLE 7

|  | V (V) | J (mA/cm²) | EQE (%) | LE (cd/A) | PE (lm/W) | λmax (nm) |
|---|---|---|---|---|---|---|
| Example 2 | 5.05 | 1.37 | 19.4 | 72.9 | 41.6 | 531 |
| Example 3 | 4.62 | 1.48 | 18.5 | 67.5 | 43.3 | 533 |
| Comparative Example 2 | 4.98 | 1.37 | 19.1 | 73.2 | 41.4 | 530 |
| Comparative Example 3 | 4.82 | 1.44 | 18.4 | 69.5 | 41.3 | 531 |
| Comparative Example 4 | 7.37 | 4.03 | 6.23 | 24.8 | 9.63 | 521 |
| Comparative Example 5 | 6.30 | 9.31 | 2.68 | 10.7 | 5.09 | 545 |

LT95 that is a time until the luminance L during the constant current drive decays to 95% of the initial luminance $L_0$ was also measured. The initial luminance $L_0$ was set to 5,000 cd/m² and the measurement was conducted. LT95's of Example 2, Example 3, Comparative Example 2 and Comparative Example 3 are 35.5 h, 49.6 h, 15.6 h and 18.6 h, respectively. LT95's of Comparative Examples 4 and 5 were obviously shorter than Examples 2 and 3.

Comparing Examples 2 to 3 and Comparative Examples 2 to 3, it can be seen that the devices in which the compounds of the invention were applied to the hole blocking layer adjacent to the light-emitting layer exhibit longer LT95 and exhibit a good durability while maintaining the luminous efficiency.

Comparing Example 2 and Comparative Examples 4 to 5, it can be seen that the device in which the compound of the invention was applied to the electron transport layer in combination with the thermally activated delayed fluorescent material exhibit longer LT95 than those in which a fluorescent material not emitting thermally activated delayed fluorescent light or a phosphorescent material was used, and exhibit a higher luminous efficiency.

It can be seen from the results that the organic electroluminescence devices using the thermally activated delayed fluorescent material as the light-emitting layer and using the compound of the invention in the electron transport layer have significantly high external quantum efficiencies as compared with the organic electroluminescence devices of Comparative Examples and have much longer lifetime.

Examples 5 to 24

Organic electroluminescence devices were fabricated in the same method as in Example 2 with changing the composition of the light-emitting layer, and the results are shown in Table 8. The percentage of a material indicated as a light-emitting layer is % by weight, and the remainder of the composition is mCBP as a host material. It should be noted that if two materials are shown, the three materials including mCBP are co-deposited from different crucibles. In Examples 5 to 11, the film thickness of ITO was 50 nm, the film thickness of HAT-CN was 60 nm, the film thickness of Tris-PCz was 30 nm, and the film thickness of the co-deposited film of Compound 2 and Liq was 30 nm. In addition, the respective values were measured at the measurement luminance of 200 cd/m$^2$.

TABLE 8

| Ex. | Light-Emitting Layer | V (V) | J (mA/cm$^2$) | EQE (%) | LE (cd/A) | PE (lm/W) | $\lambda_{max}$ (nm) |
|---|---|---|---|---|---|---|---|
| 5 | 20 wt % 4CzBN | 5.13 | 1.21 | 11.2 | 16.6 | 10.2 | 467 |
| 6 | 20 wt % 4CzBN: 1 wt % TBPe | 5.48 | 1.40 | 8.4 | 14.3 | 8.6 | 466 |
| 7 | 5 wt % 5CzBN | 5.74 | 0.58 | 14.9 | 34.8 | 18.0 | 485 |
| 8 | 20 wt % 5CzBN | 4.17 | 0.48 | 15.1 | 41.3 | 30.5 | 498 |
| 9 | 5 wt % 5CzBN: 1 wt % TBPe | 6.55 | 1.07 | 9.1 | 18.7 | 8.6 | 469 |
| 10 | 10 wt % 2CzPN | 3.89 | 0.83 | 9.9 | 24.3 | 19.7 | 495 |
| 11 | 10 wt % 2CzPN: 0.5 wt % TBPe | 5.22 | 1.71 | 5.5 | 11.7 | 7.0 | 493 |
| 12 | 25 wt % 2CzTPN | 6.37 | 5.98 | 4.5 | 16.7 | 8.0 | 535 |
| 13 | 25 wt % 2CzTPN: 1 wt % TTPA | 5.59 | 3.34 | 9.5 | 29.9 | 16.5 | 510 |
| 14 | 20 wt % 4CzIPN | 4.72 | 1.48 | 18.9 | 67.7 | 43.2 | 533 |
| 15 | 20 wt % 4CzPN | 5.02 | 2.17 | 12.8 | 46.2 | 26.0 | 552 |
| 16 | 20 wt % 4CzTPN | 5.67 | 3.10 | 9.9 | 32.3 | 16.0 | 567 |
| 17 | 50 wt % 4CzIPN | 3.92 | 1.63 | 17.2 | 61.5 | 46.5 | 548 |
| 18 | 20 wt % DACT-II | 6.06 | 1.91 | 15.3 | 52.3 | 26.1 | 537 |
| 19 | 20 wt % 4CzIPN: 1 wt % TBRb | 5.23 | 2.53 | 11.0 | 39.6 | 21.6 | 560 |
| 20 | 20 wt % 4CzPN: 1 wt % TBRb | 5.57 | 3.71 | 7.6 | 26.9 | 13.7 | 561 |
| 21 | 20 wt % 4CzTPN: 1 wt % TBRb | 6.59 | 8.75 | 3.5 | 11.4 | 4.9 | 567 |
| 22 | 20 wt % 4CzIPN: 1 wt % DBP | 6.23 | 10.9 | 5.5 | 9.2 | 4.1 | 610 |
| 23 | 20 wt % 4CzPN: 1 wt % DBP | 6.44 | 11.5 | 5.3 | 8.7 | 3.7 | 610 |
| 24 | 20 wt % 4CzTPN: 1 wt % DBP | 6.88 | 11.9 | 5.4 | 8.4 | 3.3 | 610 |

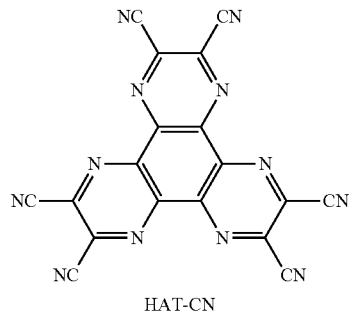 [SMILES: N#Cc1nc2c3nc(C#N)c(C#N)nc3c3nc(C#N)c(C#N)nc3c2nc1C#N]

HAT-CN

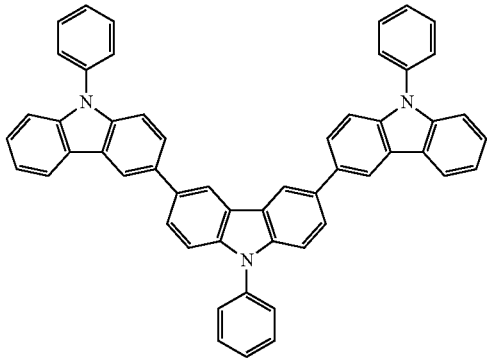

Tris-PCz

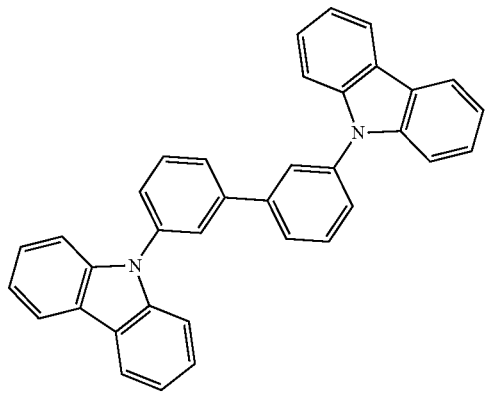

mCBP

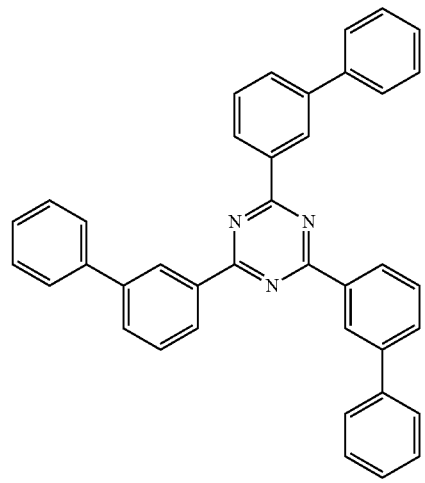

T2T

TABLE 8-continued
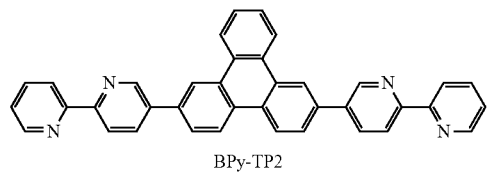 [SMILES: c1ccc(-c2ccc(-c3ccc4c5ccc(-c6ccc(-c7ccccn7)nc6)cc5c5ccccc5c4c3)cn2)nc1]
BPy-TP2
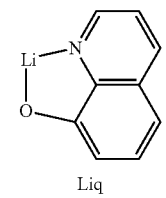
Liq
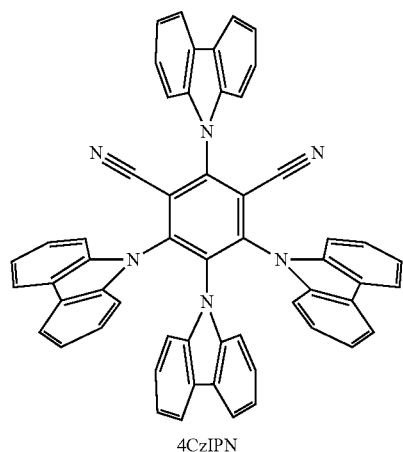 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]
4CzIPN
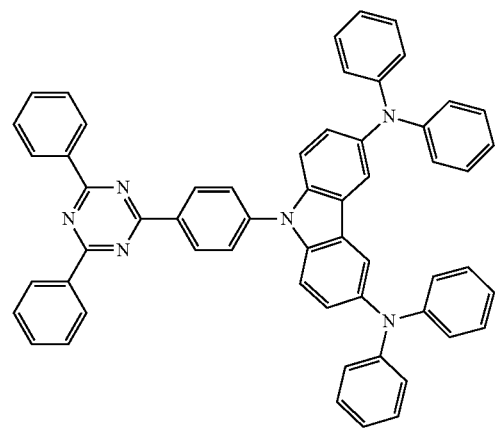
DACT-II
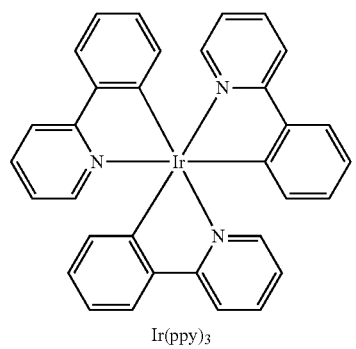
Ir(ppy)$_3$
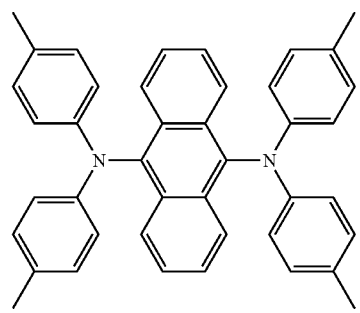
TTPA
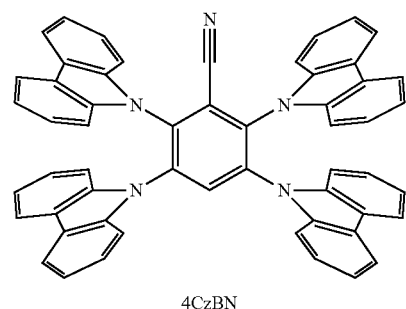 [SMILES: N#Cc1c(-n2c3ccccc3c3ccccc32)c(-n2c3ccccc3c3ccccc32)cc(-n2c3ccccc3c3ccccc32)c1-n1c2ccccc2c2ccccc21]
4CzBN
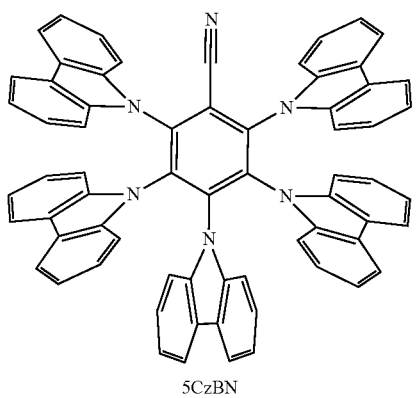 [SMILES: N#Cc1c(-n2c3ccccc3c3ccccc32)c(-n2c3ccccc3c3ccccc32)c(-n2c3ccccc3c3ccccc32)c(-n2c3ccccc3c3ccccc32)c1-n1c2ccccc2c2ccccc21]
5CzBN TABLE 8-continued
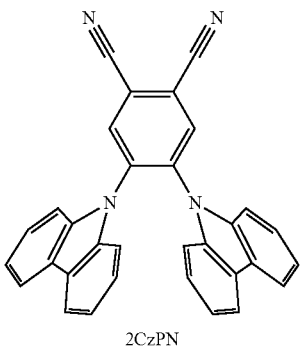 [SMILES: N#Cc1cc(-n2c3ccccc3c3ccccc32)c(-n2c3ccccc3c3ccccc32)cc1C#N]
2CzPN
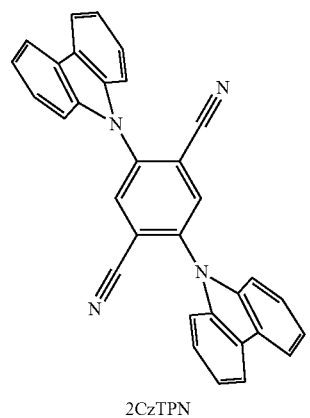 [SMILES: N#Cc1cc(-n2c3ccccc3c3ccccc32)c(C#N)cc1-n1c2ccccc2c2ccccc21]
2CzTPN
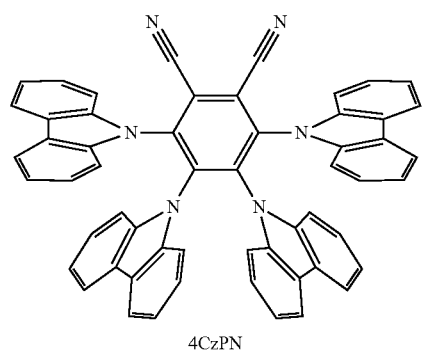 [SMILES: N#Cc1c(C#N)c(-n2c3ccccc3c3ccccc32)c(-n2c3ccccc3c3ccccc32)c(-n2c3ccccc3c3ccccc32)c1-n1c2ccccc2c2ccccc21]
4CzPN
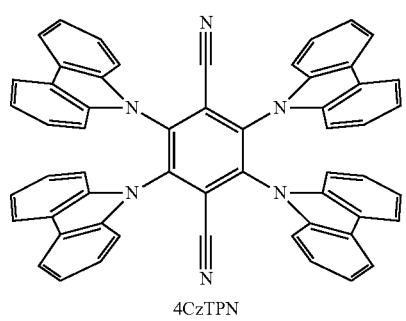 [SMILES: N#Cc1c(-n2c3ccccc3c3ccccc32)c(-n2c3ccccc3c3ccccc32)c(C#N)c(-n2c3ccccc3c3ccccc32)c1-n1c2ccccc2c2ccccc21]
4CzTPN
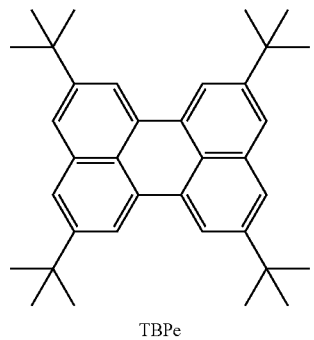 [SMILES: CC(C)(C)c1cc2cc(C(C)(C)C)cc3c4cc(C(C)(C)C)cc5cc(C(C)(C)C)cc(c(c1)c23)c54]
TBPe
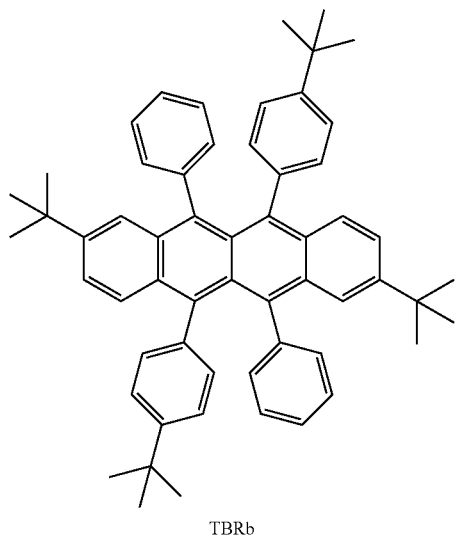
TBRb
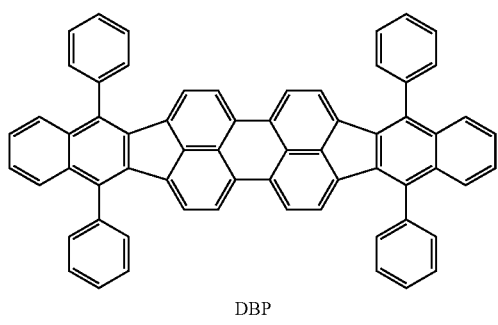 [SMILES: c1ccc(-c2c3c(c(-c4ccccc4)c4ccccc24)-c2ccc4c5ccc6c7c(ccc(c8ccc-3c2c84)c75)-c2c-6c(-c3ccccc3)c3ccccc3c2-c2ccccc2)cc1 ; "DBP"]
DBP The compounds of the invention are useful as charge transport materials. Therefore, the compounds of the invention are effectively used as charge transport materials for organic light-emitting devices such as an organic electroluminescence device. Thereby, it is possible to provide an organic electroluminescence device having a high luminous efficiency and a long lifetime. Accordingly, the invention has a high industrial applicability

The invention claimed is:

1. A light-emitting device emitting a delayed fluorescent light, which contains a delayed fluorescence emitter having a benzene ring substituted with at least one cyano group and at least one electron-donating group in an light-emitting layer, and a compound represented by the following formula (1):

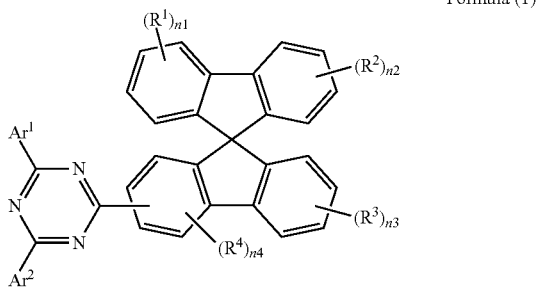

Formula (1)

wherein $Ar^1$ and $Ar^2$ each independently represent a substituted or unsubstituted aromatic group, $R^1$ to $R^4$ each independently represent a substituent, n1 to n3 are each independently an integer of from 0 to 4, and n4 is an integer of from 0 to 3.

2. The light-emitting device according to claim 1, wherein $Ar^1$ and $Ar^2$ are each independently a substituted or unsubstituted phenyl group.

3. The light-emitting device according to claim 1, wherein $R^1$ to $R^4$ are each independently an alkyl group having 1-20 carbon atoms, an aryl group having 6-40 carbon atoms, a heteroaryl group having 3-40 carbon atoms, an alkoxy group having 1-20 carbon atoms, an aryloxy group having 6-40 carbon atoms, or a heteroaryloxy group having 3-40 carbon atoms.

4. The light-emitting device according to claim 1, wherein the light-emitting layer contains the compound represented by the formula (I) as a host.

5. The light-emitting device according to claim 1, wherein $R^1$ to $R^4$ are each independently an alkyl group having 1-20 carbon atoms, an aryl group having 6-40 carbon atoms, a heteroaryl group having 3-40 carbon atoms, an alkoxy group having 1-20 carbon atoms, an aryloxy group having 6-40 carbon atoms, or a heteroaryloxy group having 3-40 carbon atoms.

6. The light-emitting device according to claim 4, wherein the compound represented by the formula (1) is also contained in a layer which is in contact with the light-emitting layer.

7. The light-emitting device according to claim 1, which is an organic electroluminescence device.

8. The light-emitting device according to claim 1, wherein the delayed fluorescence emitter has a benzene ring substituted with at least one cyano group and at least one diarylamino group.

9. The light-emitting device according to claim 8, wherein the two aryl groups of the diarylamino group are bonded to each other to form a ring.

10. The light-emitting device according to claim 1, wherein the compound represented by the formula (1) is contained in a layer which is in contact with the light-emitting layer.

11. The light-emitting device according to claim 1, wherein the spirofluorenyl group of the compound represented by the formula (I) is bonded to the triazine ring at 4-position of the spirofluorene.

12. The light-emitting device according to claim 1, wherein the spirofluorenyl group of the compound represented by the formula (I) is bonded to the triazine ring at 2-position of the spirofluorene.

13. The light-emitting device according to claim 1, wherein the spirofluorenyl group of the compound represented by the formula (I) is bonded to the triazine ring at 3-position of the spirofluorene.

* * * * *